United States Patent
Minamitake et al.

(10) Patent No.: US 7,138,489 B2
(45) Date of Patent: Nov. 21, 2006

(54) METHOD FOR PRODUCING A MODIFIED PEPTIDE

(75) Inventors: Yoshiharu Minamitake, Nitta-machi (JP); Masaru Matsumoto, Tatebayashi (JP); Tomohiro Makino, Tatebayashi (JP)

(73) Assignee: Daiichi Asubio Pharma Co., Ltd., Tokyo (JP)

( * ) Notice: Subject to any disclaimer, the term of this patent is extended or adjusted under 35 U.S.C. 154(b) by 0 days.

(21) Appl. No.: 10/500,018

(22) PCT Filed: Apr. 10, 2003

(86) PCT No.: PCT/JP03/04590

§ 371 (c)(1),
(2), (4) Date: Jan. 31, 2005

(87) PCT Pub. No.: WO03/084983

PCT Pub. Date: Oct. 16, 2003

(65) Prior Publication Data

US 2005/0131208 A1    Jun. 16, 2005

(30) Foreign Application Priority Data

Apr. 11, 2002 (JP) .............................. 2002-109761

(51) Int. Cl.
| | |
|---|---|
| C07K 1/00 | (2006.01) |
| C07K 1/06 | (2006.01) |
| C07K 1/08 | (2006.01) |
| C07K 1/107 | (2006.01) |
| A61K 38/02 | (2006.01) |

(52) U.S. Cl. ...................... 530/334; 530/333; 530/335; 530/336; 530/337

(58) Field of Classification Search ............... 285/229, 285/114; 530/333–337
See application file for complete search history.

(56) References Cited

FOREIGN PATENT DOCUMENTS

| EP | 0745669 A2 | 12/1996 |
|---|---|---|
| EP | 0794254 A2 | 9/1997 |
| EP | 0794255 A2 | 9/1997 |
| EP | 0978565 A1 | 2/2000 |
| EP | 1076097 A1 | 2/2001 |
| EP | 1179537 A1 | 2/2002 |
| EP | 1197496 A1 | 4/2002 |

OTHER PUBLICATIONS

Barlos et al., Application of 2-chlorotrityl resin in solid phase synthesis of (Leu$^{15}$)-gastrin I an unsulfated cholecystokinin octapeptide, Int. J. Peptide Protein Res. 38, 1991, 555-561.

Barlos et al., Veresterung Von Partiell Geschützten Peptide-Fragmenten Mit Harzen. Einsatz Von 2-Chlortritylchlorid Zur Synthese Von Leu$^{15}$-Gastrin I, Tetrahedron Letters, vol. 30, No. 30, 3947-3950, 1989.

(Continued)

*Primary Examiner*—Karen Cochrane Carlson
*Assistant Examiner*—Marsha Tsay
(74) *Attorney, Agent, or Firm*—Hunton & Williams LLP

(57) ABSTRACT

The present invention is a method for producing a peptide or a protein in which a side chain contains a modified amino acid residue, which comprises chemically producing a peptide fragment containing an amino acid residue having a modified side chain using an weak acid-cleavable resin, producing a peptide fragment containing no amino acid residue having a modified side chain using a genetic recombination method or/and an enzymatic method, and condensing the resulting two kinds of peptide fragments and, according to the present invention, a peptide or a protein containing modification such as acylation, glycosylation and phosphorylation can be obtained effectively and at high quality.

28 Claims, 9 Drawing Sheets

OTHER PUBLICATIONS

Bednarek et al., Structure-Function Studies in the New Growth Hormone-Releasing Peptide, Ghrelin: Minimal Sequence of Ghrelin Necessary for Activation of Growth Hormone Secretagogue Receptor 1a, J. Med. Chem. 2000, 43, 4370-7376.

Dawson et al., Synthesis of Proteins By Native Chemical Ligation, Science, vol. 266, Nov. 4, 1994, 776-779.

Energy Argus, Latin American Power Watch, Columbia's Porse III attracts interest, vol. XX, 19, Sep. 28, 2004, 1-8.

Ishimaru et al., Stability of the Octanoyl Group Essential for Expressing the Biological Activities of Rat Ghrelin, Peptide Science 2002, 157-160.

Kawakami et al., Polypeptide Synthesis Using An Expressed Peptide As a Building Block Via the Thioester Method, Tetrahedron Letters 41, (2000) 2625-2628.

Kawakami et al., Synthesis of Reaper, a Cysteine-Containing Polypeptide, Using a Peptide Thioester in The Presence of Silver Chloride As An Activator, Tetrahedron Letters 39 (1998) 7901-7904.

Kiso et al., A New Stepwise Deprotection Method Using Reductive Acidolysis Followed By Fluoride Ion In Solid Phase Peptide Synthesis[1], Tetrahedron Letters, vol. 34, No. 47, 7599-7602, 1993.

Kitagawa et a., Facile Solid-Phase Synthesis of Sulfated Tyrosine-Containing Peptides: Part II. Total Synthesis of Human Big Gastrin-II AND Its C-Terminal Glycine-Extended Peptide (G34-Gly Sulfate) by the Solid-Phase Segment Condensation Approach[1,2], Chem., Pharm. Bull. 49(8) 958-963 (2001).

Kojima et al., Ghrelin is a growth-hormone-releasing acylated peptide from stomach, Nature, vol. 402, Dec. 9, 1999, 656-660.

Matsumoto et al., Structural Similarity of Ghrelin Derivatives to Peptidyl Growth Hormone Secretagogues, Biochemical and Biophysical Research Communications 284, 655-659 (2001).

International Preliminary Examination Report for PCT/JP2003/004590, dated Apr. 10, 2003 (English Translation).

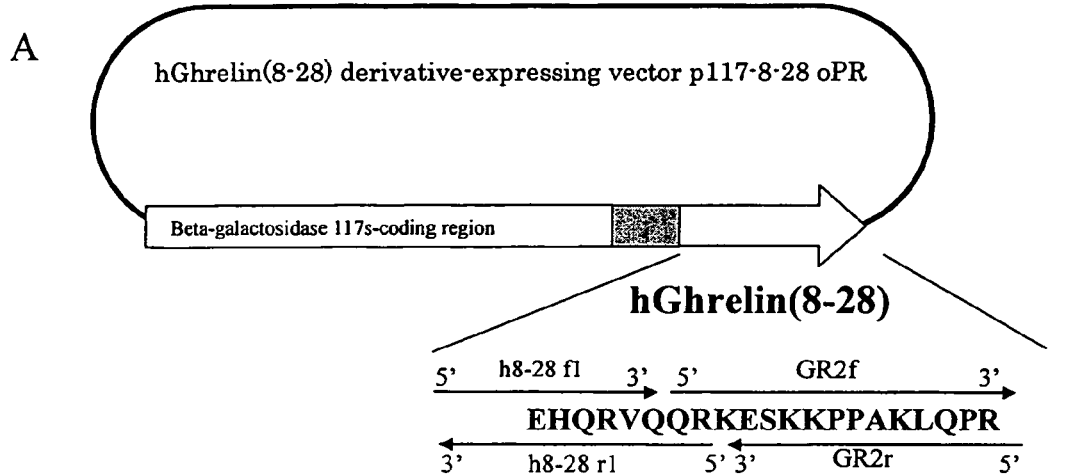

h8-28 f1  5'- TCC<u>CCGCGG</u>GAACACCAGCGCGTCCAG -3'
GR2f    5'- CAGCGTAAGGAATCCAAGAAGCCACCAGCTAAACTGCAGCCACGA<u>TGAG</u> -3'
GR2r    5'- <u>TCGACTCA</u>TCGTGGCTGCAGTTTAGCTGGCTTCTTGGATTCCTT -3'
h8-28 r1 5'- ACGCTGCTGGACGCGCTGGTGTTC<u>CCGCGG</u>GGA -3'

Synthetic oligo-DNAs used in annealing method
- h8-28 f1, GR2f, h8-28 r1 and GR2r are synthetic oligo-DNA nucleotide sequence.
- Bold underlined bases in GR2f and GR2r sequences are termination codon and cohesive end of SalI cleavage site.
- Bold underlined bases in h8-28 f1 and h8-28 r1 sequences correspond to SalI cleavage site.

 corresponds to a linker sequence EPHHHHPGGRQMHGYDADVRLYRRHHGSGSPSRHRR.

B

| Beta-Galactosidase 117s | Linker sequence | hGhrelin(8-28) |

Linker sequence   EPHHHHPGGRQMHGYDADVRLYRRHHGSGSPSRHRR
hGhrelin(8-28)    EHQRVQQRKESKKPPAKLQPR is beta-galactosidase 117 amino acids Underlined part is hGhrelin (8-28)

☐ represents a recognition site of Kex2, and ↓ represents a cleavage site of Kex2.

Fig. 7

117s 8-28 oRR
Fusion protein expressed in p117 8-28 oPR

[-------117s-------]EPHHHHPGGRQMHGYDADVRLY[RR]HHGSGSPSRH[RR]EHQRV
QQRKESKKPPAKLQPR

OmpT ↓    Kex2 ↓

117s PE

[-------117s-------]EPHHHHPGGRQMHGYDADVRLY[RR]HHGSGS*E*SRH[RR]EHQRV
QQRKESKKPPAKLQPR

117s SPEE

[-------117s-------]EPHHHHPGGRQMHGYDADVRLY[RR]HHGSG*EE*SRH[RR]EHQRV
QQRKESKKPPAKLQPR

117s SPEE+12aa

[-------117s-------]EPHHHHPGGRQ *MHGEDEDVFVFT* MHGYDADVRLY[RR]

OmpT ↓

HHGSG*EE*SRH[RR]EHQRVQQRKESKKPPAKLQPR

Kex2 ↓

117s VH

[-------117s-------]EPHHHHPGGRQMHGYDADVRLY[RR]HHGSGSPS*V*H[RR]EHQRV
QQRKESKKPPAKLQPR

117s HV

[-------117s-------]EPHHHHPGGRQMHGYDADVRLY[RR]HHGSGSPS*HV*[RR]EHQRV
QQRKESKKPPAKLQPR

117s FE

[-------117s-------]EPHHHHPGGRQMHGYDADVRLY[RR]HHGSGSPS*FE*[RR]EHQRV
QQRKESKKPPAKLQPR

[-------117s-------] is beta-galactosidase 117 amino acids

Underlined part represents hGhrelin(8-28).

[RR] and [RR] represent cleavage recognition sites of OmpT and Kex2.

A slant underlined part represents a residue in which a mutation is introduced.

Fig. 8
A
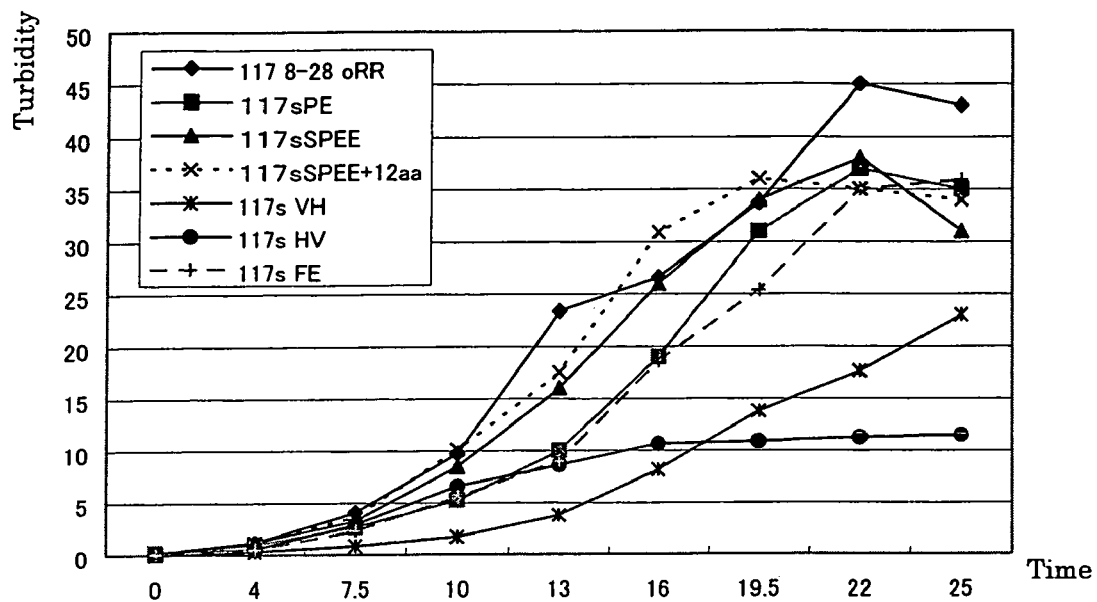
B
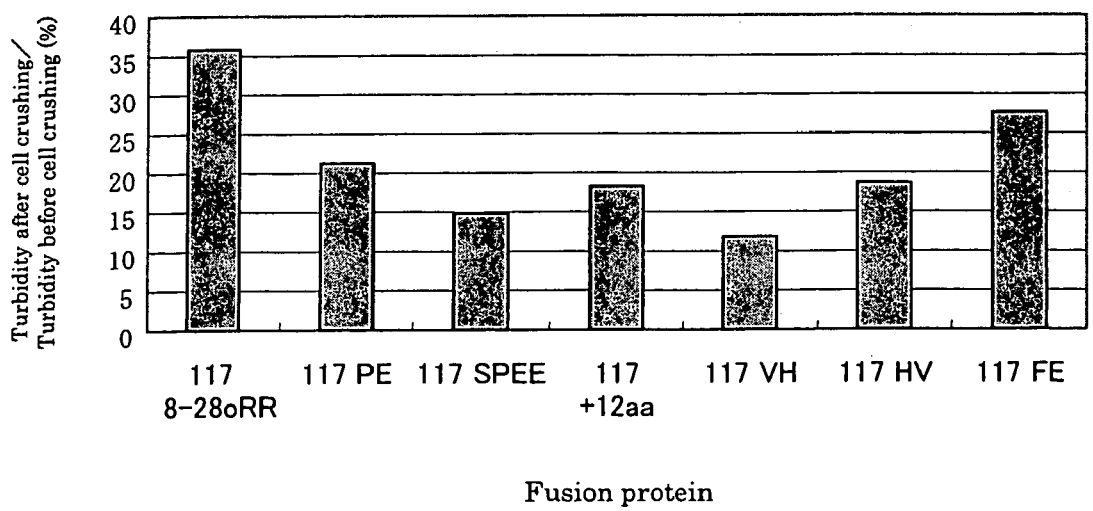

Fig. 10
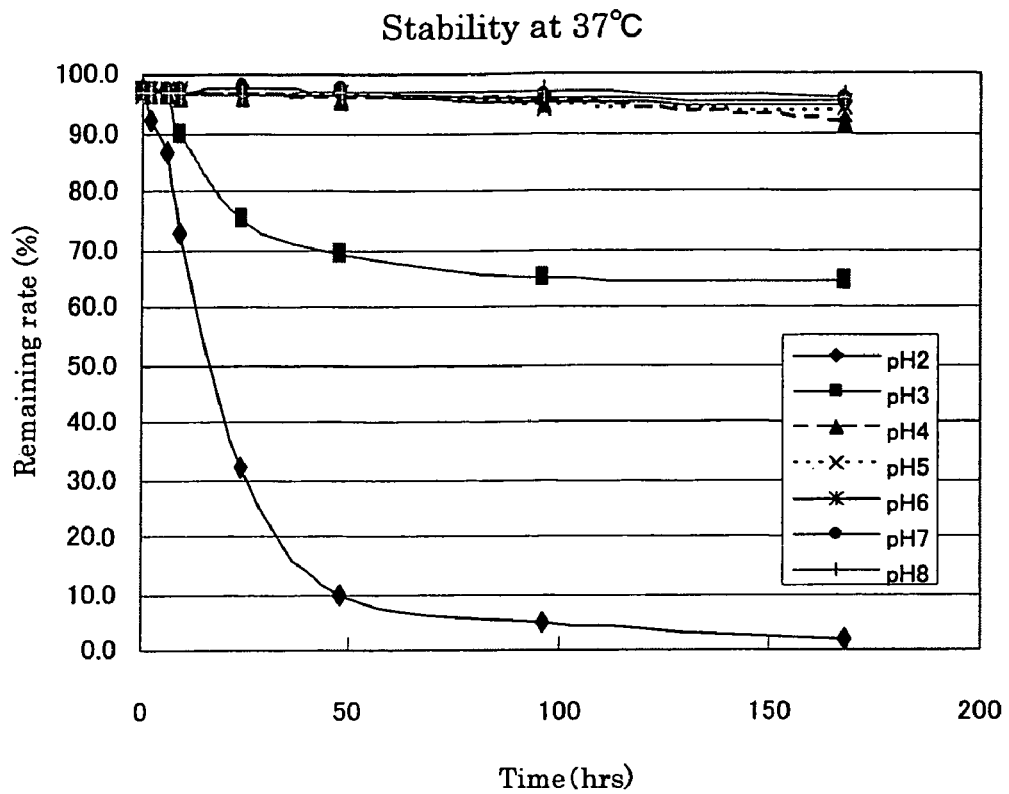
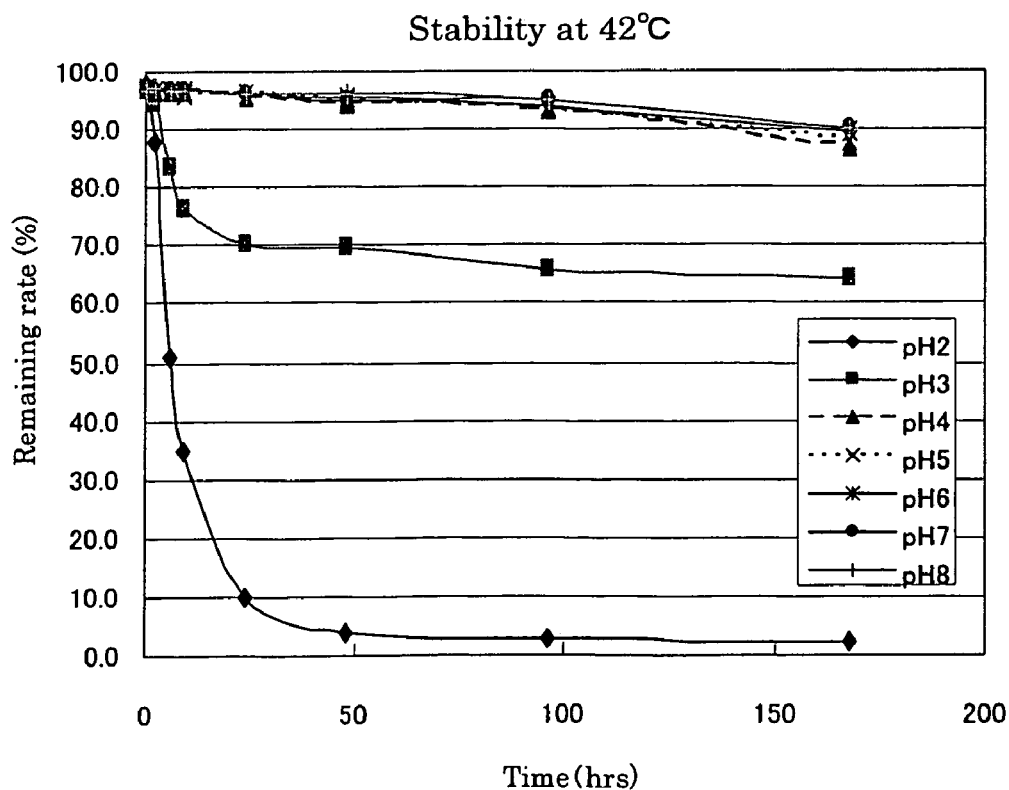

METHOD FOR PRODUCING A MODIFIED PEPTIDE

This application is a National Stage Application of International Application No. PCT/JP03/04590 filed Apr. 10, 2003, which claims priority to JP 109761/2002, filed Apr. 11, 2002.

TECHNICAL FIELD

The present invention relates to a method for producing a modified peptide or protein, and a method for producing a protected peptide fragment containing one or more modified amino acids or non-amino acids, which is suitably used for the aforementioned production method.

BACKGROUND TECHNIQUE

An endogenous growth hormone secretagogue (GHS) for a growth hormone secretagogue receptor (GHS-R) which is one of orphan receptors was purified and isolated from rat stomach in 1999, and was named ghrelin (Kojima et al., Nature, vol. 402, p. 656–660, 1999). This peptide is known to have a characteristic structure in which a hydroxy group of a serine residue is acylated with a fatty acid. Further, ghrelin in which a serine residue or a threonine residue at the 3-position contains a fatty acid-modified site was isolated also from a vertebrate other than rat, such as human, mouse, pig, fowl, eel, cow, horse, sheep, frog, trout or dog, or was presumed from a cDNA (Table 1). For example, human ghrelin consists of 28 amino acids, and the serine side chain at the 3-position is acylated with a fatty acid (N-octanoic acid). It has been found that this novel peptide has strong growth hormone secretagogue activity, and modification of 3-positional serine or threonine with a fatty acid is essential for manifestation of the activity (Kojima et al., Nature, vol. 402, p. 656–660, 1999). In addition, it has been clarified that ghrelin secreted from stomach functions as a blood hormone in regulating secretion of growth hormone, and thus much attention has been paid to a physiological role of ghrelin and its application to medicaments.

TABLE 1

| Human | GSS (n-octanoyl) | FLSPEHQRVQQRKESKKPPAKLQPR |
| | GSS (n-octanoyl) | FLSPEHQRVQRKESKKPPAKLQPR |
| Rat | GSS (n-octanoyl) | FLSPEHQKAQQRKESKKPPAKLQPR |
| | GSS (n-octanoyl) | FLSPEHQKAQRKESKKPPAKLQPR |
| Mouse | GSS (n-octanoyl) | FLSPEHQKAQQRKESKKPPAKLQPR |
| Porcine | GSS (n-octanoyl) | FLSPEHQKVQQRKESKKPAAKLKPR |
| Bovine | GSS (n-octanoyl) | FLSPEHQKLQRKEAKKPSGRLKPR |
| Ovine | GSS (n-octanoyl) | FLSPEHQKLQRKEPKKPSGRLKPR |
| Canine | GSS (n-octanoyl) | FLSPEHQKLQQRKESKKPPAKLQPR |
| Eel | GSS (n-octanoyl) | FLSPSQRPQGKDKKPPRV-NH$_2$ |
| Trout | GSS (n-octanoyl) | FLSPSQKPQVRQGKGKPPRV-NH$_2$ |
| | GSS (n-octanoyl) | FLSPSQKPQGKGKPPRV-NH$_2$ |
| Chicken | GSS (n-octanoyl) | FLSPTYKNIQQQKGTRKPTAR |
| | GSS (n-octanoyl) | FLSPTYKNIQQQKDTRKPTAR |
| | GSS (n-octanoyl) | GLSPTYKNIQQQKDTRKPTARLH |
| Bullfrog | GLT (n-octanoyl) | FLSPADMQKIAERQSQNKLRHGNM |
| | GLT (n-decanoyl) | FLSPADMQKIAERQSQNKLRHGNM |
| | GLT (n-octanoyl) | FLSPADMQKIAERQSQNKLRHGNMN |

TABLE 1-continued

| Tilapia | GSS (n-octanoyl) | FLSPSQKPQNKVKSSRI-NH$_2$ |
| Catfish | GSS (n-octanoyl) | FLSPTQKPQNRGDRKPPRV-NH$_2$ |
| | GSS (n-octanoyl) | FLSPTQKPQNRGDRKPPRVG |
| Equine | GSS (n-butanoyl) | FLSPEHHKVQHRKESKKPPAKLKPR |

In addition to an octanolyl group-(C8)-modified peptide, there are butanoyl group (C4)-, hexanoyl group (C6)-, decanoyl group (C10)- and dodecanoyl group (C12)-modified peptides. Furthermore, there are unsaturated fatty acid-modified peptides.

Some peptides or proteins, like ghrelin and cholecystokinin, manifest their physiological role when a specific amino acid residue in the amino acid sequence has undergone modification such as acylation, sulfonation, glycosylation or phosphorylation. It is thought that these modifications are given by an elaborate enzyme system in a living body, and a general method for producing a modified peptide or protein in a high quality and effective manner in large quantities has not been reported yet. For example, since ghrelin exhibits growth hormone secretagogue activity by modification of a specific amino acid side chain with a long chain fatty acid, fatty acid modification is an essential structural element. However, what enzyme system of a living body is involved for ester-binding of a fatty acid to a hydroxy group of a specific amino acid side chain or for extention of a fatty acid has not been known yet. Since, in particular, ghrelin is the first physiologically active peptide clarified to have a structure in which a hydroxy group of an amino acid side chain is modified with a fatty acid, although the present peptide is a useful peptidic hormone which is expected to be a promising medicament as a curative medicine for eating disorder, a drug for promoting growth hormone, secretion, etc., production of a peptide having fatty acid modification in a specific hydroxy-containing amino acid side chain has not been generalized. That is, an industrial production method which is advantageous for mass production of such peptide has not been established at present.

Currently, various peptide or protein preparations such as insulin, growth hormone, calcitonin, atrial natriuretic peptide, LH-RH derivative and adrenocorticotropic hormone derivative are used as a medicament. As a method for producing these peptides or proteins, production by a chemical synthesis method, an enzymatic method and a genetic recombination method are known. Although, which method to be employed is appropriately selected, generally a chemical synthesis method is selected when the number of residues is small, and an enzymatic method or a genetic recombination method is selected when the number of residues is large.

A chemical synthesis method, for example, is a method by which a physiologically active peptide or protein having modification such as ghrelin, etc. can be steadily produced. Many production methods using a chemical synthesis method have been already reported as a method for producing a modified peptide or protein. In the case of ghrelin, methods are reported by Bednarek et al. (J. Med. Chem., vol. 43, p. 4370–4376, 2000) and Matsumoto et al. (Biochem. Biophys. Res. Commun., vol. 284, p. 655–659, 2001). Also, International Publication No. WO 01/07475 describes a production method by a chemical synthesis method, as a method for producing a peptide which is ghrelin or a ghrelin derivative, or a salt thereof. However, in a production by a chemical synthesis method, there is usually a limitation to a chain length of a peptide which can be synthesized, while retaining constant quality (purity). Although a liquid phase chemical synthesis method can synthesize a peptide of high purity, the method is not common for synthesis of a long chain peptide due to the solubility, long producing step and special techniques necessary for the reaction treatment. Namely, effective production in large quantities is difficult in a production method using a liquid phase chemical synthesis method. On the other hand, a solid phase chemical synthesis for extending a peptide chain on a resin has a simplified step, and is more advantageous for mass production, but this method also has a limitation on a constructable chain length to obtain desired products having constant quality. In addition, there is also a problem that the method is inferior in economic property because of excessive reagents used, in particular, in production of a long chain peptide.

Meanwhile, a method for enzymatically coupling a peptide fragment such as an enzymatic method is excellent in that protection of an amino acid side chain can be minimized. In this method, however, since a reverse reaction of hydrolysis is usually used, the condition setting is in principle difficult, and thus the method is not practical.

On the other hand, production of a physiologically active peptide or protein by a genetic recombination method is a useful production method suitable for mass production. However, in a method using a prokaryote such as *Escherichia coli* having high productivity, it is difficult to directly produce a peptide having a modified site, since a prokaryote has no posttranslational modification system. In a genetic recombination method using a eukaryote such as yeast and various egg cells, modification such as glycosylation, acylation, sulfonation and phospholyration is possible, however, regarding a fatty acid, for example, it is difficult to introduce only fatty acid having a constant length. Among isolated ghrelins, ghrelins having not only octanoic acid (C8) but also butanoic acid (C4), decanoic acid (C10), or unsaturated fatty acid of them have been found, and thus it is clear that controlling the introduction of a fatty acid having a specific chain length is difficult. In addition, since productivity by a eukaryote is generally low, production system of yeast and various egg cells having modification system has much room for improvement from a viewpoint of mass production of a modified peptide or protein such as ghrelin.

As described above, although a chemical synthesis method has been known as a method for synthesizing a modified peptide or protein, and there are already various reports, such method has a room for improvement in yield and cost for the purpose of mass production. It is difficult to directly produce a modified peptide or protein by a genetic recombination method using a prokaryote such *Escherichia coli*. Also, production by a genetic recombination method using a eukaryote such as yeast has a problem in unity or productivity, and thus there is a room for improvement in order to overcome this problem. In an enzymatic method using a reverse reaction of hydrolysis, it is difficult to set respective condensation conditions and, therefore, this method cannot be said an advantageous method for mass production.

As described above, there has been a room for further improvement in an effective production of a peptide or a protein having modification such as glycosylation, acylation, sulfonation, phosphorylation, etc., which satisfies quality and quantitative elements, by the independent application of a conventionally known chemical synthesis method, an enzymatic method or a genetic recombination method alone.

Then, as one of methods utilizing advantages of the aforementioned methods and compensating the defects of the methods, there may be exemplified a semi-synthesis method obtained by combination of a chemical synthesis method and a genetic recombination method. An important point of the production method is to effectively produce a peptide fragment in a form suitable for condensation. A peptide fragment having a modified amino acid residue (hereinafter, also referred to as modified component) and a peptide fragment having no modified amino acid residue (hereinafter, also referred to as non-modified component) may be in an N-terminal side or a C-terminal side, or there may be a plurality of modified components. A production method can be designed appropriately depending on a desired peptide or protein. As one example, the case where a modified component is present on an N-terminal side, and another peptide fragment to be condensed with the peptide fragment (modified component) is a non-modified component will be described in detail.

A native chemical ligation method (Dawson et al., Science, vol. 266, p. 776–779, 1994) which has been paid attention to recently has a defect that a Cys residue remains on a ligation site. Recently, however, a thioester method obtained by improvement of the aforementioned method has been proposed. For example, Kawakami et al. have reported a phosphorylated peptide synthesis by a method using thioester (Tetrahedron Letter, vol. 41, p. 2625–2628, 2000).

A specific example of the thioester method will be described below. In an example of synthesis of a phosphorylated p21Max protein (Kawakami et al., Tetrahedron Lett., vol. 39, p. 7901–7904, 1998), a peptide fragment (modified component)(13 mer) containing a phosphoric acid-modified site is produced as thioester by a solid phase chemical synthesis method. On the other hand, a peptide fragment having a sequence in which one amino acid residue is added to the N-terminus of a non-modified component is produced in *Escherichia coli*, glyoxylic acid is acted on this in the presence of a divalent copper or nickel ion to convert an amino acid residue added to the N-terminus into an α-ketoacyl group, and a side chain amino group is protected with a Boc group. Then, an α-ketoacyl group is removed with phenylenediamine, thereby a peptide fragment (non-modified component) in which only an amino acid group in the N-terminal amino acid residue is freed is produced. Finally, these both fragments are condensed by adding an active esterifying agent such as silver salt, excessive HOOBt, etc.

Also in the aforementioned method, there still remains the following problem. There is a problem on stability of the thioester in production of a peptide fragment (modified component), and it is reported that the yield is 11%. In addition, for production of a peptide fragment (non-modified component), the said method using an α-ketoacyl group is a potential choice as a chemical method of freeing a N-terminal amino group. However, the method has a safety problem in that an α-ketoacyl group is unstable, and a mutagenic substance such as phenylenediamine is used for eliminating the group, when a physiologically active peptide or protein for a medicament is produced. In addition, an active esterifying agent such as silver salt, excessive HOOBt, etc. is used in a reaction of condensing both fragments and, therefore, there is also a problem on racemization, toxicity and cost.

A semi-synthesis method combining a chemical synthesis method and a genetic recombinant method is described in International Publication No. WO 01/07475 as a method for producing a peptide which is ghrelin or a ghrelin derivative, or a salt thereof. More specifically, there is described a method for producing rat ghrelin (1–28) by condensing rat ghrelin (1–5) prepared by a chemical synthesis method with rat ghrelin (6–28) prepared by a genetic recombination method. However, since such method also has the following problem, there is a room for much improvement in order to obtain an efficient and industrially advantageous production method. That is, there is a room for improving productivity in consideration of that, when rat ghrelin (1–5) is obtained by eliminating a peptide chain with TFA from a resin, a Boc group and a t-Bu group are at the same time removed, and thus it is necessary to introduce again a Boc group into a N-terminus, and that since a Ser side chain becomes unprotected, a strong activating agent can not be used for condensation with rat ghrelin (6–28), etc. Furthermore, in a process of condensing protected rat ghrelin (1–5) and protected rat ghrelin (6–28), a C-terminal amino acid of an acylpeptide fragment part may be racemized, and therefore there is a room for improvement in order to prevent this problem. Herein, ghrelin (m–n) means a peptide having an amino acid sequence of $m^{th}$ to $n^{th}$ from an N-terminus of ghrelin. Hereinafter, the same.

In addition, there are some problems in preparation of a protected peptide fragment (non-modified component). A method for producing protected rat ghrelin (6–28) described in International Publication No. WO 01/07475 fundamentally adopts a two-step enzyme treatment method (International Publication NO. WO 99/38984) and, as a processing enzyme therefor, two kinds of enzymes, i.e. a recombinant V8 protease derivative (rV8D5)(JP-A No. 9-47291) and a Kex2 protease (JP-A No. 10-229884), are used. However, since a plasmid (pG97s rGR) expressing a fusion protein containing protected rat ghrelin (6–28) is constructed based on a plasmid (JP-A No. 9-296000) which highly expresses a fusion protein of *Escherichia coli* β-galactosidase derivative and human parathyroid hormone (1–34), a linker sequence suitable for its amino acid sequence may need to be selected in preparation of a protected peptide fragment (non-modified component).

Furthermore, since there is phenomenon that a protecting group for protected rat ghrelin (6–28) is eliminated in an aqueous solution, a recovery rate in purification step is very low as 10%, and therefore there is still a problem for stable supply of ghrelin in large quantities.

As described above, even a combination of a chemical synthesis method and a genetic recombinant method has a further problem in order to realize a method for efficiently producing a modified physiologically active peptide or protein, which is very safe enough to be used as a medicament.

DISCLOSURE OF THE INVENTION

An object of the present invention is to provide a simple and effective industrial method for producing a modified peptide or a protein. Specifically, an object of the present invention is to provide a method for effectively producing a modified physiologically active peptide or protein having a high quality by producing a peptide fragment containing a modified site (modified-component) using a chemical synthesis method, producing a peptide fragment containing no modified part (non-modified component) using a genetic recombination method, and condensing them. As described above, these respective peptide fragments (modified component and non-modified component) may be either of an N-terminal side fragment or a C-terminal side fragment, or may have a plurality of modified components. A production method can be appropriately designed depending on a desired peptide or protein. Another objects of the present invention are to provide a method for producing a protected peptide fragment (modified component) suitable for condensation reaction under mild condition not influencing on a structure of the modified site, and to provide a method for producing a protected peptide fragment (modified component) suitable for condensation with a protected peptide fragment (non-modified component). Yet another object of the present invention is to provide a method for producing a modified physiologically active peptide or protein, which is highly safe enough to be used as a medicament. In particular, an object of the present invention is to provide an industrial method for producing a ghrelin and a ghrelin derivative in a simple and effective manner.

The present inventors have improved a method for synthesizing a peptide fragment containing an amino acid which is modified by an acyl group in ghrelin or a derivative thereof (modified component), using ghrelin as a material, and have established a method by which a peptide fragment (modified component) can be produced in more simple and efficient manner. That is, the present inventors have found a method in which a peptide main chain sequence of a peptide fragment (modified component) is constructed on a weak acid-cleavable resin such as a 2-chlorotrityl resin, etc., and then said peptide is, after selective modification of the residue, treated with a weak acid such as acetic acid, whereby a protected and modified peptide can be cleaved from the solid phase resin. As a prior art, there is known a method in which a modified group is introduced on a resin such as a Wang resin, which can be excised with trifluoroacetic acid, etc. from a resin, and then a protecting group is eliminated when a peptide is cleaved from a resin. However, in the said method, since an cleaved peptide fragment (modified component) is subsequently subjected to a condensation reaction with another peptide fragment (non-modified component), a protecting group must be introduced again, and thus a method based on the prior art by which a protecting group is also eliminated at the same time with cleavage from a resin is not preferable from a viewpoint of simple and effective production.

Given those factors, the present inventors carried out intensive studies and, as a result, they have developed a method in which a weak acid (including diluted strong acid) which hardly eliminates a protecting group for an amino acid side chain is used to cleave a peptide fragment (modified component) of a resin, while a quaternary ammonium fluoride is used as an effective method to selectively modify a residue by eliminating a protecting group for a specific amino acid side chain on a resin without cleaving a peptide from a resin. Conventionally, among quaternary ammonium fluorides, tetrabutylammonium fluoride (TBAF) has been used as a reagent for cleaving a peptide from a solid phase resin (J. Chem. Soc., Chem. Commun., p. 414–415, 1988, Tetrahedron Letters, vol. 34, p. 7599–7602, 1993). However, the present inventors found that a peptide constructed on a weak acid-cleavable resin is not cleaved from a resin by TBAF treatment. As a result, when TBAF is used, a peptide is not cleaved from a resin and, for this reason, a protecting group for a specific amino acid side chain can be eliminated on a resin and a residue can be selectively modified, and by cleaving a peptide fragment (modified component) from a resin using an weak acid (including diluted strong acid) which hardly eliminates a protecting group for an amino acid side chain, a step of protecting a peptide fragment (modified component) in advance becomes unnecessary for the next step of condensation reaction with a peptide fragment (non-modified component). Consequently, a process of producing a modified physiologically active peptide or protein in more simple and effective way can be obtained.

Further, the present inventors improved a method for preparing a protected peptide fragment of ghrelin (non-modified component), and found a linker sequence which is optimal for mass production of a protected ghrelin (8–28) fragment by a two-step enzyme treatment method. Moreover, the present inventors established a method which can considerably simplify and make effective a step of producing a protected peptide fragment (non-modified component) by purification at pH condition under which a protecting group is not eliminated. That is, the present inventors found out that phenomenon of elimination of a protecting group at the time of preparation of a protected peptide depends on pH and temperature of the aqueous solution, and the elimination of a protecting group can be suppressed by adjusting the pH of the aqueous solution to 4 to 8, thereby a protected peptide (non-modified component) can be effectively prepared.

In addition, the present inventors improved a method of condensing each peptide fragment, and developed a production method by which racemization at activation and condensation of amino-acids can be suppressed, and a ghrelin or a ghrelin derivative with higher quality can be produced in a higher yield. In particular, a method for producing ghrelin using a weak acid-cleavable resin has an advantage that formulation of diketopiperazine formed by a side reaction can be suppressed. That is, since a C-terminal amino-acid residue is 7-positional proline, a side reaction of elimination of diketopiperazine from a resin can be minimized by winding diketopiperazine when the third amino acid (Leu) is condensed with a dipeptide (-Ser-Pro-).

Based on those findings, the present inventors have found that the aforementioned method can be easily applied also to production of physiologically active peptides or proteins having various modified structures in which an acyl group, a phosphate group or a sulfate group, needless to say an alkyl group, is bound to a side chain of an amino acid or a non-amino acid via a glycoside bond, a disulphide bond, an ether bond, a thioether bond, an amide bond or the like, and finally completed the present invention.

Namely, the present invention relates to:

(1) a method for producing a protected peptide fragment containing one or more modified amino acids or non-amino acids represented by the formula 1; -A(R)— (wherein A represents an amino acid or a non-amino acid, and R represents a substituent bound to the side chain of A), which comprises using a weak acid-cleavable resin, (2) the method for producing a peptide fragment according to (1), wherein (a) a peptide fragment having a desired sequence of an amino acid or/and a non-amino acid with a protected side chain is prepared on a weak acid-cleavable resin, (b) a protecting group for the side chain of an amino acid or a non-amino acid A which is to be modified with a substituent R is deprotected without cleaving the peptide fragment from the weak acid-cleavable resin, (c) the deprotected side chain is modified with a substituent R, and (d) the peptide fragment is cleaved from the weak acid-cleavable resin, (3) the method for producing a peptide fragment according to (1) or (2), wherein the protecting group for the side chain of an amino acid or a non-amino acid A is a silyl protecting group, and quaternary ammonium fluoride is used for deprotecting the protecting group, (4) the method for producing a peptide fragment according to (3), wherein the silyl protecting group is t-butyldimethylsilyl (TBDMS), t-butyldiphenylsilyl (TBDPS), triisopropylsilyl (TIPS), triisobutylsilyl (TIBS), t-hexyldimethylsilyl (ThxDMS) or triphenylsilyl (TPS), and the quaternary ammonium fluoride is tetrabutylammonium fluoride (TBAF), tetraethylammonium fluoride (TEF) or ammonium fluoride, (5) the method for producing a peptide fragment according to any one of the above (1) to (4), wherein A is serine, threonine, cysteine, homocysteine, lysine, ornithine, glutamic acid, 2-aminoadipic acid, diaminoacetic acid, 2-aminomalonic acid, aspartic acid, tyrosine or asparagine, and R is bound to a side chain of A via an ester bond, an ether bond, a thioether bond, a disulfide bond, an amido bond an O-glycoside bond, an N-glycoside bond or the like, (6) the method for producing a peptide fragment according to the above (5), wherein A is serine or threonine, and R is bound to a side chain of A via an ester bond, (7) the method for producing a peptide fragment according to the above (6), wherein the peptide fragment is ghrelin or a derivative thereof, or a part containing a modified amino acid in the ghrelin or a derivative thereof, (8) a method for producing a modified peptide or protein, which comprises (a) producing a protected peptide fragment containing one or more modified amino acids or non-amino acids represented by the formula 1; -A(R)— (wherein A represents an amino acid or a non-amino acid, and R represents a substituent bound to a side chain of A) using a weak acid-cleavable resin, (b) producing a protected peptide fragment containing no modified amino acid or non-amino-acid, besides the peptide fragment of the (a), and condensing peptide fragments produced in the (a) and (b), (9) the method for producing a modified peptide or protein according to the above (8), wherein the protected peptide fragment containing one or more modified amino-acids or non-amino-acids is produced by the method described in any one of (2) to (4),

(10) the method for producing a modified peptide or protein according to the above (8) or (9), wherein A is serine, threonine, cysteine, homocysteine, lysine, ornithine, glutamic acid, 2-aminoadipic acid, diaminoacetic acid, 2-aminomalonic acid, aspartic acid, tyrosine or asparagine, and R is bound to a side chain of A via an ester bond, an ether bond, a thioether bond, a disulfide bond, an amido bond, an O-glycoside bond or a N-glycoside bond,

(11) the method for producing a modified peptide or protein according to the above (10), wherein A is serine or threonine, and R is bound to a side chain of A via an ester bond,

(12) the method for producing a modified peptide or protein according to the above (11), wherein the modified peptide or protein is ghrelin or a derivative thereof,

(13) the method for producing a modified peptide or protein according to anyone of the above (8) to (12), wherein condensation of peptide fragments is performed by using a condensing agent,

(14) the method for producing a modified peptide or protein according to the above (13), wherein the condensing agent is 2-(1-hydrobenzotriazol-1-yl)-1,1,3,3-tetramethyluronium hexafluorophosphate (HBTU), 2-(1-hydrobenzotriazol-1-yl)-1,1,3,3-tetramethyluronium tetrafluoroborate (TBTU), diphenylphosphorylazide (DPPA), diphenylphosphorocyanidate (DEPC), diisopropylcarbodiimide (DIPC), dicyclohexylcarbodiimide (DCC) or 1-ethyl-3-(3-dimethylaminopropyl)carbodiimide (EDC),

(15) the method for producing a modified peptide or protein according to the above (13), wherein the condensing agent is diisopropylcarbodiimide (DIPC), dicyclohexylcarbodiimide (DCC) or 1-ehtyl-3-(3-dimethylaminopropyl)

carbodiimide (EDC), and condensation of peptide fragments using the aforementioned condensing agent is performed in the presence of 1-hydroxybenzotriazole (HOBt), 1-hydroxysuccinimide (HOSu) or 3,4-dihydro-3-hydroxy-4-oxo-benzotriazine (HOOBt).

More specifically, the present invention relates to, in a process of producing a modified peptide or protein by condensation of fragments, (a) a method for producing a modified physiologically active peptide or protein, which comprises synthesizing a peptide fragment containing a modified group using a weak acid-cleavable resin such as 2-chlorotrityl resin, (b) a method for producing a physiologically active peptide or protein having modification, particularly ghrelin or a ghrelin derivative, which comprises producing a peptide fragment containing an acyl group, a sulfate group, etc. which are easily eliminated with an acid, using a weak acid-cleavable resin such as 2-chlorotrityl resin, (c) a method for producing ghrelin or a ghrelin derivative, which comprises suppressing racemization of a constituent amino acid with the mediation of proline to a C-terminal resin of a N-terminal side fragment to be activated, when a peptide fragment containing modification (modified component) and a peptide fragment containing no modification (non-modified component) are condensed, and (d) a condensing agent which is remarkably appropriate for producing ghrelin or a ghrelin derivative.

Further, the present invention relates to:

(1) a method for producing a protected peptide fragment containing one or more modified amino acids or non-amino acids, which comprises preparing, on a weak acid-cleavable resin, a peptide fragment which has a desired sequence comprising amino acids or/and non-amino acids, at least one amino acid or non-amino acid of them being a modified amino acid or non-amino acid, represented by the formula 1; -A(R)— (wherein, A represents an amino acid or a non-amino acid, and R represents a substituent bound to a side chain of A which is introduced for modification), and in which one or more reactive functional groups which may cause an undesirable side reaction in preparation of a peptide fragment, selected from the group consisting of a hydroxy group, an amino group, a guanidino group, imidazolyl group, an indolyl group, a mercapto group and a carboxyl group, in a side chain of an amino acid or a non-amino acid, are protected with a protecting group, and cleaving the peptide fragment from the weak acid-cleavable resin under weak acidic conditions without elimination of the protecting group in the peptide fragment, (2) the method for producing a peptide fragment according to the above (1), which comprises (a) preparing, on a weak acid-cleavable resin, a peptide fragment having a desired sequence comprising amino acids or/and non-amino acids, in which one or more reactive functional groups which may cause an undesirable side reaction in preparation of a peptide fragment, selected from the group consisting of a hydroxy group, an amino group, a guanidino group, imidazolyl group, an indolyl group, a mercapto group and a carboxyl group, in a side chain of an amino acid or a non-amino acid, are protected with a protecting group, (b) deprotecting the protecting group without cleaving the peptide fragment from the weak acid-cleavable resin, when a protecting group is introduced in a reactive functional group in the side chain of an amino acid or a non-amino acid A which is to be modified with a substituent R, (c) modifying the deprotected side chain with a substituent R, and (d) cleaving the peptide fragment from the weak acid-cleavable resin under weak acidic conditions without elimination of the protecting group in the peptide fragment, (3) a method for producing a protected peptide fragment containing one or more modified amino acids or non-amino acids, represented by the formula 1; -A(R)— (wherein A represents an amino acid or a non-amino acid, and R represents a substituent bound to a side chain of A), which comprises (a) producing, on a weak acid-cleavable resin, a peptide fragment having a desired sequence of an amino acid or/and a non-amino acid, and in which one or more reactive substituents selected from the group consisting of a hydroxy group, an amino group, a guanidino group, imidazolyl group, an indolyl group, a mercapto group and a carboxyl group, in a side chain of an amino acid or a non-amino acid, are protected with a protecting group, (b) cleaving the peptide fragment from the weak acidic resin without elimination of a protecting group in the peptide fragment under weak acidic conditions, (c) deprotecting a protecting group for the reactive substituent in the side chain of at least one amino acid or non-amino acid A of the cleaved peptide fragment, and (d) modifying the deprotected side chain with a substituent R, (4) the method for producing a peptide fragment according to the above (2) or (3), wherein a protecting group for a reactive substituent in a side chain of an amino acid or a non-amino acid A which is to be modified by a substituent R is a silyl protecting group, and a quaternary ammonium fluoride is used for deprotecting the protecting group, (5) the method for producing a peptide fragment according to the above (4), wherein the silyl protecting group is t-butyldimethylsilyl (TBDMS), t-butyldiphenylsilyl (TBDPS), triisopropylsilyl (TIPS), triisobutylsilyl (TIBS), t-hexyldimethylsilyl (ThxDMS) ortriphenylsilyl (TPS), and the quaternary ammonium fluoride is tetrabutylammonium fluoride (TBAF), tetraethylammonium fluoride (TEF) or ammonium fluoride, (6) the method for producing a peptide fragment according to anyone of the above (1) to (5), wherein A is serine, threonine, cysteine, homocysteine, lysine, ornithine, glutamic acid, 2-aminoadipic acid, diaminoacetic acid, 2-aminomalonic acid, aspartic acid, tyrosine or asparagine, and R is bound to a reactive functional group in the side chain of A via an ester bond, an ether bond, a thioether bond, a disulfide bond, an amido bond, an O-glycoside bond or an N-glycoside bond, (7) the method for producing a peptide fragment according to the above (6), wherein A is serine or threonine, and R is bound to a hydroxy group in the side chain of A via an ester bond, (8) the method for producing a peptide fragment according to the above (7), wherein the peptide fragment is ghrelin or a derivative thereof, or a peptide fragment containing a modified amino acid in the ghrelin or a derivative thereof, (9) a method for producing a modified peptide or protein, which comprises (a) preparing a protected peptide fragment containing one or more modified amino acids or non-amino acids by the method described in any one of (1) to (8), (b) preparing a peptide fragment containing no modified amino acid or non-amino acid, and in which one or more reactive functional groups which may cause an undesirable side reaction, selected from the group consisting of a hydroxy group, an amino group, a guanidino group, imidazolyl group, an indolyl group, a mercapto group and a carboxyl group, in the side chain of an amino acid or a non-amino acid, are protected, besides the peptide fragment of the (a), and condensing peptide fragments prepared in the (a) and (b),

(10) the method for producing a modified peptide or protein according to the above (9), wherein condensation of the peptide fragments is performed by using a condensing agent,

(11) the method for producing a modified peptide or protein according to the above (10), wherein the condensing agent is 2-(1-hydrobenzotriazol-1-yl)-1,1,3,3-tetramethyluronium hexafluorophosphate (HBTU), 2-(1-hydrobenzotriazol-1-yl)-1,1,3,3-tetramethyluronium tetrafluoroborate (TBTU), diphenylphosphorylazide (DPPA), diphenylphosphorocyanidate (DEPC), diisopropylcarbodiimide (DIPC), dicyclohexylcarbodiimide (DCC) or 1-ethyl-3-(3-dimethylaminopropyl)carbodiimide (EDC),

(12) the method for producing a modified peptide or protein according to the above (10), wherein the condensing agent is diisopropylcarbodiimide (DIPC), dicyclohexylcarbodiimide (DCC) or 1-ethyl-3-(3-dimethylaminopropyl)carbodiimide (EDC), and condensation of the peptide fragments (a) and (b) using the condensing agent is performed in the presence of 1-hydroxybenzotriazole (HOBt), 1-hydroxysuccinimide (HOSu) or 3,4-dihydro-3-hydroxy-4-oxobenzotriazine (HOOBt),

(13) the method for producing a modified peptide or protein according to any one of the above (9) to (12), which comprises producing a protected peptide fragment containing no modified amino acid or non-amino acid, by an enzymatic method or/and a genetic recombination method,

(14) the method for producing a modified peptide or protein according to the above (13), wherein the protected peptide fragment containing no modified amino acid or non-amino acid is produced by a method comprising;

step (1); a step of culturing a cell transformed with an expression vector having one of a nucleotide sequence encoding a peptide having an amino acid sequence of the peptide fragment (hereinafter, referred to as desired peptide in the present item) or a nucleotide sequence encoding a fusion protein optionally with a protective peptide added to the desired peptide via a linker sequence, and collecting the desired peptide or the fusion protein from the culture;

step (2); a step of cleaving and separating the protective peptide and, optionally, a linker sequence and the desired peptide from the resulting fusion protein, and optionally further purifying the desired peptide when the fusion protein is collected in the step (1); and step (3); a step of protecting, with a protecting group, one or more reactive functional groups which may cause an undesirable side reaction, selected from the group consisting of a hydroxy group, an amino group, a guanidino group, imidazolyl group, an indolyl group, a mercapto group and a carboxyl group, in the side chain of the desired peptide obtained in the step (1) or the step (2),

(15) the method for producing a modified peptide or protein according to the above (14), wherein cleavage and separation of the protective peptide and, optionally, the linker sequence and the desired peptide in the step (2) is performed at two steps using an OmpT protease or a derivative thereof and a Kex2 protease or a derivative thereof,

(16) the method for producing a modified peptide or protein according to the above (14) or (15), wherein the linker sequence is a sequence set forth in SEQ ID NO: 27,

(17) the method for producing a modified peptide or protein according to any one of the above (13) to (16), wherein the peptide fragment is a peptide fragment containing no modified amino acid or non-amino acid in ghrelin or a derivative thereof,

(18) the method for producing a modified peptide or protein according to any one of the above (13) to (17), wherein the protected peptide fragment containing no amino acid or non-amino acid is purified and stored in a solution having a pH of 4 to 8,

(19) the method for producing a modified peptide or protein according to any one of the above (13) to (18), wherein the protecting group is a Boc group,

(20) a method for producing a protected peptide fragment containing no modified amino acid or non-amino acid, which comprises producing the peptide fragment by a method comprising:

step(1); a step of culturing a cell transformed with an expression vector having one of a nucleotide sequence encoding a peptide having the desired amino acid sequence (hereinafter, referred to as desired peptide in the present item) or a nucleotide sequence encoding a fusion protein optionally with a protective peptide added to the desired peptide via a linker sequence, and collecting the desired peptide or the fusion protein from the culture;

step (2); a step of cleaving and separating the protective peptide and, optionally, the linker sequence and the desired peptide from the resulting fusion protein and, optionally further purifying it, when the fusion protein is collected in the step (1);

step (3); a step of protecting, with a protecting group, one or more reactive substituents which may cause an undesirable side reaction, selected from the group consisting of a hydroxy group, an amino group, a guanidino group, imidazolyl group, an indolyl group, a mercapto group and a carboxyl group, in a side chain of the desired peptide obtained in the step (1) or (2); and step (4); a step of purifying and storing the protected desired peptide obtained in the step (3) in a solution having a pH of 4 to 8,

(21) the method for producing a protected peptide fragment containing no modified amino acid or non-amino acid according to the above (20), wherein the protecting group is a Boc group,

(22) the method for producing a protected peptide fragment containing no modified amino acid or non-amino acid according to the above (20) or (21), wherein cleavage and separation of the protective peptide and, optionally, the linker sequence and the desired peptide in the step (2) is performed at two steps using an OmpT protease or a derivative thereof and a Kex2 protease or a derivative thereof,

(23) the method for producing a protected peptide fragment containing no modified amino acid or non-amino acid according to any one of the above (20) to (22), wherein the linker sequence is a sequence set forth in SEQ ID NO:27,

(24) the method for producing a modified peptide or protein according to any one of the above (20) to (23), wherein the peptide fragment is a peptide fragment containing no modified amino acid or non-amino acid in ghrelin or a derivative thereof.

BRIEF EXPLANATION OF THE DRAWINGS

FIG. 1A shows a total synthetic oligo-DNA and an amino acid sequence of hGhrelin (8–28). FIG. 1B shows an amino acid sequence of hGhrelin (8–28) fusion protein which is expressed by plasmid p117 8–28oRR.

FIG. 6A shows results of HPLC analysis after Kex2 enzyme reaction of PR-hGhrelin (8–28). FIG. 6B shows results of HPLC analysis after a Kex2 enzyme reaction of RR-hGhrelin (8–28). FIG. 6C shows results of HPLC analysis after Kex2 enzyme reaction of KR-hGhrelin (8–28). Peak a) denotes the peak of [Lys$^{16,19,20,24}$(Boc)]hGhrelin(8–28) containing a linker sequence. Peak b) denotes the peak of [Lys$^{16,19,20,24}$(Boc)]hGhrelin(8–28). Peak c) denotes the peak of [Lys$^{16,19,20,24}$(Boc)]hGhrelin(16–28).

FIG. 7 shows an amino acid sequence of each hGhrelin (8–28) fusion protein prepared for determining an optimal fusion protein for incubation.

FIG. 8A shows the difference in results of incubation between different fusion proteins, and FIG. 8B shows relative ratio of turbidity after crushing of cells to turbidity before crushing of cells of a culture solution using each fusion protein (difference due to fusion proteins).

FIG. 10 shows results of stability assessment of [Lys$^{16,19,20,24}$(Boc)]hGhrelin(8–28).

BEST MODE FOR CARRYING OUT THE INVENTION

Figure 2:
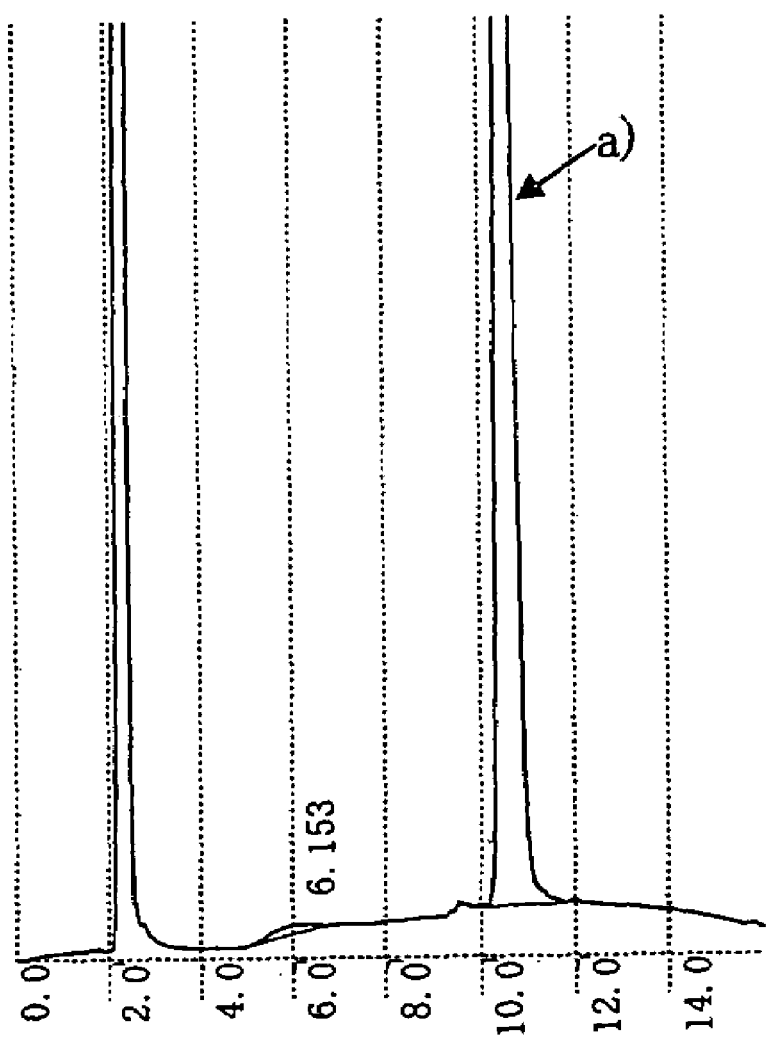
FIG. 2 shows results of HPLC analysis of purified [Lys$^{16, 19, 20, 24}$(Boc)]hGhrelin(8–28). Peak a) denotes the peak of [Lys$^{16,19,20,24}$(Boc)]hGhrelin(8–28).

In explanation of the present invention, the terms used in the present invention are defined as follows:

An "amino acid" refers to a compound having an amino group and a carboxyl group in the same molecule, and includes all amino acids such as a L-amino acid, a D-amino acid, an α-amino acid, a β-amino acid, a γ-amino acid, a natural amino acid, a non-natural amino acid, a synthetic amino acid and the like.

A "natural amino acid" refers to twenty kinds of amino acids encoded by genes.

A "non-natural amino acid" refers to a compound in which an α carbon in an α-amino acid is modified with an arbitrary substituent which is not present in a natural amino acid or a corresponding D-amino acid. That is, when an α-amino acid is expressed by the following formula;

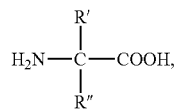

an example of the non-natural amino acid includes a compound having arbitrary substituents which are not present in a natural amino acid or a corresponding D-amino acid, or a hydrogen atom, as substituents represented by R' and R", provided that both of R' and R" are not hydrogen atom.

A "non-amino acid" refers to an analogue of an amino acid comprising one or more atoms selected from the group consisting of C, H, O, N and S, which is not included in a natural amino acid and a non-natural amino acid. Inter alia, a compound having a molecular chain length of a peptide length or a dipeptide length is preferable. For example, $NH_2$—$CH(CH_2OH)$—$CH_3$, $CH_3$—$CH(R_{11})$—$COOH$, $CH_3$—$CH(R_{11})$—$CH_3$, all of which having a peptide length, or $NH_2$—$(CH_2)_3CH(CH_2OH)$—$COOH$, $NH_2$—$(CH_2)_4$—$COOH$, $NH_2$—$C(CH_3)_2$—$(CH_2)_3$—$COOH$, $NH_2$—$CH(CH_3)$—$(CH_2)_2$—$CH(CH_3)$—$COOH$, $NH_2$—$(CH_2)_3CH(CH_2OH)$—$CH_3$, $NH_2$—$(CH_2)_3CH(R_{11})$—$CH_3$, all of which having a dipeptide length, are included in the "non-amino acid" in the present invention. Herein, $R_{11}$ represents a side chain of a natural amino acid. Examples of a "non-amino-acid residue" in a peptide include —NH—CH$(CH_2OH)$—CH$_2$—, —CH$_2$—CH$(R_{11})$—CO—, —CH$_2$—CH$(R_{11})$—CH$_2$—, all of which having a peptide length, and —NH—$(CH_2)_3$CH$(CH_2OH)$—CO—, —NH—$(CH_2)_4$—CO—, —NH—C$(CH_3)_2$—$(CH_2)_3$—CO—, —NH—CH$(CH_3)$—$(CH_2)_2$—CH$(CH_3)$—CO—, —NH—$(CH_2)_3$CH$(CH_2OH)$—CH$_2$—, —NH—$(CH_2)_3$CH$(R_{11})$—CH$_2$—, all of which having a dipeptide length, and there can be a case where a bond with an adjacent amino acid is not a peptide bond.

A "peptide" or a "peptide fragment" refers to a compound in which a plurality of amino acids are linked by a peptide bond. Herein, when a non-amino acid is contained, there is a case where a bond between the non-amino acid and an adjacent amino acid is not a peptide bond. However, a compound in this case is also collectively referred to as a peptide or a peptide fragment.

A "protected peptide fragment" refers to a fragment of a peptide in which one or more reactive substituents selected from the group consisting of a hydroxy group, an amino group, a guanidino group, an imidazolyl group, an indolyl group, a mercapto group and a carboxyl group of the side chain of an amino acid or a non-amino-acid of a peptide fragment, which may cause an undesirable side reaction upon preparation of a peptide fragment or condensation reaction of peptide fragments, are protected with a protecting group. Hereinafter, it is abbreviated as a "protected peptide fragment" in the present specification.

A "modified amino acid or non-amino acid" may be represented by the formula 1; -A(R)—, wherein A represents an amino acid or a non-amino acid, and R represents a substituent bound to a side chain of A, which is introduced for modification.

There is a case where the substituent R is bound to a group formed by removal of a hydrogen atom from a hydroxy group, an amino group, a guanidino group, an imidazolyl group, an indolyl group, a mercapto group or a carboxyl group in the side chain of an amino acid or a non-amino acid, or a case where the substituent R is directly bound to an α-carbon of an amino acid or a non-acid. The substituent R may be a modified side chain of an amino acid or a non-amino acid.

There is no limitation to the substituent R. Examples of R include a group represented by the formula 2; —$(CH_2)_n$—P-Q (wherein n denotes an integer of 1 to 10, P denotes —CO—, —SO$_2$—, —CO—O—, —O—CO—, —O—, —CO—S—, —S—CO—, —CS—S—, —S—CS—, —S—, —CO—NH—, —NH—CO—, —CO—NH—CO—, —CS—NH—CS—, —S—S—, —CS—NH— or —NH—CS—, and Q denotes a hydrogen atom, or an alkyl group having 1 to 35 carbon atoms or preferably 1 to 20 carbon atoms, an aryl group having 6 to 20 carbon atoms or a aralkyl group having 7 to 16 carbon atoms), a group represented by the formula 3; —P-Q (wherein P and Q have the same meaning as defined above), and a group represented by the formula 4; -Q (wherein Q has the same meaning as defined above). Inter alia, when the substituent R is directly bound to an amino acid or a non-amino acid, a preferable example of the R includes a group in which an alkyl group having 1 to 35 carbon atoms or preferably 1 to 20 carbon atoms, an aryl group having 6 to 20 carbon atoms or an aralkyl group having 7 to 16 carbon atoms, is bound with a bond selected from the group consisting of ester, ether, thioester, thioether, amido and carbamido bonds optionally via an alkyl group having one or more carbon atoms. When the substituent R is directly bound to an α carbon of an amino acid or a non-amino acid, the substituent R does not include a substituent bound to an α carbon in a natural amino acid. When the substituent R is bound to a reactive substituent in a side chain of an amino acid or a non-amino acid, the substituent R is preferably a group represented by the formula 4; -Q, wherein Q has the same meaning as defined above).

Herein, the "alkyl group" refers to a cyclic, straight or branched alkyl group, and examples thereof include a methyl group, an ethyl group, a propyl group, an isopropyl group, a cyclopropyl group, a butyl group, a sec-butyl group, an isobutyl group, a tert-butyl group, a cyclobutyl group, a pentyl group, an isopentyl group, a tert-pentyl group, a neopentyl group, a cyclopentyl group, a hexyl group, an isohexyl group, a cyclohexyl group, a 3,3-dimethylbutyl group, a heptyl group, a 1-propylbutyl group, an octyl group, a nonyl group, a decyl group, an undecyl group, a dodecyl group, a tridecyl group, a tetradecyl group, a pentadecyl group and the like. These may partially contain an unsaturated carbon bond, and the number of carbons is 1 to 35, preferably 1 to 20, more preferably 1 to 10.

Examples of the "aryl group" include a phenyl group, a 1- or 2-naphthyl group, a biphenyl, 1-, 2- or 9-anthryl group, a 1-, 2-, 3-, 4- or 9-phenanthryl group, an acenaphthyl group, an anthracenyl group, an azulenyl group and the like. The number of carbons is 6 to 20, preferably 6 to 15.

Examples of the "aralkyl group" include benzyl, p-methoxybenzyl, 3,4-dimethoxybenzyl, o-nitrobenzyl, p-nitrobenzyl, benzhydryl, trityl group and the like. The number of carbons is preferably 7 to 16.

Further, these alkyl group, aryl group and aralkyl group may have a substituent which is normally used in the art at an chemically acceptable position and number.

As the "modified amino acid or non-amino acid", the preferred is the case where the amino acid or the non-amino acid A is serine, threonine, cysteine, homocysteine, lysine, ornithine, glutamic acid, 2-amino adipic acid, a diaminoacetic acid, 2-aminomalonic acid, aspartic acid, tyrosine or asparagine, and a substituent R is a group represented by the formula 5; —(CH$_2$)$_n$—P$^1$-Q$^1$ (wherein n has the same meaning as defined above; P$^1$ represents an ester bond, an ether bond, a thioether bond, a disulfide bond, an amido bond, an O-glycoside bond or a N-glycoside bond; and Q$^1$ has the same meaning as that of the aforementioned Q).

Specifically, for example, when an amino acid A is serine, threonine, tyrosine or oxyproline, since the amino acid has a hydroxy group in the side chain, examples of the "modified amino acid" include serine, threonine, tyrosine and oxyproline in which a hydroxy group in the side chain is etherized or esterified. When an amino acid A is cysteine, since the amino acid has a mercapto group in the side chain, examples of the "modified amino acid" include cysteine in which a mercapto group in the side chain is thioetherized, thioesterified or disulfidized. When an amino acid A is lysine, arginine or 2,3-diaminopropionic acid, since the amino acid has an amino group in a side chain, examples of the "modified amino acid" include lysine, arginine or 2,3-diaminopropionic acid in which an amino group in a side chain is amidated, thioamidated, carbamidized, thiocarbamidized or alkylated. When an amino acid A is histidine, tryptophan, proline or oxyproline, since the amino acid has an amino group in the side chain, examples of the "modified amino acid" include histidine, tryptophan, proline or oxyproline in which an amino group in the side chain is amidated, thioamidated, iminoetherized, iminothioetherized or alkylated.

Inter alia, as the "modified amino acid or non-amino acid", serine or threonine in which a hydroxy group in the side chain is esterified is preferable.

Further, when a side chain of an amino acid or a non-amino acid A contains —OH, —SH, —NH— or —NH.sub.2, more preferable examples of the substituent R include a group formed by acylation of them. Examples of the acyl group therefor include a group formed by removal of a hydroxy group from organic carboxylic acid, organic sulfonic acid or organic phosphate compound. More specific example of the organic carboxylic acid includes a fatty acid, and the number of carbons is preferably 2 to 35, more preferably 6 to 18, most preferably 8 to 16. Examples of the fatty acid include saturated fatty acids such as caprylic acid, capric acid, lauric acid, butyric acid, caproic acid, undecylic acid, palmitic acid, decanoic acid, nonadecanoic acid, behenic acid, montanoic acid, lacceric acid, etc., and unsaturated fatty acids such as acrylic acid, oleic acid, linoleic acid, linolenic acid, stearic acid, etc. The unsaturated fatty acid may be monoene or polyene. Inter alia, the preferable examples include octanoic acid (preferably, caprylic acid), decanoic acid (preferably, capric acid), dodecanoic acid (preferably lauric acid), etc. With regard to the organic sulfonic acid or organic phosphoric acid compound, the number of carbons is preferably 2 to 35.

The "modified peptide or protein" refers to a peptide or a protein containing one or more amino acids or non-amino acids which have undergone the aforementioned modification in a peptide or a protein.

"Ghrelin" is endogenous growth hormone secretagogue (GHS), and has activity of increasing the calcium ion concentration in a cell and activity of inducing secretion of growth hormone. Inter alia, ghrelin derived from human, rat, mouse, pig, fowl, eel, cow, horse, sheep, frog, trout or dog is preferable. More specific examples of "ghrelin" include a protein which has an amino acid sequence described in any one of SEQ ID NOS: 1 to 21, and in which a hydrogen atom of the side chain hydroxy group of 3-positional serine or threonine is substituted with any one of a n-octanoyl group, a butanoyl group, a hexanoyl group, a decanoyl group or a dodecanoyl group; or a protein having activity of increasing the calcium ion concentration in a cell, which has an amino acid sequence in which 1 to 10, preferably 1 to a few amino acids are substituted, added or deleted in a part other than the sequence of N-terminal first to forth amino acids, in an amino acid sequence described in any one of SEQ ID NOS: 1 to 21, and in which a hydrogen atom of the side chain hydroxy group of 3-positional serine or threonine is substituted with any one of a n-octanoyl group, a butanoyl group, a hexanoyl group, a decanoyl group or a dodecanoyl group.

Examples of the "ghrelin derivative" include a peptide having activity of increasing the calcium ion concentration in a cell and containing one or more modified amino acids or non-amino acids, or a pharmaceutically acceptable salt thereof. Inter alia, a peptide having at least a sequence of between the amino terminus and the 4$^{th}$ amino acid, preferably a sequence of between the amino terminus and the $5^{th}$ amino acid, preferably a sequence of between the amino terminus and the $6^{th}$ amino acid, preferably a sequence of between the amino terminus and the $7^{th}$ amino acid, preferably a sequence of between the amino terminus and the $8^{th}$ amino acid, preferably a sequence of between the amino terminus and the $9^{th}$ amino acid, preferably a sequence of between the amino terminus and the $10^{th}$ amino acid in an amino acid sequence described in SEQ ID NO: 1, or a pharmaceutically acceptable salt thereof is preferable. Further, a peptide containing an amino acid sequence in which at least one amino acid, preferably 1 to 10 amino acids, more preferably 1 to several amino acids are deleted, substituted and/or added, in apart other than a sequence of between the amino terminus and the $4^{th}$ amino acid, preferably a sequence of between the amino terminus and the $5^{th}$ amino acid, preferably a sequence of between the amino terminus and the $6^{th}$ amino acid, preferably a sequence of between the amino terminus and the $7^{th}$ amino acids, preferably a sequence of between the amino terminus and the $8^{th}$ amino acid, preferably a sequence of between the amino terminus and the $9^{th}$ amino acid, preferably a sequence of between the amino terminus and the $10^{th}$ amino acid, in an amino acid sequence described in SEQ ID NOS: 1 to 21, or a pharmaceutically acceptable salt thereof is preferable. Inter alia, among all peptides or pharmaceutically acceptable salts thereof in the aforementioned embodiments, the more preferred is an amino acid or a non-amino acid in which the amino acids between the amino terminus and the $2^{th}$ or $3^{rd}$ amino acid, more preferably between the amino terminus and $3^{rd}$ amino acid are modified.

Moreover, a preferable embodiment includes a peptide in which a sequence of between the amino terminus and the $4^{th}$ amino acid is substituted with a peptide fragment represented by the formula 6; A-B-C-D- (wherein A denotes an amino acid, a non-amino acid or absent, B denotes an amino acid, a non-amino acid or absent, provided that, a molecular chain length of A+B is a dipeptide length, and C and D may be independently (a) a modified amino acid, (b) an amino acid having a hydrophobic side chain or (c) an amino acid having a basic side chain), in an amino acid sequence described in SEQ ID NOS: 1 to 21 or in an amino acid sequence in which at least one amino acid, preferably 1 to 10 amino acids, more preferably 1 to several amino acids are deleted, substituted and/or added in the said amino acid sequence, or a pharmaceutically acceptable salt thereof. Examples of the "amino acid having a hydrophobic side chain" include leucine, valine, norleucine, homoleucine, homoisoleucine, naphthylalanines, tryptophan, phenylalanine, cyclohexylalanine, etc. or N-methylamino acid or D-amino acid thereof. Examples of the "amino acid having a basic side chain" include lysine, arginine or histidine, or D-amino acid thereof. Inter alia, the preferred is an amino acid in which C is an amino acid which has undergone the aforementioned modification, and D is an amino acid having a hydrophobic side chain in the aforementioned formula 6.

Instead of the aforementioned peptide fragment represented by the formula 6; A-B-C-D-, a peptide fragment represented by the formula 7; $A^1$-$B^1$-$C^1$-$D^1$- (wherein $A^1$ denotes an amino acid or a non-amino acid, preferably a natural amino acid or a D-amino acid thereof; at least one of $B^1$ or $C^1$ is a modified amino acid or non-amino acid and, when only one of $B^1$ or $C^1$ is a modified amino acid or non-amino acid, the other is an unmodified amino acid or non-amino acid, preferably a natural amino acid or a D-amino acid thereof; a molecular chain length of $A^1$+$B^1$ is a dipeptide length; and $D^1$ denotes an amino acid having a hydrophobic side chain or an amino acid having a basic side chain) may be used.

Moreover, in place of the aforementioned peptide fragment represented by the formula 6; A-B-C-D-, a peptide fragment represented by the formula 8; $B^2$-$C^2$-$D^2$- (wherein $B^2$ is a non-amino acid having a dipeptide length, $C^2$ is a modified amino acid or non-amino acid, and $D^2$ denotes an amino acid having a hydrophobic side chain or an amino acid having basic side chain) may be used.

Further, with regard to the "ghrelin derivative", the amino terminus or the carboxyl terminus of a peptide or a pharmaceutically acceptable salt in the aforementioned embodiment may be modified. Specifically, it is preferable that a basic amino acid is further bound to a carboxyl terminus of a peptide or a pharmaceutically acceptable salt thereof in the aforementioned embodiment. In addition, it is preferable that an amino terminus of a peptide or a pharmaceutically acceptable salt thereof in the aforementioned embodiment is modified with a saturated or unsaturated alkyl group or an acyl group having one or more carbon atoms and/or OH of a carboxyl group of the carboxyl terminus is converted into OZ or NR2R3 (wherein Z is a pharmaceutically acceptable cation or a lower branched or non-branched alkyl group, and R2 and R3 each independently represents a group selected from the group consisting of a hydrogen atom and a lower branched or straight alkyl group having 1 to 6 carbon atoms). Further, these modifications may be combined.

A method for producing a modified peptide or protein of the present invention comprises three steps of (a) producing a protected peptide fragment containing one or more modified amino acids or non-amino acids using a weak acid-cleavable resin, (b) producing separately a protected peptide fragment containing no modified amino acid or non-amino acid, besides the protected peptide fragment of (a), and (c) condensing the protected peptide fragments produced in the (a) and (b).

Each step in production of a modified peptide or protein will be more specifically described below.

Since a modified peptide or protein obtained by the production method of the present invention, or a fragment thereof is peptidic, it can be synthesized by known per se peptide synthesis methods. Herein, a modified peptide or protein, or a fragment thereof includes compounds in which these reactive functional groups are protected with a protecting group. A peptide synthesis method may be, for example, according to either of a solid phase synthesis method and a liquid phase synthesis method. That is, a desired peptide can be produced by condensing a partial peptide or amino acids which can constitute a crude modified peptide or protein, or a fragment thereof, with a remaining part, followed by elimination of a protecting group when a product has a protecting group. Examples of the known condensing method and a elimination method of a protecting group include methods described in the following publications 1 to 3.

1. Nobuo Izumiya et al. "Basic and Experiment of Peptide Synthesis" published by Maruzen Co., Ltd. (1985)

2. Haruaki Yajima and Shunpei Sakakibara "Biochemistry Experimental Course 1, Protein Chemistry IV" edited by of The Japanese Biochemical Society, published by Tokyo Kagaku Dozin Co., Ltd. (1977)

3. "Development of Medicament, Sequel, vol. 14, Peptide Synthesis" supervised by Haruaki Yajima published by Hirokawashoten.

A step of producing a protected peptide fragment containing one or more modified amino acids or non-amino acids comprises using solid phase chemical synthesis of extending a peptide chain on a weak acid-cleavable resin. More specifically, a desired protected peptide fragment can be obtained by condensing amino acids or non-amino acids in which an α-amino group and reactive functional groups in the side chain which may cause an undesirable side reaction upon preparation of a peptide fragment are appropriately protected on a weak acid-cleavable resin according to a sequence of a desired peptide fragment in accordance with known per se various condensing methods, and cleaving the produced protected peptide fragment from the weak acid-cleavable resin without elimination of a protecting group.

The weak acid-cleavable resin refers to a resin used in peptide synthesis, which can cleave a peptide fragment prepared on a resin from the resin under weak acidic conditions. For example, as the weak acid-cleavable resin, the preferred is a resin which can cleave, from the resin, a peptide fragment prepared on the resin, in a solution containing one or more compounds comprising the group consisting of carboxylic acids such as acetic acid, trifluoroacetic acid and formic acid, and fluorinated alcohols such as trifluoroethanol and hexafluoroisopropanol. More specific examples of the weak acid-cleavable resin include trityl-based resins such as 2-chlorotrityl resin, trityl resin, 4-methyltrityl resin, 4-methoxytrityl resin, Rink Amide Barlos resin, etc., and Sieber Amide resin and the like.

A protecting group for an α-amino group and a reactive functional group in a side chain (hereinafter, simply referred to as side chain functional group) is not particularly limited. Examples of a protecting group for an α-amino group include an alkoxycarbonyl group optionally having a substituent such as t-butoxycarbonyl (Boc), trichloroethyloxycarbonyl, t-amyloxycarbonyl, 9-fluorenylmethoxycarbonyl (Fmoc), methylsulfonylethoxycarbonyl, trichloroethoxycarbonyl, 2-(trimethylsilyl)ethoxycarbonyl and pyridine-4-methoxycarbonyl; a cycloalkyloxycarbonyl group optionally having a substituent such as cycloheptyloxycarbonyl and cyclohexyloxycarbonyl; an aralkyloxycarbonyl group such as benzyloxycarbonyl (Z), p-methoxybenzyloxycarbonyl (pMZ), p-chlorobenzyloxycarbonyl (Cl-Z), p-bromobenzyloxycarbonyl (Br-Z), p-nitrobenzyloxycarbonyl, adamantyloxycarbonyl, 2-phenylisopropyloxycarbonyl, p-methylphenylisopropyloxycarbonyl, p-biphenylisopropyloxycarbonyl, and 3,5-dimethoxy-α, α-dimethylbenzyloxycarbonyl; an aralkyl group optionally having a substituent such as benzyl (Bzl), benzhydryl, and trityl; an acyl group optionally having a substituent such as trifluoroacetyl, phthaloyl, formyl, benzenesulfonyl, p-toluenesulfonyl (Ts), o-nitrophenylsulfenyl, 2,4-dinitrophenylsulfenyl, and 3-nitro-2-pyridylsulfenyl; dithiasuccinoyl, 2-nitrophenylthio, diphenylphosphinyl, diphenylphosphinothioyl, and dimethylphosphinothioyl.

A hydroxy group of serine and the like can be protected with a lower alkanoyl group having 1 to 6 carbon atoms such as an acetyl group, an aroyl group such as a benzoyl group, and a group derived from carbonic acid such as a benzyloxycarbonyl group, an ethoxycarbonyl group etc.

A guadinino group of arginine can be protected, for example, with a nitro group, a Z group, a Ts group, a p-methoxybenzenesulfonyl group (Mbs), a 4-methoxy-2,6-dimethylbenzenesulfonyl group (Mds), a 4-methoxy-2,3,6-trimethylbenzenesulfonyl group (Mtr), a mesytilene-2-sulfonyl group (Mts), a 2,3,4,5,6-pentamethylbenzenesulfonyl group (Pme), a 2,4,6-trimethoxybenzenesulfonyl group (Mtb), a 2,2,5,7,8-pentamethylchroman-6-sulfonyl group (Pmc), or a 2,2,4,6,7-pentamethyl-dihydrobenzofuran-5-sulfonyl group (Pbf).

In addition, a mercapto group of cysteine can be protected, for example, with a trityl group, an acetamidomethyl (Acm) group, a tert-butyl group, a benzyl group, a p-methylbenzyl group, a p-methoxybenzyl group, a 3-nitro-2-pyridinesulfenyl group, or a butylthio group.

As a protecting group for an imidazolyl group of histidine, there are used, for example, a Boc group, a trityl (Trt) group, a Ts group, a 4-methoxy-2,3,6-trimethylbenzenesulfonyl group, a2,4-dinitrophenol (DNP) group, abenzyloxymethyl (Bom) group, a t-butoxymethyl (Bum) group, and a Fmoc group. In addition, an indolyl group of tryptophan can be protected, for example, with a formyl group, a Z group, a 2,4-dichlorobenzyloxycarbonyl group, a trichloroethyloxycarbonyl group, a 4-methoxy-2,3,6-trimethylbenzenesulfonyl group, or a 2,4,6-trimethoxybenzenesulfonyl group.

A condensation reaction by a solid phase synthesis may be performed by any of a stepwise elongation method of condensing amino acids one by one on a weak acid-cleavable resin, a fragment condensation of condensing a peptide fragment composed of two or more amino acids, and a combination of them. The peptide fragment composed of two or more amino acids can be produced from respective amino acids by the conventional liquid or solid phase synthesis.

First, an amino acid or a non-amino acid having the aforementioned α-amino group and an appropriately protected functional group in the side chain (hereinafter, abbreviated as protected amino acid, unless otherwise indicated) are activated, and a weak acid-cleavable resin is condensed with the activated protected amino acid. In the condensation, a solvent used for activation of a protected amino acid or condensation with the resin is appropriately selected from the solvents known in a peptide condensation method. For example, acid amides such as N,N-dimethylformamide, N,N-dimethylacetamide, and N-methylpyrrolidone; halogenated hydrocarbons such as methylene chloride, and chloroform; alcohols such as trifluoroethanol and phenol; sulfoxides such as dimethyl sulfoxide; esters such as pyridine, dioxane, and tetrahydrofuran; nitriles such as acetonitrile, and propionitrile; esters such as methyl acetate, and ethyl acetate, and an appropriate mixture of them are used. A reaction temperature may be the same as the reaction temperature of a peptide bond forming reaction, and is usually appropriately selected from a range of around −20° C. to 50° C. An activated protected amino acid is usually used at a 1- to 4-fold excessive amount. When the condensation is found to be insufficient as a result of a test using a ninhydrin reaction, sufficient condensation can be performed by repeating a condensation reaction without elimination of a protecting group. When sufficient condensation is not attained even when a reaction is repeated, it is possible to have no influence on a subsequent reaction by acetylating an unreacted protected amino acid using acetic anhydride or acetylimidazole.

Then, a protected amino acid is condensed with a protected amino acid condensed with a weak acid-cleavable resin according to a desired sequence. A reaction of condensing each protected amino acid can be performed by the conventional method such as a C-terminal activating method and a coupling method using a coupling reagent. The C-terminal activating method includes an active ester method, and a symmetric acid anhydride method. Examples of such an active ester used in the active ester method include alkyl esters such as cyanomethyl ester; phenyl esters such as thiophenyl ester, p-nitrothiophenyl ester, p-methanesulfonylphenyl ester, p-nitrophenyl ester, 2,4-dinitrophenyl ester, 2,4,6-trichlorophenyl ester, and pentachlorophenyl ester; dicarboxylic acid imidoesters such as 1-hydroxysuccinimide (HOSu), N-hydroxyphthalicacidimidoester, and N-hydroxy-5-norbornene-2,3-dicarboxylicacidimide (HONB); hydroxylamine derivatives such as 8-hydroquinoline ester, N-hydroxypiperidine ester, and 2-hydroxypyridine ester.

Examples of the coupling method using a coupling reagent include a carbodiimide method using dicyclohexylcarbodiimide (DCC), and a water-soluble carbodiimide (WSC); a DCC-additive method; a carbonyldimidazole (CDI) method; a method using isooxazolium salt such as a Woodward reagent (N-ethyl-5-phenylisooxazolium-3'-sulfonate) and N-ethyl-2'-hydroxybenzisooxazolium trifluoroborate, 1-ethoxycarbonyl-2-ethoxy-1,2-dihydroxyquinoline (EEDQ), 1-ethoxycarbonyl-2-isobutoxy-1,2-dihydroxyquinoline (IIDQ), benzotriazol-1-yl-oxy-tris(dimethylamino)-phosphonium hexafluorophosphate (BOP), O-benzotriazole-N,N,N',N'-tetramethyl-uronium-hexafluorophosphate (HBTU), O-benzotriazole-N,N,N',N'-tetramethyl-uronium-tetrafluoroborate (TBTU), or diphenylphosphorylazide (DPPA).

The water-soluble carbodiimide (WSC) used in the carbodiimide method includes EDC (1-ethyl-3-(3-dimethylaminopropyl)carbodiimide, N-cyclohexyl-N'-morpholineothylcarbodiimide, and N-cyclohexyl-N'-(N,N-diethylamino)cyclohexylcarbodiimide. The water-soluble carbodiimide may be a salt such as hydrochloride.

In addition, the DCC-additive method includes a DCC-HOSu method, a DCC-HOBt (1-hydroxybenzotriazole) method, a DCC-HONB method, a DCC-ethyl 2-hydroxyimino-2-cyanoacetate method, a WSC-HOSu method, and a WSC-HOBt method.

A preferable condensation reaction includes a carbodiimide method, an active ester method, and a DCC-additive method. A further preferable condensation method includes a method of preventing recemization such as an active ester method, and a DCC-additive method (e.g. DCC-HOBt method, DCC-HOSu method, WSC-HOSu method, WSC-HOBt method etc.).

A desired protected peptide fragment contains one or more modified amino acids or non-amino acids. As a method of inserting a modified amino acid or non-amino acid into a peptide chain, there are the following two methods.

As a first method, there is a method of specifically modifying a side chain of a desired amino acid or non-amino acid in advance, and introducing such the amino acid or non-amino acid (hereinafter, referred to as a residue-specifically modified amino acid or non-amino acid) at the stage of extending a peptide chain. More specifically, a residue-specifically modified amino acid or non-amino acid (including compounds of which α amino group is protected) can be synthesized by the known per se synthesis method. Examples of such a method include esterification, amidation, etherization, acylation, and alkylation, and these are performed by the methods well-known to a person skilled in the art. Further, this can be introduced into a peptide chain by any one of the aforementioned condensation methods. In this case, elimination of a protected peptide fragment from the weak-acid cleavable resin is appropriately selected from conditions described later and, preferably, elimination is appropriately selected from conditions under which a substituent R of a side chain of a desired residue-specifically modified amino acid or non-amino acid is not eliminated.

As a second method, there is a method of preparing a peptide fragment having a desired sequence comprising an amino acid or/and a non-amino acid by the aforementioned method and, thereafter, specifically modifying a side chain of a desired amino acid or a non-amino acid (hereinafter, referred to as a residue-specific modification). The residue-specific modification method is not particularly limited, but the known method may be used. Examples of the method include esterification, amidation, etherization, acylation, and alkylation, and these are performed by the methods well-known to a person skilled in the art. Further, a phosphorylation modifying method includes methods described in Tetrahedron Letters, vol. 41, p. 4457–4461, 2000 or Biopolymers, vol. 60, p. 3–31, 2001. A sugar modifying method includes methods described in Int. J. Peptide Protein Res., vol. 42, p. 165–170, 1993, Science, vol. 291, p. 2344–2350, 2001, or Science, vol. 291, p. 2357–2364, 2001.

Such a method can be classified into the following two methods. That is, when a functional group of a side chain of an amino acid or a non-amino acid to be residue-specifically modified is protected with a protecting group, the method can be roughly classified into the case where, upon deprotection of such protecting group, a protected peptide fragment is cleaved from a resin at the same time, and the case where upon deprotection of such protecting group, a protected peptide fragment is not cleaved from a resin. In the case of the former, a desired peptide fragment can be obtained by protecting a C-terminal carboxyl group with a protecting group, performing residue-specific modification by the known per se synthetic method and, thereafter, deprotecting the C-terminal carboxyl group by appropriately selecting a method from the methods described later. In the case of the latter, residue-specific modification can be performed on a resin by the known per se synthetic method and, thereafter, a desired peptide fragment may be eliminated from a resin by appropriately selecting a method from the methods described later.

In the present invention, a method is most preferable in which a peptide fragment having a desired sequence comprising an amino acid or/and a non-amino acid is prepared by the aforementioned method, thereafter, when a reactive functional group of a side chain of an amino acid or a non-amino acid to be residue-specifically modified is protected with a protecting group, the protecting group is deprotected, residue-specific modification is performed on a resin by the known per se synthetic method and, then, elimination of a protected peptide fragment from the weak acid-cleavable resin described later and, optionally, deprotection of each protecting group are performed.

In the aforementioned method, a protecting group for an amino acid or a non-amino acid to be residue-specifically modified is not particularly limited as far as a protected peptide fragment is not cleaved from a resin upon deprotection of such protecting group, but preferable examples include silyl groups such as a t-butyldimethylsilyl group, and a t-butyldiphenylsilyl group. Upon deprotection of such protecting group, a reagent which can specifically deprotect a protecting group for a side chain functional group of an amino acid or a non-amino acid to be residue-specifically modified without cleaving a protected peptide fragment from a resin is used. Such reagent is appropriately selected depending on a kind of a weak acid-cleavable and the protecting group, and when the protecting group is a silyl group, quaternary ammonium fluoride is preferably used, and tetrabutylammonium fluoride (TBAF) is more preferably used.

If a protecting group is selected as described above, when an N-terminal amino group is deprotected in order to effect condensation for a peptide extension, a protecting group for a side chain functional group of each protected amino acid is not eliminated and a protected peptide fragment is not cleaved from a weak acid-cleavable resin and, when a weak acid-cleavable resin is eliminated from the resulting peptide bound-resin, a protecting group for a side chain functional group of each amino acid residue is not eliminated. Moreover, due to this, production of a byproduct can be suppressed. For this reason, a peptide fragment in which a side chain functional group is protected with a protecting group can be obtained simply at a high purity and high yield. Since this peptide fragment has a protected side chain functional group, it is not necessary to freshly introduce a protecting group, and the fragment can be preferably used as a starting material for the preparation of a desired modified peptide or protein by a liquid phase method in the next step.

Finally, a protected peptide fragment thus obtained is cleaved from a weak acid-cleavable resin. Thereupon, cleavage is performed at weakly acidic conditions under which a protecting group in a protected peptide fragment, that is, a protecting group for a side chain functional group of an amino acid or a non-amino acid is not deprotected. Weakly acidic condition includes condition under which a weak acid-cleavable resin is suspended in a solution containing carboxylic acids such as acetic acid, trifluoroacetic acid and formic acid, and/or fluorinated alcohols such as trifluoroethanol and hexafluoroisopropanol. Specifically, the protected peptide fragment thus obtained can be cleaved from a weak acid-cleavable resin by stirring in the aforementioned solution for a desired time, preferably around 5 minutes to 4 hours, more preferably around 10 minutes to 2 hours. More specifically, cleavage may be according to the known method described in a Barlos et al method (Tetrahedron Lett, Vol. 30, p. 3947, 1989), for example, a method of suspending in a solvent such as 0.5% trifluoroacetic acid/dichloromethane, or acetic acid/trifluoroethanol/dichloromethane=1/2/7, or acetic acid/trifluoroethanol/dichloromethane=2/2/6.

In the present invention, a peptide fragment containing a modified amino acid or non-amino acid can be also prepared by cleaving a protected peptide fragment from a weak acid-cleavable resin without introducing a modified amino acid or non-amino acid, into a peptide chain, followed by a residue-specific modification of a desired amino acid residue. The residue-specific modifying method is as described above.

The aforementioned production method can be applied to a protected peptide fragment containing one or more modified amino acids or non-amino acids, without limitation. Inter alia, it is preferable that the aforementioned method is used in preparing a protected peptide fragment containing one or more modified amino acids or non-amino acids represented by the following formula 9, or a salt thereof.

That is, it is a peptide represented by the formula 9; $(R1)_n$-Gly-Ser(X1)-A(R)-Phe-Leu-Ser(X2)-Pro-OR2
(wherein -A(R)— is the aforementioned amino acid or non-amino acid which has undergone modification. Inter alia, A is preferably serine, threonine, cysteine, homocysteine, lysine, ornithine, glutamic acid, 2-aminoadipic acid, diaminoacetic acid, 2-aminomalonic acid, aspartic acid, tyrosine or asparagine, R is preferably a modifying group such as an acyl group, a sugar, a phosphate group, a sulfate group, an alkyl group, an aralkyl group, and an aroyl group, and it is preferable that R is bound to a reactive substituent of a side chain of A via an ester bond, an ether bond, a thioether bond, a disulfide bond, an amido bond, an O-glycoside bond or an N-glycoside bond.

R1 denotes an alkoxycarbonyl group optionally having a substituent such as t-butoxycarbonyl (Boc), trichloroethyloxycarbonyl, t-amyloxycarbonyl, 9-fluorenylmethoxycarbonyl (Fmoc), methylsulfonylethoxycarbonyl, trichloroethoxycarbonyl, 2-(trimethylsilyl)ethoxycarbonyl and pyridine-4-methoxycarbonyl; a cycloalkyloxycarbonyl group optionally having a substituent such as cycloheptyloxycabonyl, and cyclohexyloxycarbonyl; an aralkyloxycarbonyl group optionally having a substituent such as benzyloxycarbonyl (Z), p-methoxybenzyloxycarbonyl (pMZ), p-chlorobenzyloxycarbonyl (Cl-Z), p-bromobenzyloxycarbonyl (Br-Z), p-nitrobenzyloxycarbonyl, adamantyloxycarbonyl, 2-phenylisopropyloxycarbonyl, p-methylphenylisopropyloxycarbonyl, p-biphenylisopropyloxycarbonyl and 3,5-dimethoxy-α, α-dimethylbenzyloxycarbonyl; an aralkyl group optionally having a substituent such as benzyl (Bzl), benzhydryl, and trityl; an acyl group such as trifluoroacetyl, phthaloyl, formyl, benzenesulfonyl, p-toluenesulfonyl (Ts), o-nitrophenylsulfenyl, 2,4-dinitrophenylsulfenyl, and 3-nitro-2-pyridylsulfenyl; dithiasuccinoyl, 2-nitrophenylthio, diphenylphosphinyl, diphenylphosphinothioyl, or dimethylphosphinothioyl, n is 1 or 2, X1 and X2 denote a protecting group for a hydroxy group of a serine side chain, and denote a lower alkanoyl group having 1 to 6 carbon atoms such as an acetyl group; an aroyl group such as a benzoyl group; a group derived from carbonic acid such as a benzyloxycarbonyl group and an ethoxycarbonyl group, or as a group suitable for etherification which binds the aforementioned substituent R to a side chain via an ether bond, denotes a t-butyl group, a benzyl group, a tetrahydropyranyl group, a trityl group, or a silyl group such as a t-butyldimethylsilyl group, R2 denotes a protecting group or the absence of a protecting group and, when there is a protecting group, denotes an alkyl ester group (e.g. straight, branched or cyclic alkyl ester group such as methyl ester, ethyl ester, propyl ester, butyl ester, t-butyl ester, cyclopentyl ester, cyclohexyl ester, cycloheptyl ester, cyclooctyl ester, and 2-adamantylester), an aralkyl ester group (e.g. benzyl ester, 4-nitrobenzyl ester, 4-methoxybenzyl ester, 4-chlorobenzyl ester, benzhydryl ester group), a phenacyl ester group, a benzyloxycarbonylhydrazide group, a t-butoxycarbonylhydrazide group, or a tritylhydrazide group)

or a salt thereof.

In the formula 9, R1 is preferably a Boc group, a Z group, a pMZ group or a Fmoc group, and examples of a protecting group represented by X1 and X2 include preferably a t-butyl group and a 34-benzyl group, more preferably a t-butyl group. As R2, hydrogen or a thioester group is preferable.

Further, the aforementioned production method can be suitably used upon preparation of ghrelin, preferably human, rat, mouse, porcine, chicken, eel, bovine, equine, ovine, frog, trout or canine ghrelin, or a ghrelin derivative. In addition, the aforementioned production method is suitably used in the preparation of a part containing a modified amino acid or non-amino acid in the ghrelin or ghrelin derivative. Structures of ghrelins of respective organisms are described in Table 1.

More specifically, the aforementioned production method is useful in preparing a peptide fragment (a) which comprises a sequence of at least first to forth amino acids from the N-terminal in an amino acid sequence set forth in any one of SEQ ID NOS: 1 to 21, preferably comprises a sequence of first to fifth amino acids from the N-terminal in said amino acid sequence, or comprises a sequence of first to seventh amino acids from the N-terminal in said amino acid sequence, (b) in which a hydroxy group of the side chain of serine or threonine which is the third amino acid from the N-terminal is acylatad, preferably acylated with a saturated or a unsaturated acyl group having a carbon number of 2 to 35, preferably 6 to 18, and (c) in which one or more reactive functional groups which may cause an undesirable side reaction upon preparation of a peptide fragment, selected from the group consisting of hydroxy group, an amino group, a guanidino group, an imidazolyl group, an indolyl group, a mercapto group and a carboxyl group, in a side chain of an amino acid, preferably a hydroxy group and an amino group are protected with a protecting group.

In the present invention, a protected peptide fragment containing no modified amino acid or non-amino acid is prepared apart from the aforementioned protected peptide fragment containing a modified amino acid or non-amino acid.

A peptide fragment containing no amino acid or non-amino acid which has undergone modification such as acylation, glycosylation, and phosphorylation, of a peptide or a protein in the present invention can be produced by the known per se gene recombinant technique or enzyme method. For example, it can be prepared by a method comprising a step of culturing a cell transformed with an expression vector having a nucleotide sequence encoding a peptide having an amino acid sequence of the aforementioned peptide fragment (hereinafter, referred to as desired peptide), collecting the desired peptide from the culture, and a step of protecting, with a protecting group, a functional group which may cause an undesired side reaction, among side chain functional groups of the desired peptide obtained in the aforementioned step. A method for constructing an expression vector can be performed by the conventional method in the art. For constructing of an expression vector, as other elements necessary for highly expressing the desired peptide, for example, a promoter, a terminator, and a splicing site, those already known in the conventional method can also be appropriately used. A host cell which is transformed with the expression vector is not particularly limited, but a host cell can be used by appropriately selecting a cell which can suitably express a nucleotide sequence encoding the desired peptide from a prokaryotic cell and a eukaryotic cell, for example, a microorganism cell such as *Escherichia coli*, yeast and an animal cell which have been already used in the conventional method. Protection of a side chain functional group of the desired peptide may be performed by the aforementioned method.

A peptide fragment containing no modified amino acid or non-amino acid can be produced by a method comprising:

step (1); (a) a step of culturing a cell transformed with an expression vector having a nucleotide sequence encoding a fusion protein optionally with a protective peptide added to the desired peptide via a linker sequence, and collecting the fusion protein from the culture;

step (2); a step of cleaving and separating a protective peptide and, optionally, a linker sequence and the desired peptide from the fusion protein obtained in the step (1), followed by optional further purification; and step (3); a step of protecting, with a protecting group, a functional group which may cause an undesirable side reaction among side chain functional groups of the desired peptide obtained in the step (2).

A protective peptide is used for the purpose of suppressing degradation of the desired peptide by an enzyme in a host cell, and such a peptide is not particularly limited as far as the purpose can be attained, but a fragment having an amino acid sequence relating to β-galactosidase derived from *Escherichia coli* may be used. The amino acid sequence relating to said enzyme is known to a person skilled in the art, and a peptide fragment derived from β-galactosidase is widely used as a protective peptide in a fusion protein method by a person skilled in the art.

A linker sequence is a sequence which is inserted between a protective peptide and the desired peptide when cleavage and separation of a protective peptide and the desired peptide are not properly performed, for example, when there is no suitable enzyme for cleaving and separating a protective peptide and the desired peptide in the step (2). Therefore, the sequence of said protective peptide can be appropriately selected so that cleavage and separation of a linker sequence and the desired peptide are properly performed in the step (2).

Cleavage and separation of a protective peptide and, optionally, a linker sequence and the desired peptide can be performed by an enzymatic and/or chemical method.

As enzymatic and chemical cleaving methods, the method described in Methods in ENZYMOLOGY, vol. 185, Gene Expression Technology, edited by David V. Goeddel, published by ACADEMIC PRESS, INC) can be also used.

Examples of a chemical cleaving method include a method for cleaving a C-terminal side of methionine with cyanogen bromide (D. V. Goeddel et al, Proc. Natl. Acad. Sci. USA, Vol. 76, p. 106–110, 1979), a method for cleaving between a -Asp-Pro- sequence with formic acid (Biochem. Biophys. Res. Commun., Vol. 40, p. 1173, 1970), a method for cleaving between a -Asn-Gly- sequence with hydroxylamine, and a method for cleaving a C-terminal side of trypsin with BNPS-skatole or N-chlorosuccinimide. For example, when methionine is not contained in an amino acid sequence relating to the desired peptide, cleavage at a cleavage site region can be chemically performed by cyanogen bromide treatment by introducing methionine into an end of a cleavage site region adjacent to the desired peptide.

In addition, as an enzymatic cleaving method, a cleavage site region which can be specifically recognized as a substrate by an enzyme used for cleavage treatment may be set. Examples thereof include a method for cleaving a peptide bond at a center of a basic amino acid pair of arginine-arginine, lysine-lysine, arginine-lysine and lysine-arginine, or a peptide bond at a center of an amino acid pair of arginine-methionine, arginine-alanine or arginine-valine with an *Escherichia coli* OmpT protease (Sugimura, K. and Nishihara, T. J. Bacteriol. 170: 5625–5632, 1988), a method for cleaving between a -X-Gly- sequence in a X-Gly or Pro-X-Gly-Pro sequence with Collagelase (Proc. Natl. Acad. Sci. USA, Vol. 81, p 4692–4696, 1984), a method for cleaving a C-terminal side of Lys in -Asp-Asp-Asp-Lys- sequence (SEQ ID NO: 22) with Enterokinase, a method for cleaving a C-terminal side of Arg in a -Ile-Glu-Gly-Arg- sequence (SEQ ID NO: 23) with blood coagulation Factor Xa (JP-A No. 61-135591), a method for cleaving a C-terminal side of Arg in a -Gly-Pro-Arg- sequence with Thrombin (JP-A No. 62-135500), a method for cleaving a C-terminal side of -Arg- with Trypsin or Clostripain, a method for cleaving a C-terminal side of Arg or Lys with endoprotease Arg-C (Nature, Vol. 285, p 456–461, 1980), a method for cleaving a C-terminal side of a Lys-Arg, Arg-Arg or Pro-Arg sequence with a *Saccaharomyces cerevisiae* Kex2 protease and a derivative thereof (Biochem. Biophys. Res. Commun., Vol. 144, p 807–814, 1987, JP-A No. 1-199578, JP-A No. 10-229884), a method for cleaving a C-terminal side of Lys with lysyl endopeptidase or endopeptidase Lys-C (JP-A No. 61-275222), a method for cleaving a C-terminal side of Asp or Glu with a *Staphylococcus aureus* V8 protease (Proc. Natl. Acad. Sci. USA, Vol. 69, p 3506–3509, 1972), a method for cleaving a C-terminal side of a -Phe-Arg- sequence with Kallikrein (JP-A No. 62-248489), a method for cleaving between Leu-Leu of a -Pro-Phe-His-Leu-Leu-Val-Tyr- sequence (SEQ ID NO:24) with Renin (JP-A No. 60-262595), a method for cleaving a C-terminal side of a -Glu-Gly-Arg- sequence with Urokinase (JP-A No. 2-100685), a method for cleaving a C-terminal side of a Val-Asp-Asp-Asp-Asp-Lys sequence (SEQ ID NO: 25) with Entero-peptidase (Biotechnology, Vol. 6, p 1204–1210, 1988), a method for cleaving a C-terminal side of poly-Gly with Lysostaphin (JP-A No. 1-160496), and a method for cleaving a C-terminal side of Lys-Arg, Arg-Arg or Pro-Arg with *Kluverromyces lactls* (JP-A No. 1-124390).

An expression vector, a host cell and protection of a side chain functional group of the desired peptide in the present method are as described for the aforementioned method.

Further, as a method for producing a peptide fragment containing no amino acid or non-amino acid which has undergone modification using a genetic recombination method or an enzymatic method, the method described in International Publication No. WO 99/38984 may be used.

When a peptide fragment containing no modified amino acid or non-amino acid is a peptide fragment containing no amino acid or non-amino acid which has undergone modification of ghrelin or ghrelin derivative (hereinafter, referred to as ghrelin fragment (non-modified component)), a method for producing the fragment by a genetic recombination method and an enzymatic method is described in International Publication No. WO 01/07475.

Further, a ghrelin fragment (non-modified component) can be also produced by using a two-step enzymatic method with an OmpT protease or a derivative thereof, as well as a Kex2 protease or a derivative thereof, by adopting a protected protein and a linker sequence used for producing glucagons like peptide-1 described in International Publication No. WO 00/52193. In this method, since an endogenous OmpT protease of *Escherichia coli* which is a host can be utilized, it is not necessary to prepare an enzyme separately. The derivative of an OmpT protease or a Kex2 protease is not particularly limited as far as it has the same activity as that of an OmpT protease or a Kex2 protease. Examples of the OmpT protease derivatives include enzymes belonging to an Omptin family, representatives of which are an OmpP protease of *Escherichia coli*, and a pgtE protease of *Salmonella*, and partial peptides containing an active part of an OmpT protease. Examples of the Kex2 protease derivative include those described in JP-A No. 10-229884, and enzymes belonging to a Kex2 family, representatives of which are Furin and PC1/3.

In the present method, a ghrelin fragment (non-modified component), inter alia, aghrelin (8–28) fragment, in particular, a human ghrelin (8–28) fragment can be effectively obtained by a two-step enzyme treating method using an OmpT protease and a Kex2 protease, by using, instead of a linker sequence EPHHHHPGGRQMHGYDADVRLYR-RHHGSGSPSRHPR (SEQ ID NO: 26) described in International Publication No. WO 00/52193, a sequence EPHH-HHPGGRQMHGYDADVRLYRRHHGSGSPSRHRR (SEQ ID NO: 27) in which the 35$^{th}$ proline residue is substituted with an arginine residue in the aforementioned sequence, as a linker sequence, as shown in Example 13. Although a cleavage recognizing site is separately produced in addition to a cleavage recognition site of an OmpT protease in the newly found linker sequence described in SEQ ID NO: 27, cleavage occurs precisely only at the desired site (see Example 3).

Further, upon purification and storage of a protected peptide fragment (non-modified component), by adjusting a pH of a solution used for purification or storage to 4 to 8, elimination of a protecting group can be prevented. Therefore, by suppressing elimination of a protecting group, a highly pure modified peptide or protein can be produced at a high recovery yield. As the solution used for purification or storage, an aqueous solution is preferable. Examples of such solution include water, preferably, ultrafiltration water and a sodium acetate solution. As apparent from Example 15 in which stability of a protected human ghrelin (8–28) fragment in an aqueous solution was examined, stability of a peptide fragment protected with a Boc group is different depending on the status of an aqueous solution and, in particular, in the status of an aqueous solution at a pH of 2 or lower, clear elimination of the present protecting group was recognized and, therefore, when a Boc group is used as a protecting group, it is preferable to set a pH of a solution upon purification or storage between 4 to 8.

Then, in the present invention, the above-obtained (a) protected peptide fragment containing one or more modified amino acids or non-amino acids and (b) protected peptide fragment containing no modified amino acid or non-amino acid are condensed, optionally followed by deprotection of a protecting group for a side chain functional group of an amino acid or a non-amino acid.

It is preferable that the above condensation reaction is performed by a liquid phase method. In addition, in the reaction for condensing (a) and (b) peptide fragments by a liquid phase method, a side chain functional group of each amino acid or non-amino acid of the peptide fragments is usually protected with a protecting group. Examples of the protecting group include those exemplified above as a protecting group for each functional group. Examples of a preferable protecting group include protecting groups such that a protecting group for the (a) and (b) protected peptide fragments can be eliminated under the same eliminating condition. In this case, since a weak acid-cleavable resin has been already cleaved, it is not necessary to take cleavage conditions for a weak acid-cleavable resin into consideration. As a protecting group for a side chain functional group in this case, a protecting group which is eliminated under eliminating conditions for an N-terminal amino group is preferable.

In the reaction for condensing the (a) and (b) protected peptide fragments by a liquid phase method, reagents and conditions used for condensation are appropriately selected from those described in an amino acid condensing reaction as described above. Preferably, they are selected from methods which hardly produce impurities such as racemic isomers of a peptide or a protein as a byproduct. In particular, preferable examples of a reagent used in condensation (condensing agent) include 2-(1-hydrobenzotriazol-1-yl)-1,1,3,3-tetramethyluronium hexafluorophosphate (HBTU), 2-(1-hydrobenzotriazol-1-yl)-1,1,3,3-tetramethyluronium tetrafluoroborate (TBTU), diphenylphosphorylazide (DPPA), diphenylphosphorocyanidate (DEPC), diisopropylcarbodiimide (DIPC), dicyclohexylcarbodiimide (DCC) and 1-ethyl-3-(3-dimethylaminopropyl)carbodiimide (EDC). Inter alia, it is preferable that a condensing agent is diisopropylcarbodiimide (DIPC), dicyclohexylcarbodiimide (DCC) or 1-ethyl-3-(3-dimethylaminopropyl)carbodiimide (EDC), and condensation of a peptide fragment using the condensing agent is performed in the presence of 1-hydroxybenzotriazole (HOBt), 1-hydroxysuccinimide (HOSu) or 3,4-dihydro-3-hydroxy-4-oxo-benzotriazine (HOOBt).

In the condensed reaction product, a protecting group for a side chain of an amino acid or a non-amino acid can be appropriately deprotected. Reagents and conditions for deprotection in this case are preferably selected from methods which hardly produce impurities such as recemic isomers of a peptide or a protein as a byproduct.

Conditions for eliminating each protecting group may be, for example, according to the known method described in the aforementioned "Fundamental and Experiment of Peptide Synthesis". As a method for eliminating a protecting group, there are methods utilizing, respectively, a strong acid, a weak acid, a base, a reducing regent (catalytic reduction, metal, thiol, etc.), an oxidizing reagent, a nucleophile, an electrophile, an ion, electron, light, a solvent and an enzyme. Selection of the protecting group can be performed by taking eliminating conditions of these eliminating methods into consideration.

As a method for removing a protecting group (deprotecting reaction), for example, acid treatment with trifluoroacetic acid, acetic acid, anhydrous hydrogen fluoride, methanesulfonic acid, trifluoromethane sulfonic acid, or a mixture thereof (preferably, trifluoroacetic acid, acetic acid, etc.); base treatment with diisopropylethylamine, triethylamine, piperidine or piperazine; catalytic reduction under a hydrogen stream in the presence of a catalyst such as Pd-carbon; zinc dust treatment in acetic acid (Zn/AcOH); and tetrabutylammonium fluoride (TBAF) treatment are used. The deprotecting reaction is generally performed at a temperature of about 40° C. or lower, preferably about 25° C. or lower, whereby, production of racemic isomers of a protected peptide fragment as a byproduct can be effectively suppressed. A reaction time for the deprotecting reaction is usually about 0.5 to about 5 hours.

In the above acid treatment, it is preferable to add a cation scavenger such as water, triisopropylsilane (TIPS), phenol, anisole, thioanisole, metacresol, paracresol, dimethyl sulfide, 1,4-butanedithiol, and 1,2-ethanedithiol (preferably, phenol). In addition, a 2,4-dinitrophenyl group used as a protecting group for imidazole of histidine is removed by thiophenol treatment, and a formyl group used as a protecting group of indole of tryptophan is removed by alkali treatment with a dilute sodium hydroxide solution or dilute ammonia in addition to the aforementioned deprotection by acid treatment in the presence of 1,2-ethanedithiol or 1,4-butanediol.

The reaction product obtained by the present invention can be isolated and purified by the conventional separating and purifying means such as gel filtration method, ion exchange chromatography, partition chromatography, high performance liquid chromatography, reverse phase high performance liquid chromatography and electrophoresis. The product to be purified is not limited to a modified peptide or protein as a final end product, but it goes without saying that a protected peptide fragment containing one or more modified amino acids or non-amino acids, or a protected peptide fragment containing no modified amino acid or non-amino acid, or the product as an intermediate in a step of producing them can be appropriately purified by the aforementioned separating and purifying means.

As described above, a modified peptide or protein can be produced. The aforementioned production method of the present invention can be applied to any modified peptides or proteins without any limitation. Inter alia, the production method is suitably used upon production of ghrelin, preferably human, rat, mouse, porcine, chicken, eel, bovine, equine, ovine, frog, trout or canine ghrelin, or ghrelin derivative. Structures of the aforementioned ghrelins of respective organisms are described in Table 1. Since ghrelin or ghrelin derivative obtained by the present invention is extremely high quality ghrelin or ghrelin derivative having a considerably small amount of impurities (in particular, racemic isomers of ghrelin or ghrelin derivative) as compared with ghrelin or ghrelin derivative obtained by the previous technique. As a result, sufficient purification can be effectively performed by a simpler purifying method, a working time can be shortened, and ghrelin or ghrelin derivative can be produced in a high yield. Also from this respect, the production method of the present invention is an extremely advantageous method as an industrial method for producing ghrelin or ghrelin derivative.

Examples of the aforementioned "high quality ghrelin or ghrelin derivative" include purified ghrelin or ghrelin derivative or a salt thereof which has a content of total anagolous substances of about not more than 1% (preferably about not more than 0.9%, more preferably not more than 0.8%, further preferably about not more than 0.7%). Herein, total analogous substances means a total of all impurities which are detected by high performance liquid chromatography. Examples of such impurities include racemic isomers of ghrelin or ghrelin derivative, high polar anagolous substances, and other impurities.

A particularly preferable embodiment of a method for producing a modified peptide or protein of the present invention is as follows: that is, the embodiment is a method for producing a modified peptide or protein comprising:

step 1; a step of producing, on a weakly acidic eliminating resin, a peptide fragment (a) which comprises a sequence of at least $1^{st}$ to $4^{th}$ amino acids from the N-terminal, in the amino acid sequence set forth in anyone of SEQ ID NOS: 1 to 21, preferably comprises a sequence of $1^{st}$ to $5^{th}$ amino acids from the N-terminal in said amino acid sequence, or comprises a sequence of $1^{st}$ to $7^{th}$ amino acids from the N-terminal in said amino acid sequence, (b) in which a hydroxy group of a side chain of serine or threonine which is $3^{rd}$ amino acid from the N-terminal is acylated, preferably acylated with a saturated or unsaturated alkyl group of a carbon number of 2 to 35, preferably 6 to 18, and (c) in which one ore more reactive functional groups which may cause an undesirable side reaction upon preparation of a peptide fragment and a reaction of condensing peptide fragments in the following step (4), selected from the group consisting of a hydroxy group, an amino group, a guanidino group, imidazolyl group, an indolyl group, a mercapto group and a carboxyl group, in a side chain of an amino acid, preferably a hydroxy group and an amino group are protected with a protecting group, step (2); a step of cleaving the peptide fragment from a weak acid-cleavable resin under weakly acidic conditions without elimination of a protecting group in the peptide fragment, step (3); a step of producing a peptide fragment which comprising an amino acid sequence other than an amino acid sequence possessed by the peptide fragment produced in the steps (1) and (2) in the amino acid sequence set forth in any one of SEQ ID NOS: 1 to 21, preferably a sequence of $6^{th}$ to $28^{th}$ amino acids from the N-terminal in said amino acid sequence, or a sequence of $8^{th}$ to $28^{th}$ amino acids from the N-terminal in said amino acid sequence, and in which one or more reactive functional groups which may cause an undesirable side reaction upon production of a peptide fragment and a reaction of condensing peptide fragments in the following steps (4), selected from the group consisting of a hydroxy group, an amino group, a guanidino group, an imidazolyl group, an indolyl group, a mercapto group and a carboxyl group, in a side chain of an amino acid or a non-amino acid, preferably a hydroxy group and an amino group are protected by a protecting group, and step (4); a step of condensing the peptide fragment produced in the step (2) and the peptide fragment produced in the step (3), optionally followed by deprotection of a protecting group for a reactive functional group.

A modified peptide or protein obtained by the method of the present invention is produced in the form of a free peptide or a salt thereof depending on reaction conditions. A free peptide and its salt are exchangeable by the conventional method. When a free peptide is converted into a pharmacologically acceptable salt, for example, the peptide may be reacted with the following exemplified inorganic acid or organic acid. As a salt of the peptide or the protein, a pharmacologically acceptable salt is preferable. Examples of such a salt, when the peptide or the protein has a basic group such as an amino group, include salts with inorganic acids (also referred to as inorganic free acid) (e.g. carbonic acid, bicarbonic acid, hydrochloric acid, sulfuric acid, nitric acid, boric acid, etc.), or organic acids (also referred to as organic free acid) (e.g. succinic acid, acetic acid, propionic acid, trifluoroacetic acid, etc.). When the peptide or the protein has an acidic group such as a carboxyl group, there are exemplified salts with inorganic bases (also referred to as inorganic free base) (e.g. alkali metals such as sodium, potassium, etc., alkaline earth metals such as calcium, magnesium, etc.), or organic bases (also referred to as organic free base)(e.g. organic amines such as triethylamine, etc., basic amino acids such as arginine, etc.). Alternatively, the peptide or the protein may form a metal complex compound (e.g. copper complex, zinc complex, etc.).

A modified peptide or protein produced by the method of the present invention can be utilized for various uses. For example, the aforementioned purified ghrelin or ghrelin derivative is low toxic, and can be administered to a mammal (e.g. human, monkey, dog, rat, mouse) as a medicament for treating eating disorders, an agent for promoting secretion of growth hormone, a remedy for heart disease, a remedy for stomach functional disease, an agent for protecting an intestinal tract mucosa or an agent for preventing small intestine mucosa disorder at nourishment via vein, a remedy for osteoporosis, an agent for reducing cachexia due to chronic disease, and a remedy for pulmonary dysfunction. The aforementioned purified ghrelin or ghrelin derivative can be orally administered as a tablet, a capsule, an elixir or a sustained-release preparation which is coated with a sugar coating as necessary, or may be parenterally administered in the form of an injection such as a sterile solution, a suspension and a sustained-release preparation with water or other pharmaceutically acceptable solution; nasal preparation such as a solution, and a suspension; pulmonary preparation such as a spray and an inhalation; a suppository. The aforementioned preparation can be produced by mixing the purified ghrelin or ghrelin derivative with the physiologically approved known carrier, flavor, excipient, vehicle, antiseptic, stabilizer, binder and the like in a unit dosage required for generally approved pharmacy.

EXAMPLES

The following examples further illustrate the present invention in detail, but the present invention is not limited by them. As a test method and an instrument used in the present examples, those described below were used unless otherwise indicated.

(Main Abbreviations)
HBTU; 2-(1H-benzotriazole-1-yl)-1,1,3,3,-tetramethyluronium hexafluorophosphate
DCC; dicyclohexylcarbodiimide,
HOBt; 1-hydroxybezotriazole
HOOBt; 3-hydroxy-3,4-dihydro-4-oxo-1,2,3-benzotriazine
TFA; trifluoroacetic acid
TIPS; triisopropylsilane
DIPEA; diisopropylethylamine
TBAF; tetrabutylammonium fluoride
TFE; trifluoroethanol
Fmoc; fluorenylmethoxycarbonyl
Boc; t-butyloxycarbonyl
tBu; t-butyl
TBDMS; t-butyl dimethylsilyl
Trt; trityl
Pac; phenacyl
DMF; N,N-dimethylformamide
DCM; dichloromethane
NMP; N-methylpyrrolidone
$Et_2O$; diethyl ether
DMAP; 4-dimethylaminopyridine
EDC; 1-ehtyl-3-(3-dimethylaminopropyl)carbodiimide (Protected Amino Acids and Resins Used for Synthesis)
Boc-Gly, Fmoc-Ser(TBDMS), Fmoc-Ser(tBu), Fmoc-Phe, Fmoc-Leu, Fmoc-Ser, Fmoc-Pro (all manufactured by Watanabe Kagaku Kogyo or Applied Biosystem), prolyl-2-chlorotrityl resin (Novabiochem).

(Instruments Used)

(a) Peptide Automatic Synthesizer
433A synthesizer manufactured by Applied Biosystem (b) Analytical HPLC System
Instrument: Shimadzu LC-10A System
Column: YMC-Pack PROTEIN-RP or YMC-Pack ODS AP-302 or YMC-Pack PROTEIN-C8 (all 4.6 mmϕ×150 mm)
Column temperature: 40° C.
Eluent: In 0.1% trifluoroacetic acid, the acetonitrile concentration was linearly changed to a maximum 100%.
Flow rate: 1 mL/min
Detection: UV (210 nm or 214 nm)
Injection amount: 10 to 50 µL (c) Preparative Chromatography System
Instrument 1: AKTA explorer 10S (chromatography system manufactured by Amersham Pharmacia Biotech)
Column SP-sepharose big beads (XK26/30) (resin manufactured by Amersham Pharmacia Biotech)
Inner diameter 26 mm× length 300 mm
YMC-ODS 120 s50 (HR26/15) (resin manufactured by YMC)
Inner diameter 26 mm×length 15 mm
Vydac C4 (HR10/30) (Vydac)
Inner diameter 10 mm×length 300 mm
Source 3ORPC (HR10/30) 23 mL (resin manufactured by Amersham Pharmacia Biotech)
Inner diameter 10 mm×length 30 mm
Conditions of flow rate, eluent and the like are separately described in Examples.
Instrument 2: Applied Biosystem BioCAD perfusion Chromatography workstation Column SP-Toyopearl 550-c (inner diameter 16 mm×280 mm manufactured by TOSOH)

YMC-ODS AM (Particle diameter 20 μm, inner diameter 21.5 mm×300 mm manufactured by YMC)

Reverse phase chromatography column ODS-80Ts (inner diameter 21.5 mm×300 mm column (108 mL) particle diameter 20 um, manufactured by TOSOH)

Conditions of flow rate, eluent and the like are shown in Examples separately.

(d) Preparative HPLC System

Instrument: Waters 600 Multisolvent Delivery System

Column: YMC-Pack ODS-A (5 μm, 20 mm×250 mm) or YMC-Pack PROTEIN-RP (5 μm, C4, 20 mm×250 mm)

Eluent: In 0.1% trifluoroacetic acid, the acetonitrile concentration was appropriately changed linearly to a maximum of 100%.

Flow rate: 10 mL/min Detection: 210 nm and 260 nm Injection: 10 to 2000 μL, 2000 μL or larger was injected with a pump.

(e) Mass Spectrometer

Instrument 1: Finnigan MAT Corporation TSQ700

Ion source: ESI

Detection ion mode: positive

Spray voltage: 4.5 kV

Capillary temperature: 250° C.

Mobile phase: 0.2% acetic acid-methanol mixed solution (1:1)

Flow rate: 0.2 mL/min

Scan range: m/z 300 to 1,500

Instrument 2: API3000 (TAKARA SHUZO Co., Ltd.)

Detection ion mode: positive mode

Scan type: Q1scan

Flow rate: 0.3 mL/min 1 count/0.1 msec during 5 min chase

Molecular range 500 to 3000 Mass (f) Amino Acid Sequence Analysis

Instrument: Applied Biosystem 477A type sequencer manufactured by Perkin Elmer (g) Amino Acid Composition Analysis Instrument: L-8500 type amino acid analyzing instrument manufactured by Hitachi, Ltd.

Sample: In a sealed tube, the sample was hydrolyzed with 6M hydrochloric acid containing 0.1% phenol at 110° C. for 24 hours. [Scale for producing [Lys$^{16,19,20,24}$(Boc)] human-derived ghrelin (8–28) and outline]

Hereinafter, Example 2 to Example 8 are results of culturing and purification for the purpose of obtaining about 0.6 g of [Lys$^{16,19,20,24}$(Boc)] hGhrelin(8–28) (denotes human-derived ghrelin. Hereinafter, the same) as a final purified product. The expression vector shown in Example 1 was transformed into *Escherichia coli*, to express a fusion protein having the amino acid sequence shown in the same Example. Fermentation was performed by high density culturing using a 2 L fermenter, and inclusion bodies were recovered. A half amount of the recovered inclusion bodies were used to initiate purification. An OmpT reaction (0.9 L scale), cation exchange SP-sepharose big beads (160 mL scale), a butoxycarbonylating reaction (0.5 L scale), a reverse phase column YMC ODS-120 s50 (80 mL scale) and a Kex2 reaction (0.3 L scale) were performed once, respectively. Reverse phase column Vydac C4 (25 mL scale) as final purification was performed two times. In a final purification step, fractionation analysis was performed by elution with linear concentration gradient. In addition, evaporator was used for desolvation and a glass fiber filter (Whatman plc) was used for filtration under reduced pressure.

Example 1

Construction of hGhrelin (8–28) Derivative Expression Vector p117 8–28oRR

Based on a cDNA gene sequence of hGhrelin (Kojima et al., Nature, vol. 402, p. 656–660, 1999), a DNA fragment of hGhrelin (8–28) was obtained using a total synthetic oligo-DNA (Pharmacia Biotech) by an annealing method. A total synthetic oligo-DNA and an amino acid sequence used for annealing are shown in FIG. 1A.

In order to insert this DNA fragment into a plasmid pGP117ompPR in which a gene of a fusion protein of *Escherichia coli* β-galactosidase derivative and human glucagon like peptide-1 had been introduced (International Publication No. WO 00/52193), pGP117ompPR was treated with restriction enzymes SalI and SacII, and subjected to agar gel electrophoresis to prepare a DNA fragment lacking a human glucagon like peptide-1 gene. After further treatment with alkaline phosphatase, this was ligated with a hGhrelin (8–28) derivative gene fragment which had been subjected to SacII treatment and T4 DNA kinase treatment, with T4 DNA ligase. The ligated plasmid was transformed into *Escherichia coli* DH5α strain to obtain a plasmid p117 8–28oPR. The plasmid expresses a fusion protein in which an amino acid sequence of hGhrelin (8–28) and a partial fragment (117 amino acid residues) of β-galactosidase are ligated with a linker sequence having an amino acid sequence of EPHHHHPGGRQMHGYDADVRLYR-RHHGSGSPSRHPR (SEQ ID NO: 26).

Further, PCR was performed by using this plasmid p117 8–28oPR as a template, KOD plus polymerase (Toyobo Co., Ltd.) as an enzyme, and the following two kinds of primers:

```
                                       (SEQ ID NO: 28)
ORI-RR:
GGTTCCGGATCCCCTTCTCGACATCGCCGGGAACAC (SEQ ID NO: 29)
SAL*R:
ATAAGTCGACTTATCGTGGCTGCAG
``` as a primer, and the amplified fragment was excised from the electrophoresed gel. Further, this was treated with restriction enzymes SalI and BamHI. The p117 8–28oPR which had been previously treated with restriction enzymes SalI and BamHI similarly and purified, and these fragments were ligated with a T4 DNA ligase, and the ligated plasmid was transformed into *Escherichia coli* DH5α strain to obtain a plasmid p117 8–28oRR. The plasmid expresses a fusion protein in which an amino acid sequence of hGhrelin (8–28) and a partial fragment of β-galactosidase (117 amino acid residues) are ligated with a linker sequence having an amino acid sequence of EPHHHHPGGRQMHGYDADVRLYR-RHHGSGSPSRHRR (SEQ ID NO: 27). The expressed fusion protein is shown in FIG. 1B below.

Example 2

Expression of Recombinant hGhrelin (8–28) Fusion Protein in *Escherichia coli* and Recovery of Inclusion Bodies The plasmid p117 8–28oRR made in Example 1 was transformed into *Escherichia coli* W3110 strain, and the transformed *Escherichia coli* was used to perform culturing at 2 L medium in a 3 L fermenter. This expression plasmid is a plasmid derived from pBR322, and expression thereof is induced with a lac promoter. In addition, the plasmid retains a tetracycline resistant gene as a drug resistance gene. The preculture was carried out in a LB broth by shaking at 32° C. for 14 hours. In the present culturing, a medium having the following composition was used. The medium composition is 4 g/L yeast extract, 4 g/L $K_2HPO_4$, 4 g/L $KH_2PO_4$, 2.7 g/L $Na_2HPO_4$, 0.2 g/L $NH_4Cl$, 1.2 g/L $(NH_4)_2SO_4$, 2 g/L $MgSO_4.7H_2O$, 40 mg/L $CaCl_2$, 40 mg/L $FeSO_4.7H_2O$, 10 mg/L $MnSO_4.nH_2O$, 10 mg/L $AlCl_3.6H_2O$, 4 mg/L $CoCl_2.6H_2O$, 2 mg/L $ZnSO_4.7H_2O$, 2 mg/L $Na_2MoO_4.2H_2O$, 1 mg/L $CuCl_2.2H_2O$, 0.5 mg/L $H_3BO_4$. Glucose as a carbon source was initially added to a medium at 1% to initiate culturing at 37° C. After glucose was depleted, glycerol as a carbon source was added to continue culturing. Thereafter, the culture solution was subjected to a pressure cell disrupting machine (Mantongorin) to disrupt cells, and about 80 g of inclusion bodies were recovered by a centrifuge. Further, these inclusion bodies were resuspended in 2 L of deionized water, and recovered with a centrifuge to wash the inclusion bodies. Finally, 200 mL of a suspension of the inclusion bodies having an $OD_{660}$ value of 530 was obtained.

The following Examples were performed using 100 mL (a half amount) of this inclusion body suspension.

Example 3

Processing of hGhrelin (8–28) Fusion Protein with Endogenous OmpT Protease

The inclusion body suspension obtained in Example 2 was diluted with additives and deionized water shown in the following reaction conditions so that a value of $OD_{660}$ became 100.0, and an OmpT reaction was performed under the following reaction conditions.

Reaction Conditions:

4M urea, 20 mM Tris-HCl pH 7.4, 50 mM NaCl, reaction volume: 800 mL, reaction temperature 32° C., reaction time 40 minutes The inclusion bodies were dissolved and diluted with 400 mL of 8M urea to $100OD_{660}$/mL, Tris-HCl and NaCl were added to the solution, and measured up with deionized water to 800 mL. Further, a pH was adjusted to 7.4 to initiate a reaction. At 0 minute, 20 minutes and 40 minutes from reaction initiation, sampling was performed, analysis was performed by HPLC, and the reaction was stopped at 40 minutes, at which a cleavage rate exceeded 80%. The reaction was stopped by increasing a pH to 11 with 5N NaOH. After the reaction ceased, the residue was removed by low speed centrifugation to obtain the supernatant.

(RHHGSGSPSRHRR)-hGhrelin (8–28) concentration: 2.23 mg/mL

Solution amount; 800 mL

Peptide content; 1.7 g

As a result of HPLC measurement and mass spectrometry, it was demonstrated that processing occurs precisely, and (RHHGSGSPSRHRR)-hGhrelin (8–28) is released. A value of ESI-MS measured with a mass spectrometer (TSQ-700) of Finnigan MAT Corporation was 4078 (theoretical value; 4077).

Example 4

Purification of (RHHGSGSPSRHRR)-hGhrelin (8–28) (Purification by Cation Exchange)

The supernatant of the OmpT protease reaction solution obtained in Example 3 was purified by cation chromatography.

Method:

Column used; SP-sepharose big beads (XK26/30)(160 mL) (resin manufactured by Amersham Pharmacia Biotech) Inner diameter 26 mm×length 300 mm Equilibrating and washing solution: 1.5 M urea, 50 mM $NaHCO_3$ pH 11

Eluent: 1.5 M urea, 0.5 M NaCl, 50 mM $NaHCO_3$ pH 11

Initiation, regenerating solution; 0.4M NaOH

Flow rate: 10 mL/min (2.5 cm/min)

Manipulation:

Initiation, equilibration: 0.4 M NaOH 2 column volumes → deionized water 2 column volumes → equilibration solution: 100% 3 column volumes Sample loading: Sample is loaded, and washed with an equilibrating and washing solution until UV is reduced (about 4 column volumes).

Elution: Performed at a stepwise of 100% of an elution solution.

Results: A purity of the peptide obtained from the elution solution was 90%, and a step recovery yield was 91.6%.

(RHHGSGSPSRHRR)-hGhrelin (8–28) concentration: 4.75 mg/mL

Solution amount: 300 mL

Peptide content: 1.43 g

Example 5

Tert-Butoxycarbonylation of (RHHGSGSPSRHRR)-hGrelin (8–28)

The purified (RHHGSGSPSRHRR)-hGrelin (8–28) is subjected to a reaction of addition of a Boc group, to protect an α amino group at the N-terminal and an amino group of a side chain of a Lys residue contained in a sequence.

Method: A total amount of 300 mL of the cation chromatography eluant was transferred to a glass beaker, and an equivalent (300 mL) of acetonitrile was added to 50% acetonitrile. Further, 1M of $(Boc)_2O$ was added at 8.8 mL (final concentration 20 mM, 25 equivalents) corresponding to a 5-fold mol amount of the number (total 5) of α amino groups present in (RHHGSGSPSRHRR)-hGrelin (8–28) and ε amino groups of a side chain of lysine residue, while stirring. Further, a pH was adjusted with 5N NaOH so that the pH was not reduced to 9 or lower, and the reaction was performed at room temperature for 60 minutes while stirring with a stirrer. Measurement of a reaction efficacy was monitored by HPLC analysis and measurement of a molecular weight.

Immediately after completion of the reaction, desolvation was performed by an evaporator. After desolvation, a pH was adjusted to 5.5 with acetic acid, and the precipitates were filtered with a glass fiber filter (Whatman plc) under reduced pressure. This step afforded 580 mL of a solution containing 1740 mg of ($N^\alpha$-Boc, Lys$^{16,19,20,24}$(Boc)]-(RHHGSGSPSRHRR)-hGhrelin (8–28).

Step recovery rate: 116% (Why a step recovery rate is greater than 100% is considered as follows: An absorption in HPLC is increased by addition of a Boc group, and an apparent recovery rate is increased.)

Mass spectrometry was performed using a mass spectrometer (TSQ-700) of Finnigan MAT Corporation. A measured value of ESI-MS was 4578 (theoretical value; 4577).

After the reaction, the molecular weight was increased (measured molecular weight=4578, theoretical molecular weight=4577) in many cases as compared with before t-butoxycarbonylation (measured molecular weight=4077, theoretical molecular weight=4077). This was presumed to be ($N^\alpha$-Boc, Lys$^{16,19,20,24}$(Boc)]-(RHHGSGSPSRHRR)-hGhrelin(8–28) in which four ε amino groups present in a side chain of lysine residue in a hGrelin(8–28) sequence and an α amino group of the N-terminal side were t-butoxycarbonylated.

Example 6

Purification of ($N^\alpha$-Boc,Lys(Boc)$^{16,19,20,24}$)-(RHHGSGSPSRHRR)-hGhrelin(8–28) by Reverse Phase Column Chromatograpy The [$N^\alpha$-Boc,Lys$^{16,19,20,24}$(Boc)]-(RHHGSPSRHRR)-hGhrelin (8–28) obtained in Example 5 was purified by a reverse phase column.

Method:
Column used: YMC-ODS 120 s50 (HR26/15) 80 mL (resin manufactured by YMC) Inner diameter 26 mm×length 15 mm
Equilibrating and washing solution: 10% acetonitrile, 30 mM sodium acetate pH 5.5
Eluent: 50% acetonitrile, 30 mM sodium acetate pH 5.5
Regenerating solution: 80% acetonitrile
Flow rate: 7 mL/min (2 cm/min)

After equilibration with 3 column volumes of an equilibrating solution, a sample was loaded, and a column was washed with 3 column volumes of an equilibrating solution (until UV was reduced). Elution was performed by a stepwise elution with 100% of an eluent. After elution, the column was washed with a regenerating solution.

An eluant was obtained as 150 mL of a solution containing 1770 mg of [$N^\alpha$-Boc, Lys$^{16,19,20,24}$(Boc)]-(RHHGSGSPSRHRR)-hGhrelin (8–28). To this was added 75 mL of ultra filtration water to dilute 1.5-fold, and acetonitrile contained in the solution was distilled off with an evaporator.

Step recovery rate: 98%

Example 7

Production of [Lys$^{16,19,20,24}$(Boc)]-hGhrelin(8–28) with Kex2 Protease

The peptide solution obtained in Example 6 was adjusted to the following conditions to perform a Kex2 reaction. That is, an ODS eluant was diluted with an ultrafiltraion water to 8 mg/mL, and 1M Tris-HCl of pH 8.3 was added to 50 mM. Further, 0.25M $CaCl_2$ was added to 5 mM, this was preincubated at 30° C. for 10 minutes, and Kex2 protease (JP-A No. 10-229884) solution (1×10$^7$ unit/mL) was added to 2.5×10$^4$ unit, followed by reaction in a constant temperature tank at 30° C. for 120 minutes while stirring with a stirrer. After the reaction, the pH was adjusted to 5.5 using acetic acid to stop the reaction. From HPLC, mass spectrometry and amino acid analysis, it was found that. [$N^\alpha$-Boc, Lys$^{16,19,20,24}$(Boc)]-(RHHGSGSPSRHRR) hGhrelin (8–28) which is a raw material disappeared after Kex2 cleavage, and [Lys$^{16,19,20,24}$(Boc)]hGhrelin(8–28) appears and, thus, precise processing occurs.

Example 8

Purification of [Lys$^{16,19,20,24}$(Boc)]hGhrelin(8–28)

The solution containing [Lys$^{16,19,20,24}$(Boc)]hGhrelin (8–28) obtained in Example 7 after the reaction was purified with a reverse phase column under the following conditions:

Method:
Reverse phase column used Vydac C4 (HR10/30) 23 mL column (Vydac)
Inner diameter 10 mm×length 300 mm Conditions:
Equilibrating and washing solution 10% acetonitrile, 0.1% TFA pH 3
Eluent: 50% acetonitrile, 0.1% TFA pH 3
Flow rate: 2 mL/min (linear flow rate 3 cm/min)

Elution was performed by a program in which 3 column volumes of an equilibrating solution was run, the solution after Kex2 reaction was loaded in two portions (20 mg/mL resin), the column was washed with 2 column volumes of a 10% eluent, and a linear gradient of 10% to 80% of an eluent was completed in 8 column volumes. Subsequently, the column was washed with 2 column volumes of a 100% eluent, during which each 6 mL fraction of eluants was collected. The fractions were analyzed by HPLC, and fractions not containing a linker [$N^\alpha$-Boc]-(RHHGSG-SPSRHRR) and uncleaved [$N^\alpha$-Boc, Lys$^{16,19,20,24}$ (Boc)]-(RHHGSGSPSRHRR) hGhrelin(8–28) were pooled.

Results:
Yield: 84.4%, purity 97.5%
[Lys$^{16,19,20,24}$(Boc)]hGhrelin(8–28) concentration: 5.62 mg/mL
Solution amount: 120 mL
Peptide content: 600 mg The eluted solution was desolvated with an evaporator, followed by lyophilization to obtain 600 mg of [Lys$^{16,19,20,24}$(Boc)]hGhrelin(8–28) from 1700 mg of a precursor (Example 3) obtained by processing of an OmpT protease derivative (FIG. 2).

Example 9

Table of Purification Recovery Rate and Purity of [Lys$^{16,19,20,24}$(Boc)]hGhrelin(8–28)

The following is a list of production yield of [Lys$^{16,19,20,24}$(Boc)]hGhrelin(8–28) shown in Example 3 to Example 7 (Table 2).

TABLE 2

List of production yield of (Lys$^{16,19,20,24}$(Boc))hGhrelin(8-28) shown in Example 3 to Example 8

| Step | Pre 8-28* (mg/mL) | Boc-Pre8-28** (mg/mL) | Boc-8-28*** (mg/mL) | Solution amount (L) | Boc-8-28 amount*** (g) | Yield of unit step (%) | Yield (%) | Purity (%) |
|---|---|---|---|---|---|---|---|---|
| Omp-T reaction | 2.23 | 2.51 | 1.68 | 0.8 | 1.3 | — | 100.0 | |
| After centrifugation | 1.97 | 2.21 | 1.48 | 0.8 | 1.2 | 91.6 | 91.6 | 90 |
| After cation chromatography | 4.75 | 5.33 | 3.58 | 0.3 | 1.1 | 87.1 | 79.8 | 95 |
| After t-butoxy-carbonylation | — | 3.11 | 2.08 | 0.6 | 1.3 | 116.6 | 93.0 | 92 |
| After reverse phase (YMC) concentration | — | 12.59 | 8.44 | 0.2 | 1.4 | 98.0 | 91.2 | 95 |
| After Kex2 reaction | — | — | 2.45 | 0.2 | 0.8 | 55.2 | 50.6 | |
| After reverse phase (Vydac) concentration | — | — | 5.62 | 0.12 | 0.6 | 84.4 | 42.1 | 98 |

Pre 8-28* means (RHHGSGSPSRHRR)-hGhrelin(8-28)
Boc-Pre8-28** means (N$^\alpha$-Boc, Lys$^{16,19,20,24}$(Boc))-(RHHGSGSPSRHRR)-hGhrelin(8-28).
Boc-8-28*** means (Lys$^{16,19,20,24}$(Boc))hGhrelin(8-28).

Example 10

(10-1) Synthesis of N-terminal Side Fragment ([N$^\alpha$-Boc, Ser$^2$, $^6$(tBu)]hGhrelin(1–7))(Method 1)

A prolyl-2-chlorotrityl resin (1.39 g, 1.0 mmol, manufactured by Novabiochem) was placed into a reactor equipped with a glass filter, and introduction of Fmoc-amino acid with HBTU and removal of Fmoc with piperidine were successively repeated to introduce Boc-Gly at an N-terminal residue, to construct a Boc-Gly-Ser(tBu)-Ser(TBDMS)-Phe-Leu-Ser(tBu)-Pro-2-chlorotrityl resin. The resulting protected peptide resin was treated with a 0.1 M TBAF/DMF solution (50 mL) for 30 minutes. The peptide resin was filtered, washed with DMF (30 mL) a few times, and washed with isopropyl alcohol, and DCM (30 mL). Then, the resulting de-TBDMS peptide resin was swollen with NMP (5 mL), and octanoic acid (588 mg, 4.1 mmol) and EDC.HCl (848 mg, 4.4 mmol) were added in the presence of DMAP (374 mg, 3.1 mmol) to react them for 16 hours. The resin was filtered, washed successively with NMP, isopropyl alcohol and DCM, and dried under reduced pressure to obtain a protected peptide resin in which a 3-positional serine side chain was octanoylated. To this was added 30 mL of a 0.5% TFA/DCM solution, and stirred at room temperature for 30 minutes to cleave the protected peptide from the resin. The resin was filtered, the filtrate was concentrated, and water was added to the residue to obtain precipitates. The precipitates were filtered, washed by stirring in hexane, and filtered again. This was dried overnight under reduced pressure to obtain 742 mg of the desired product (yield 72%). A purity of this product was investigated by HPLC and found to be 94%.

(10-2) Synthesis of N-terminal Side Fragment ([N$^\alpha$-Boc, Ser$^2$, $^6$(tBu)]hGhrelin(1–7)) (Method 2)

A prolyl-2-chlorotrityl resin (1.95 g, 1.0 mmol, manufactured Novabiochem) was placed into a reactor equipped with a glass filter, and introduction of Fmoc-amino-acid with HBTU and removal of Fmoc with piperidine were successively repeated to construct a Phe-Leu-Ser(tBu)-Pro-2-chlorotrityl resin. Then, Fmoc-Ser-OH was introduced with HOOBt/DCC, and de-Fmoc and condensation with HOOBt/DCC were repeated to introduce Boc-Gly at an N-terminal residue, to construct a Boc-Gly-Ser(tBu)-Ser-Phe-Leu-Ser(tBu)-Pro-2-chlorotrityl resin. The resulting peptide resin was swollen with NMP (5 mL), and octanoic acid (579 mg, 4.0 mmol) and EDC.HCl (847 mg, 4.4 mmol) were added in the presence of DMAP (374 mg, 3.1 mmol) to react them for 16 hours. The resin was filtered, washed successively with NMP, isopropyl alcohol and DCM, and dried under reduced pressure to obtain a protected peptide resin in which a 3-positional serine side chain is octanoylated. To this was added 30 mL of a 0.5% TFA/DCM solution, and the mixture was stirred at room temperature for 30 minutes to cleave the protected peptide from the resin. The resin was filtered, the filtrate was concentrated, and water was added to the residue to obtain precipitates. The precipitates were filtered, washed by stirring in hexane, and filtered again. This was dried overnight under reduced pressure to obtain 715 mg of the desired product (yield 69%). A purity of this product was investigated by HPLC and found to be 74%.

Example 11

Condensation and Deprotection of Fragment

[N$^\alpha$-Boc, Ser (tBu)$^{2,6}$]hGhrelin(1–7) and [Lys$^{16,19,20,24}$(Boc)]hGhrelin(8–28) obtained in Example 10-1 and Example 8 were quantitated in advance using an amino acid analyzer, and subjected to a condensation reaction. Each 0.19 mmol of [N$^\alpha$-Boc, Ser (tBu)$^{2,6}$]Ghrelin(1–7), HBTU and DIPEA were dissolved in 1 ml of DMF, and the solution was stirred at room temperature for 30 minutes. Thereafter, 0.16 mmol of [Lys$^{16,19,20,24}$(Boc)]hGhrelin(8–28) and 0.48 mmol of DIPEA were dissolved in 1.5 mL of DMF, and the aforementioned activated N-terminal side fragment solution was added dropwise while stirring. After 1 hour, the reaction solvent was distilled off under reduced pressure, and Et$_2$O was added to the residue to obtain precipitates, which were washed and dried. To the resulting powders was added 6 mL of TFA, and the mixture was slowly stirred at room temperature for 30 minutes. TFA was distilled off under reduced pressure, and Et$_2$O was added to the residue to obtain precipitates, which were washed and dried to obtain 0.70 g of the white powdery crude peptide. This was analyzed by analytical HPLC and, as a result, a purity of the desired product on a chart was 80%, and a retention time was consistent with that of a wholly chemical synthetic product.

Figure 3:
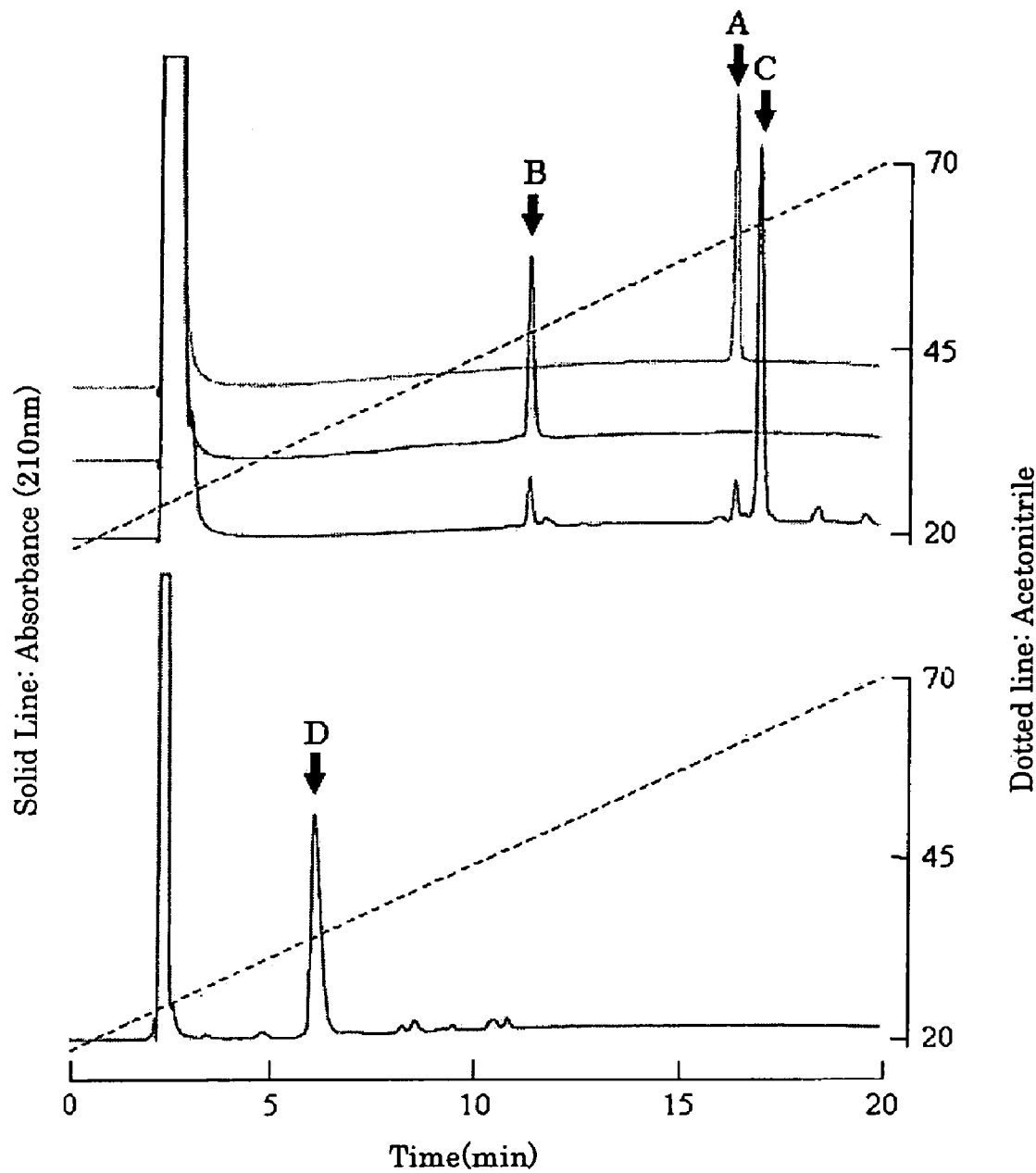
FIG. 3 shows a reaction of condensing fragments. Peak A denotes the peak of [N$^\alpha$-Boc, Ser$^{2,6}$(tBu)]hGhrelin(1–7), peak B denotes the peak of [Lys$^{16,19,20,24}$(Boc)]hGhrelin (8–28), peak C denotes the peak of [N$^\alpha$-Boc, Ser$^{2,6}$(tBu), Lys$^{16,19,20,24}$(Boc)]hGhrelin, and a peak D denotes the peak of hGhrelin.

Further, the semi-synthetic product and the wholly chemical synthetic product were coinjected, and peaks on chromatogram were consistent. HPLC charts before and after condensation are shown in FIG. 3.

Example 12

Purification of hGhrelin 0.70 g of the white powdery crude peptide obtained in Example 11 was dissolved in 7 mg/mL of 5% acetic acid, followed by purification under the following conditions;

Method, Conditions;

Column used: Source 30RPC (HR10/30) 23 mL column (resin manufactured by Amersham Pharmacia Biotech) Inner diameter 10 mm×length 30 mm Equilibrating and washing solution: 10% acetonitrile, 50 mM acetic acid Eluent: 60% acetonitrile, 50 mM acetic acid Regenerating solution: 80% acetonitrile Flow rate: 2.5 mL/min (2 cm/min)

Figure 4:
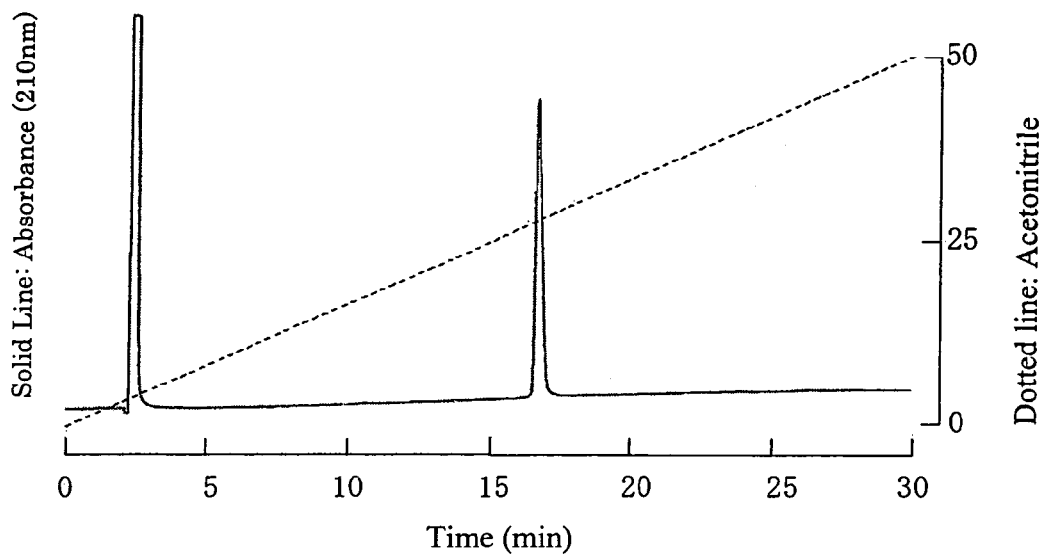
FIG. 4 shows results of HPLC measurement of purified hGhrelin.

After equilibration with 3 column volumes of an equilibrating solution, the hGhrelin-dissolved solution was divided into two halves, each half was loaded, and the column was washed with 3 column volumes of an equilibrating solution (until UV was reduced). Elution was performed by a program by which a linear gradient of 0% to 100% of an eluent was completed in 6 column volumes. Each 5 mL fraction of eluants was fractionated, analyzed by HPLC at an appropriate time, and fractions containing hGhrelin were pooled. The pool was desolvated with an evaporator, followed by lyophilization. As a result, 512 mg of hGhrelin having a purity of 98% (recovery rate 73%) was obtained. Results of HPLC analysis of purified hGhrelin are shown in FIG. 4.

The following Examples 13 to 15 relate to optimization of conditions shown in the aforementioned Examples 1 to 12. Therefore, it goes without saying that the present invention is not limited to the following conditions.

Example 13

Difference in Cleavage Efficacy of Kex2 Due to Difference in Sequences of Fusion Proteins A cleavage efficacy of Kex2 is greatly different depending on a recognition sequence of a substrate thereof. It has been reported that the cleavage efficacy becomes lowered in vivo in the order of a Kex2 cleavage sequence KR(10)>>RR(5) >>TR(1.2)>PR(1.0) (A value in parenthesis is a cleavage efficacy when that of PR is 1)(Proc. Natl. Acad. Sci 95 p 10384–10389 1998).

Figure 5:
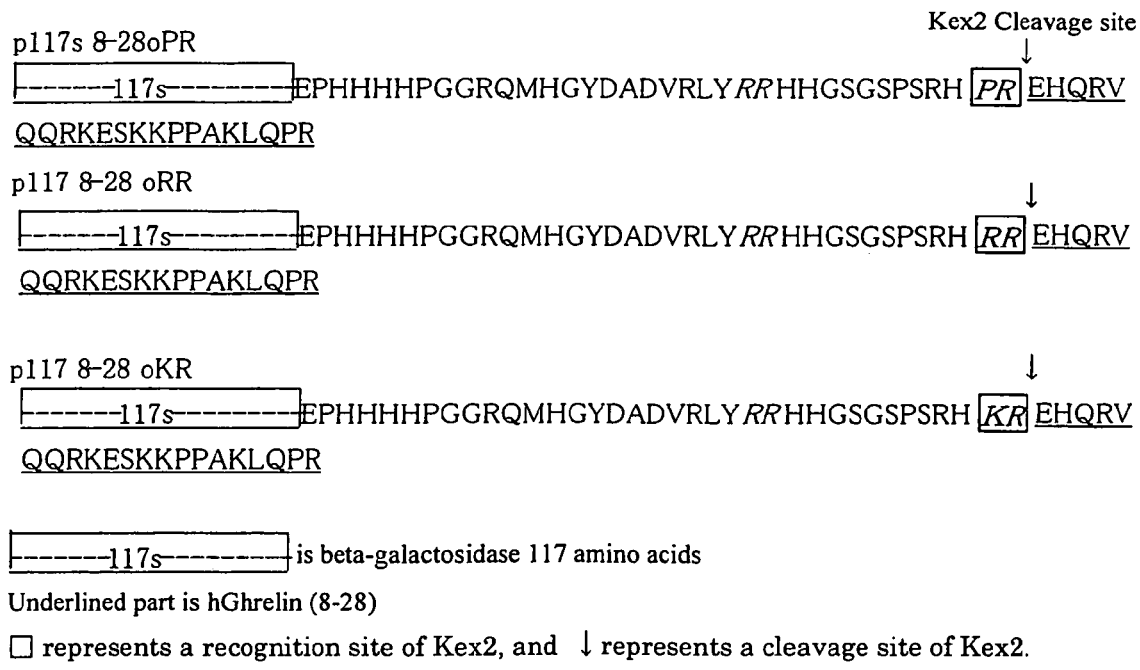
FIG. 5 shows amino acid sequences of fusion proteins having different cleavage recognition sites of Kex2 protease.

The following FIG. 5 shows proteins expressed by p117s 8–28oPR and p117 8–28oRR made in Example 1, and a plasmid p117 8–28oKR made by PCR using p117 8–28oPR as a template.

*Escherichia coli* W3110 harboring a plasmid expressing each of these three kinds of proteins was cultured, and purification was performed at an about 1/10 scale of that of the methods shown in Examples 2 to 6, thereby to prepare three kinds of peptides of [$N^\alpha$-Boc, $Lys^{16,19,20,24}$(Boc)]-(RHHGSGSPSRHPR) hGhrelin (8–28) (hereinafter, PR-hGhrelin (8–28)], [$N^\alpha$-Boc, $Lys^{16,19,20,24}$(Boc)]-(RHHGSGSPSRHRR) hGhrelin (8–28) (hereinafter, RR-hGhrelin (8–28)), and [$N^\alpha$-Boc, $Lys^{16,19,20,24}$(Boc)]-(RHHGSGSPSRHKR) hGhrelin (8–28) (hereinafter, KR-hGhrelin (8–28)), respectively.

The prepared peptides were subjected to Kex2 protease treatment using the method shown in Example 7. An analytical profile of HPLC at 60 minutes after reaction initiation is shown in FIG. 6.

Figure 6:
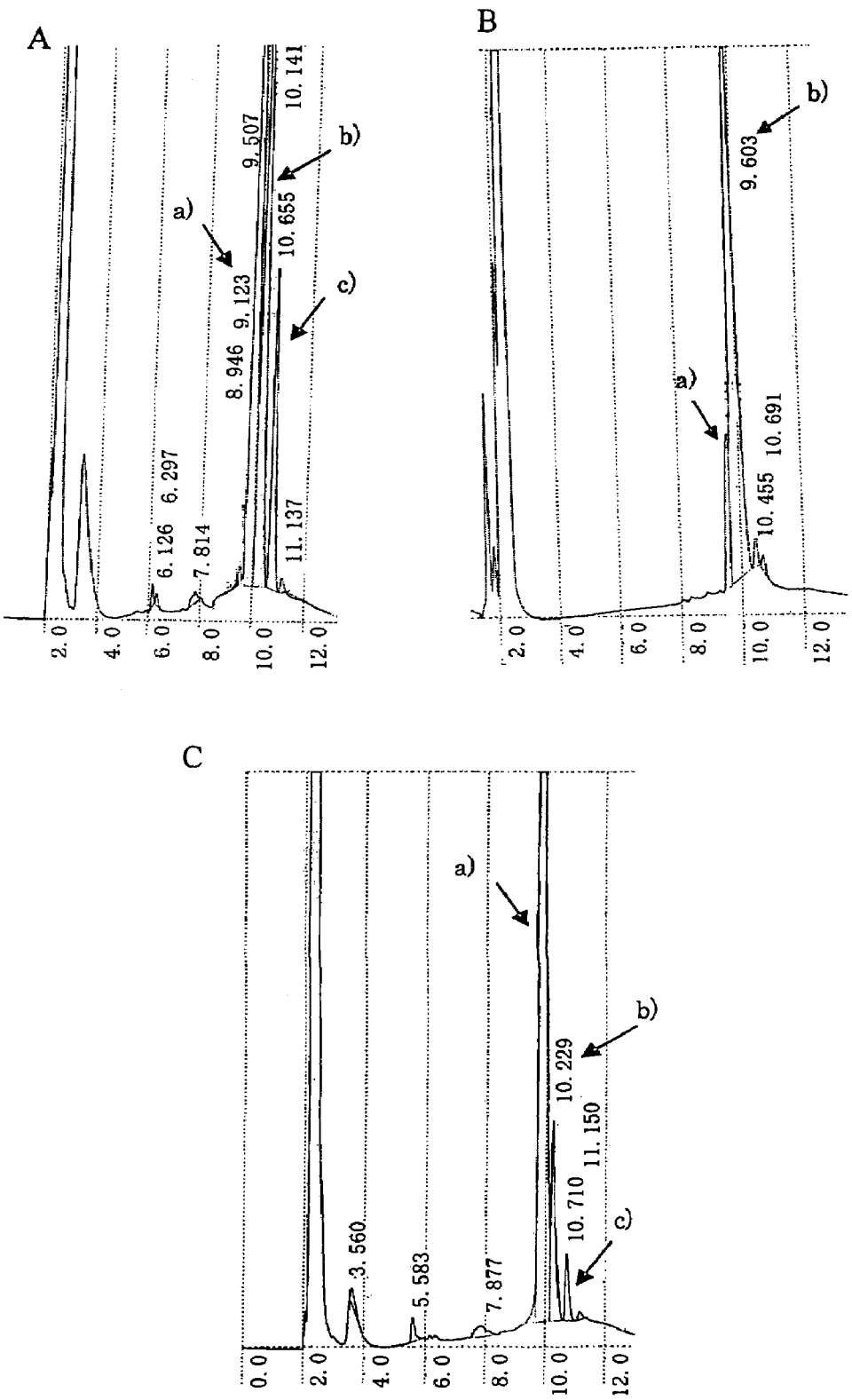
FIG. 6 shows results of HPLC analysis of Kex2 cleavage efficiency of respective fusion proteins prepared in FIG. 5.

As shown in FIG. 6, the order of cleavage rate is RR-hGhrelin (8–28)>PR-hGhrelin (8–28)>KR-hGhrelin (8–28), and RR-hGhrelin (8–28) was highest in the cleavage rate. In KR-hGhrelin (8–28), since a Boc group protects lysine residue of KR, and a charge of lysine is lost, cleavage did not occur at all. In addition, PR-hGhrelin (8–28) was low in the cleavage efficacy, and another cleavage occurred in hGhrelin (8–28). In degradation in this hGhrelin (8–28), cleavage occurred between arginine of an amino-acid number 15 of hGhrelin and lysine of an amino acid number of 16.

Example 14

Construction of Fusion Protein Suitable for Culturing *Escherichia coli*

In order to obtain a fusion protein suitable for culturing, a plasmid expressing fusion proteins shown in the following FIG. 7 besides the fusion protein shown in Example 13 and FIG. 5 was made. All fusion proteins shown in FIG. 7 were made by PCR from different primers using p117 8–28oPR as a template. For p117 8–28oRR, Those variants were constructed for the purpose of reducing an isoelectric point of a protein.

Each of the the plasmid expecting to express each fusion protein was transformed into *Escherichia coli* W3110strain, which was cultured in a 3L fermenter at a 2L scale. Pre-culturing was performed in a LB broth by shaking at 32° C. for 14 hours. A medium composition of the present culturing is the same as that shown in Example 2. Glucose as a carbon source was initially added to a culture medium at 1%, and culturing was initiated at 32° C. After depletion of glucose, glycerol was added, followed by culturing. And, at depletion of glucose, a culturing temperature was risen to 37° C. and, after culturing, cells were disrupted with a press cell disrupting machine (Mantongolin). The result of culturing was determined by a final turbidity and a turbidity at cell disruption. A higher turbidity of a cell, and a higher ratio of turbidities before and after cell disruption were determined to be a bacterium having higher productivity of inclusion bodies. The results are shown in graphs A and B in FIG. 8.

As seen from graphs A and B, from a final turbidity, and a ratio of turbidities before and after cell disruption, the 117 8–28oRR fusion protein exhibited highest productivity among the constructed fusion proteins. From the results of Examples 13 and 14, it was considered that the plasmid p117 8–28oRR expressing the protein is also suitable for culturing in Example 2.

Example 15

Stability of [$Lys^{16,19,20,24}$(Boc)]hGhrelin(8–28)

In Examples 6, 7 and 8, phenomenon was observed in which about 1 to 10% of Boc groups are eliminated in [$N^\alpha$-Boc, $Lys^{16,19,20,24}$(Boc)]-(RHHGSGSPSRHRR) hGhrelin (8–28) and [$Lys^{16,19,20,24}$(Boc)]hGhrelin(8–28). Since even when one of added Boc groups of [$Lys^{16,19,20,24}$(Boc)] hGhrelin(8–28) is eliminated, this leads to great reduction in a condensation rate at a condensing step, thereafter, stability of [Lys$^{16,19,20,24}$(Boc)]hGhrelin(8–28) was investigated in order to prevent elimination of a Boc group.

As a parameter influencing on degradation, a pH during storage and a storage temperature were contemplated. Then, stability under the following conditions was analyzed and assessed by HPLC.

Method: Freshly purified [Lys$^{16,19,20,24}$(Boc)]hGhrelin (8–28) was dissolved in a 30 mM sodium acetate solution, a pH was adjusted to 2, 3 or 4 using TFA, and a pH was adjusted to 6, 7 or 8 using 5N NaOH, and this was allowed to stand in a constant temperature bath at 4° C., 20° C., 37° C. or 42° C. for one week. After initiation of allowing to stand, sampling was performed at 0 hour, 2 hours, 6 hours, 9 hours, 24 hours, 48 hours, 96 hours and 168 hours, and the samples were analyzed by HPLC. Analysis was performed by assessing with time a ratio (%) of a peak area of [Lys$^{16,19,20,24}$(Boc)]hGhrelin(8–28) relative to a total peak area of results of analysis with HPLC.

Figure 9:
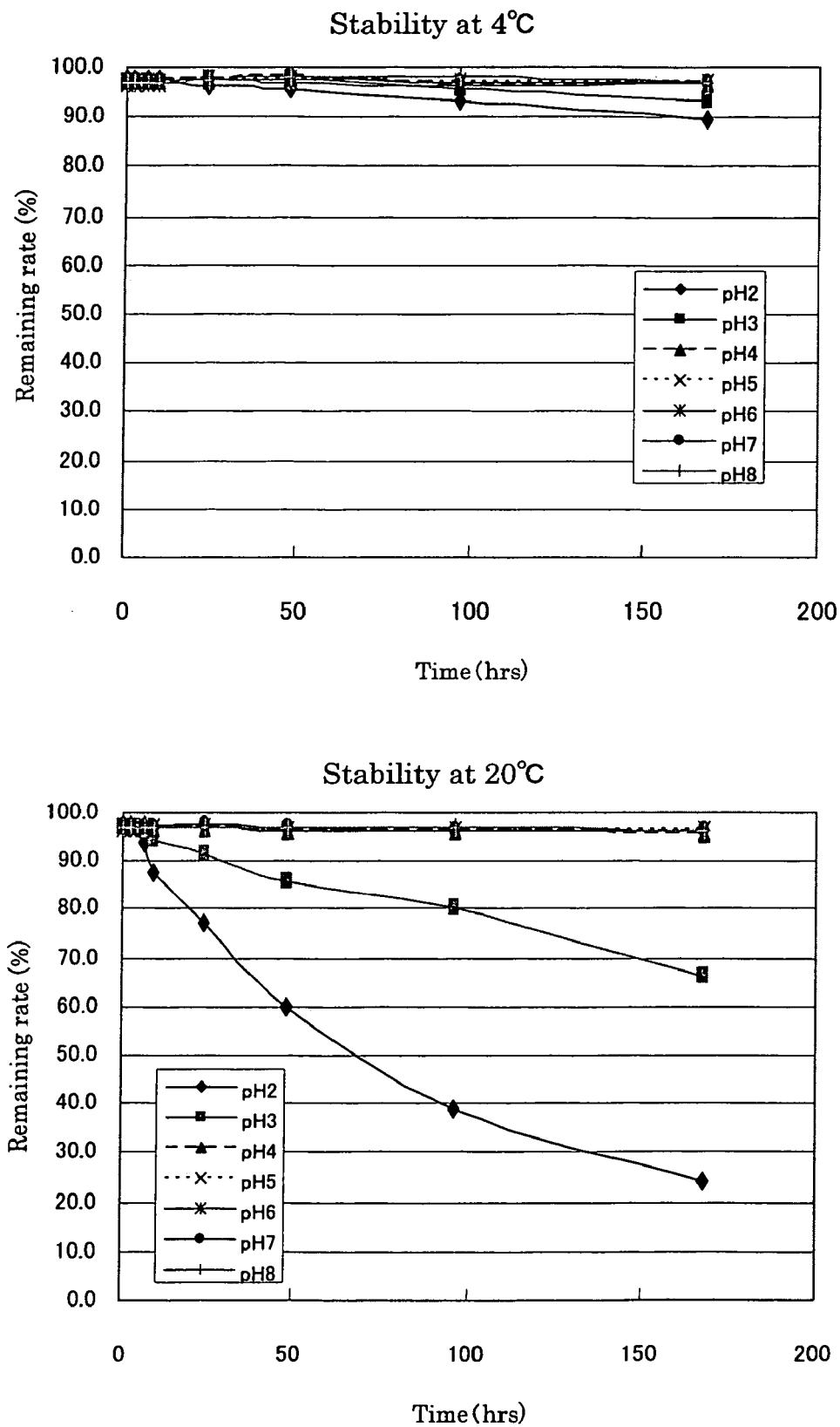
FIG. 9 shows results of stability assessment of [Lys$^{16,19,20,24}$(Boc)]hGhrelin(8–28).

Results; Four kinds of graphs summarized every storage temperature are shown in the following FIG. 9 and FIG. 10. It was seen that, at a lower pH (pH 3 or lower) and at a higher temperature, the degradation product is increased. In addition, it was seen that, at a pH of 4 or higher, [Lys$^{16,19,20,24}$(Boc)]hGhrelin(8–28) is also stable even at 42° C. Therefore, it was found that control of a pH is important for suppressing production of this degradation product.

Example 16

Production of hGhrelin (1–28) (Method 2)

(1) Construction of hGhrelin (8–28) Derivative-Expressing Vector p117-8-28ok

According to the same manner as that of Example 1, the plasmid p117-8-28ok was obtained. A difference between the plasmid p117-8-28PR made in Example 1 and the plasmid p117-8-28ok is only in that a linker sequence of the former is EPHHHHPGGRQMHGYDADVRLYR-RHHGSGSPSRHPR (SEQ ID NO: 26) and, a linker sequence of the latter is RRHHGSGSPSRHPR (SEQ ID NO: 35).

(2) Expression of Recombinant hGhrelin (8–28) Fusion Protein in *Escherichia coli*

The plasmid p117-8-28ok which is expected to express hGhrelin (8–28) fusion protein was transformed into *Escherichia coli* W3110 strain to obtain a transformant. This transformant was cultured in a 20 L medium using glucose and glycerol as a carbon source, to obtain a culture solution having a final OD$_{660}$ value of 54.

(3) Processing of hGhrelin (8–28) Fusion Protein with Endogeneous OmpT Protease

Cells (about 680 g) from the culture solution obtained in the above (2) were suspended in 20 L of a TE (10 mM Tris-HCl, 1 mM EDTA pH 8.0) buffer, and disruption treatment of cells were performed two times using a high pressure homogenizer. Thereafter, inclusion bodies were recovered by centrifugation, and the inclusion bodies were washed by suspending again in deionized water and centrifuging the suspension. Then, the inclusion body pellet (wet weight about 170 g) obtained by centrifugation was suspended in a small amount of deionized water, to obtain 550 mL of the inclusion body concentrate having an OD$_{660}$ value of 826. 50 mL was taken from 550 mL of the inclusion body concentrate, diluted with deionized water so that an OD$_{660}$ value became 50.0, Tris-HCl (pH 8.2) and EDTA (pH 8.0) were added to the final concentrations of 50 mM and 1 mM, respectively, and the inclusion bodies were dissolved in urea (final concentration 4.0 M). The inclusion bodies were dissolved by urea to cleave between Arg-Arg of a linker sequence RRHHGSGSPSRHPR (SEQ ID NO: 35) with an endogeneous OmpT protease. That is, the reaction solution was retained at 30° C. for 5 minutes, and subjected to OmpT protease treatment at 30° C. for 15 minutes. Thereafter, 3% ACOH was added to stop the reaction. The present treatment afforded 1.3 g of RHHGSGSPSRHPR-hGhrelin (8–28). As a result of analysis of a step of processing an ESI-MS 4019 (theoretical value 4018) hGhrelin (8–28) fusion protein with an endogeneous OmpT protease, by a high performance liquid chromatography, it was demonstrated that RHHGSG-SPSRHPR-hGhrelin (8–28) was retained as soluble form.

(4) Purification of RHHGSGSPSRHPR-hGhrelin (8–28) (Purification by Cation Exchange)

The OmpT protease reaction solution (900 mL) obtained in the above (3) was loaded on a cation exchange column SP-Toyopearl 550-c (bed volume 55 mL, 16 mm ID×280 mm manufactured by TOSOH) equilibrated with an equilibrating solution (1.5 M urea, 20 mM NaCl, 10 mM Tris-HCl pH 8.3) in four portions. Elution was performed by a program by which, after sufficient washing of a column with an equilibrating solution, a concentration gradient of an equilibrating solution 75% and an eluent (1.5 M urea, 1.5 M NaCl, 10 mM Tris-HCl pH 8.3) 25% to an eluent 100% was completed in 1.5 column volumes. A sample was taken every 5 mL, each fraction was analyzed by high performance liquid chromatography, and fractions not containing an *Escherichia coli* β-galactosidase derivative was taken. A total yield of four times was about 950 mg.

The aforementioned purified eluent (660 mL) was divided into two halves, and loaded two times on a YMC-ODS AM (particle diameter 20 μm, manufactured by YMC) 21.5 mm ID×300 mm column equilibrated with 2% acetonitrile and 0.1% TFA. After sufficient washing with an equilibrating solution, the column was eluted with an eluent (50% acetonitrile, 0.095% TFA). An elution peak was taken, and acetonitrile contained in an eluant was removed with a rotary evaporator to obtain 220 mL of a solution containing 720 mg of RHHGSGSPSRHPR-hGhrelin (8–28). Conditions of high performance liquid chromatography used in (3) and (4) are shown below:

Column; YMC ODS AP-302, detector; Hitachi high performance liquid chromatography system (D7000), flow rate; 1 mL/min, elution; linear concentration gradient of a buffer A (1.0% acetonitrile, 0.1% TFA) 100% to a buffer B (50.0% acetonitrile, 0.1% TFA) 100%, for 20 minutes.

(5) T-butoxycarbonylation of RHHGSGSPSRHPR-hGhrelin (8–28)

220 mL of the sample (containing 720 mg of RHHGSG-SPSRHPR-hGhrelin (8–28)) obtained in the (4) was transferred into a glass Erlenmeyer flask, and an equivalent amount of acetonitrile 220 mL was added. To this was added 1 M di-t-butyl dicarbonate at 4.4 mL (final concentration 10 mM, 25 equivalents) corresponding to a 5-fold mol amount of the number (total 5) of α amino groups and ε amino groups of Lys present in RHHGSGSPSRHPR-hGhrelin (8–28). Further, a pH was adjusted to 9 with triethylamine, and the materials were reacted at room temperature for 60 minutes while stirring with a stirrer. Acetic acid was added to the final concentration of 0.5% to stop the reaction to make a pH near neutral, and acetonitrile was rapidly removed with a rotary evaporator to obtain 300 mL of a solution containing 530 mg of Boc-RHHGSGSPSRHPR-[Lys$^{16,19,20,24}$(Boc)]hGhrelin(8–28). ESI-MS; 4519 (theoretical value; 4518).

Judging From elution profiles of RHHGSGSPSRHPR-hGhrelin (8–28) before and after the butoxycarbonylation and results of measurement of mass spectrometry, production of Boc-RHHGSGSPSRHPR-[Lys$^{16,19,20,24}$(Boc)]hGhrelin(8–28) was confirmed. For monitoring the present reaction, the following chromatography system was used. Column; YMC-C8, detector; Hitachi high performance liquid chromatography system (D7000), flow rate; 1 mL/min, elution; linear concentration gradient of a buffer A (1.0% acetonitrile, 0.1% TFA) 100% to a buffer B (60.0% acetonitrile, 0.095% TFA) 100% for 20 minutes.

(6) Production of [Lys$^{16,19,20,24}$(Boc)]hGhrelin(8–28) with Kex2 Protease

Boc-RHHGSGSPSRHPR-[Lys$^{16,19,20,24}$(Boc)]hGhrelin (8–28) obtained in the (5) was purified with a reverse phase column chromatography. The column was equilibrated with 2% acetonitrile, 0.1% TFA, and 10 mM sodium acetate at pH 4.5. The Boc derivative (about 500mg) was loaded on a YMC-ODS AM (particle diameter 20 μm, manufactured by TOSOH) 21.5 mm ID×300 mm column. After sufficient washing with an equilibrating solution, the column was eluted with an eluent (70% acetonitrile, 0.095% TFA, 10 mM sodium acetate, pH4.5). An elution peak containing Boc-RHHGSGSPSRHPR-[Lys$^{16,19,20,24}$(Boc)]hGhrelin (8–28)(420 mg) was collected, and acetonitrile was removed with an evaporator. To the present solution were added a 250 mM calcium chloride solution and 1 M Tris-HCl of pH 8.2 to the final concentrations of 5 mM and 50 mM, respectively. After retained at 30° C. for 5 minutes, Kex2 protease (JP-A No. 10-229884) solution (1×10$^7$ unit/mL) was added to 3×10$^4$ unit/mL, to react them at 30° C. for 45 minutes.

As a result of analysis of high performance liquid chromatography in the present step, it was demonstrated that a linker sequence RHHGSGSPSRHPR and [Lys$^{16,19,20,24}$(Boc)]hGhrelin(8–28) were cleaved.

(7) Purification of [Lys$^{16,19,20,24}$(Boc)]hGhrelin(8–28)

The solution after reaction (300 mL) containing [Lys$^{16,19,20,24}$(Boc)]hGhrelin(8–28)(320 mg) obtained in the (6) was adjusted to a pH of 3.5 with acetic acid, and loaded on a reverse phase chromatography column ODS-80Ts (21.5 mm ID×300 mm column (108 mL) particle diameter 20 μm, manufactured by TOSOH) previously equilibrated with 10% acetonitrile and 0.095% TFA. The column was washed with 2 column volumes of an equilibrating solution, and a program was performed in which a concentration gradient of a buffer A (10% acetonitrile, 0.095% TFA) 70% and a buffer B (65% acetonitrile, 0.1% TFA) 30% to a buffer B 100% was completed in 5 column volumes, thereby to elute [Lys$^{16,19,20,24}$(Boc)]hGhrelin(8–28). Eluant fractions (each 5 mL) were collected, and analyzed by high performance liquid chromatography (conditions are the same as those of (6)). Eluted fractions of [Lys$^{16,19,20,24}$(Boc)]hGhrelin(8–28) were collected, concentrated, and lyophilized to obtain 136 mg of [Lys$^{16,19,20,24}$(Boc)]hGhrelin(8–28). From 1300 mg of a precursor (the (3)) obtained by processing with an OmpT protease derivative, 136 mg of a final specimen of [Lys$^{16,19,20,24}$(Boc)]hGhrelin(8–28) was obtained.

(8–1) Synthesis of N-terminal Side Fragment [N$^\alpha$-Boc, Ser$^2$, $^6$(tBu)]Ghrelin(1–7)) (Method 1)

A Boc-Gly-Ser(tBu)-Ser(TBDMS)-Phe-Leu-Ser(tBu)-Pro-2-chlorotrityl resin was constructed on a prolyl-2-chlorotrityl resin (548 mg, 0.25 mmol, manufactured by Nova-biochem) by repeating successively introduction of Fmoc-amino acid with HBTU and de-Fmoc with piperidine to introduce Boc-Gly into a N-terminal residue using a peptide automatic synthesizer. The resulting protected peptide resin (757 mg) was treated with a 0.1 M TBAF/DMF solution (5 mL) for 1 hour. The peptide resin was filtered, washed with DMF (10 mL) a few times, and washed with isopropyl alcohol and methylene chloride (10 mL). Then, the resulting de-TBDMS peptide resin was swollen with DMF (10 mL), and octanoic acid (144.2 mg, 1.0 mmol) and EDC.HCl (211 mg, 1.1 mmol) were added in the presence of DMAP (31 mg, 0.25 mmol), to react them for 16 hours. The resin was filtered, washed successively with DMF, isopropyl alcohol and methylene chloride, and dried under reduced pressure to obtain a protected peptide resin in which the side chain at the third serine was octanoylated. To this was added 6 mL of a mixed solution of acetic acid 2 mL/TFE 2 mL/methylene chloride 6 mL, and the mixture was stirred at room temperature for 1 hour to cleave the protected peptide from the resin. The resin was filtered, the filtrate was concentrated, and ether was added to the residue to obtain precipitates. The precipitates were filtered, and dried to obtain 248 mg of the crude peptide (yield 96%). The present product was dissolved in about 2 mL of a mixed solution of acetic acid and acetonitrile, and the solution was added to YMC-Pack ODS-A (20 mm×250 mm), followed by elution with a linear gradient (flow rate: 10 mL/min) of acetonitrile 40% to 80% in 0.1% trifluoroacetic acid for 60 minutes. The desired fractions were taken, and lyophilized to obtain 210 mg desired product.

(8–2) Synthesis of N-terminal Side Fragment [N$^\alpha$-Boc, Ser$^2$, $^6$(tBu)]Ghrelin(1–7) (Method 2)

A Boc-Gly-Ser(tBu)-Ser(Trt)-Phe-Leu-Ser(tBu)-Pro-2-chlorotrityl resin was constructed on a prolyl-2-chlorotrityl resin (466 mg, 0.25 mmol, manufactured by Novabiochem) by repeating successively introduction of Fmoc-amino acid with HBTU and de-Fmoc with piperidine to introduce Boc-Gly into a N-terminal residue using a peptide automatic synthesizer. This resin was treated with 1% TFA, 5% TIPS/dichloromethane for 30 minutes, to perform removal of a Trt group and cleavage from the resin at the same time. After the resin was filtered, dichloromethane was distilled off under reduced pressure to concentrate the material, and Et$_2$O was added to obtain precipitates, which were dried to obtain 165 mg of Boc-Gly-Ser(tBu)-Ser-Phe-Leu-Ser(tBu)-Pro-OH as white precipitates. Then, phenacyl bromide (40 mg, 1.1 equivalents) and triethylamine (20 mg, 1.1 equivalents) were added to react them for 2 hours in about 3 mL of DMF. After the reaction, the reaction solution was placed into an about 5-fold amount of ethyl acetate, and the mixture was washed with water and an aqueous saturated sodium chloride solution, dried over sodium sulfate, filtered, and concentrated. The precipitates formed upon addition of Et$_2$O were dried to obtain Boc-Gly-Ser(tBu)-Ser-Phe-Leu-Ser(tBu)-Pro-OPac as white precipitates. Then, octanoic acid (18.2 mg, 1.1 equivalents), EDC.HCl (26.4 mg, 1.2 equivalents) and DMAP (1.4 mg, 0.1 equivalent) were added to react them overnight in about 2 mL of DMF. The reaction solution was placed into an about 5-fold amount of ethyl acetate, washed with water and an aqueous saturated sodium chloride solution, sodium sulfate was added to dry it, and this was filtered, concentrated, Et$_2$O was added to obtain 144 mg of Boc-Gly-Ser(tBu)-Ser(Octanoyl)-Phe-Leu-Ser(tBu)-Pro-OPac as white precipitates. Then, 1.5 mL of acetic acid and zinc powder (163 mg, 20 equivalents) were added to react them for 1 hour, this was filtered, and cold water was added to obtain precipitates, which were washed with Et$_2$O and dried. 65 mg of Boc-Gly-Ser(tBu)-Ser(Octanoyl)-Phe-Leu-Ser(tBu)-Pro-OH was obtained as white precipitates. The product was dissolved in about 2 mL of a mixed solution of aqueous acetic acid and acetonitrile, the solution was added to YMC-Pack ODS-A (20 mm×250 mm), and this was eluted with a linear gradient (flow rate: 10 mL/min) of acetonitrile 40% to 80% in 0.1% trifluoroacetic acid for 60 minutes. The desired fractions were taken, and lyophilized to obtain 50 mg of the desired product.

(9) Condensation and Deprotection of Fragment

[N$^\alpha$-Boc, Ser(tBu)$^{2,6}$]Ghrelin(1–7) and [Lys$^{16, 19, 20, 24}$(Boc)]hGhrelin(8–28) obtained in (8–1) and (7) were quantitated in advance using an amino acid analyzer, and subjected to a condensation reaction. 19.3 μmol of [N$^\alpha$-Boc, Ser(tBu)$^{2,6}$]Ghrelin(1–7), 20.3 μmol of HBTU and 20.3 μmol of DIPEA is dissolved in 500 μL of DMF, and the solution was stirred at room temperature for 1 hour. Thereafter, 18.4 μmol of [Lys$^{16, 19, 20, 24}$(Boc)]hGhrelin(8–28)) and 55.2 μmol of DIPEA were dissolved in 1 mL of DMF, and the aforementioned activated N-terminal side fragment solution was added dropwise while stirring. After three hours, the reaction solvent was distilled off under reduced pressure, and Et$_2$O was added to the residue to obtain precipitates, which were washed and dried. To the resulting powder was added 3 mL of TFA, and the mixture was stirred slowly at room temperature for 30 minutes. TFA was distilled off under reduced pressure, and Et$_2$O was added to the residue to obtain precipitates, which were washed and dried to obtain 77 mg of the white powdery crude peptide. This was analyzed by analytical HPLC and, as a result, a purity of the desired product on the chart was 83%, and a retention time was consistent with that of a chemical synthetic product. Further, a semi-synthetic product and a wholly synthetic product were coinjected, and peaks on chromatogram were consistent.

(10) Purification of hGhrelin (1–28)

67 mg of the white powdery crude hGhrelin obtained in the (9) was dissolved in 1% acetic acid at 1 mg/mL, and the solution was loaded on a reverse phase chromatography column TSK-ODS-8OTs 108 mL (ID 21.5 mm×300 mm) equilibrated with 0.1 M acetic acid. After washed with 2 column volumes of an equilibrating solution, a program was performed by which a concentration gradient of from a buffer A (0.1 M acetic acid) 100% to a buffer B (40% acetonitrile, 0.1M acetic acid) 100% was completed in 5 column volumes, thereby to elute hGhrelin (1–28). Fractions having a high purity were collected, and lyophilized to obtain 34.4 mg of hGhrelin (1–28).

ESI-MS 3371 (theoretical value 3370.86), amino acid composition ratio after hydrolysis with 6N hydrochloric acid Ala; 1.01 (1), Arg; 2.97 (3), Glx; 5.95 (6), Gly; 1.02 (1), His; 1.00 (1), Leu; 2 (2), Lys; 4.01 (4), Phe; 1.00 (1), Pro; 4.01 (4), Ser; 3.60 (4), Val; 1.00 (1) (theoretical value in parenthesis) Ca mobilization activity 1.3 nM (ref. 1.5 nM)

Example 17

Optimization of de-TBDMS Condition and Octanoylation Condition of Boc-Gly-Ser(tBu)-Ser(TBDMS)-Phe-Leu-Ser(tBu)-Pro-OH According to the same manner as that of the method of Example 16 (8–1), optimization condition of a reaction for removing a TBDMS group of the third serine and an octanoylating reaction was studied. A Boc-Gly-Ser(tBu)-Ser(TBDMS)-Phe-Leu-Ser(tBu)-Pro-2-chlorotrityl resin was constructed on a prolyl-2-chlorotrityl resin by repeating successively introduction of Fmoc-amino acid with HBTU and de-Fmoc with piperidine, to introduce Boc-Gly into an N-terminal residue using a peptide automatic synthesizer (433A manufactured by Applied Biosystem Japan). Then, the resin was subdivided into 0.05 mmol (about 150 mg), and subjected to octanoylation under conditions shown in Table 3 and Table 4. Conditions of washing of a resin, and cleavage of a peptide from the resin are the same as those of Example 16 (8–1).

As a result, it was made clear that a reaction of removing a TBDMS group is preferably performed for 30 minutes to 1 hour using a 0.1 M TBAF solution, and an octanoylating reaction is preferably performed for 8 to 16 hours using 4 equivalents of octanoic acid, 4.4 equivalents of EDC, and 1 equivalent of DMAP.

TABLE 3

Reaction of removing TBDMS group[a]

| | TBAF (M) | Reaction time (hour) | Yield[b] (%) | Purity of desired product[c] (%) | Ratio[c] Octanoyl:Desoctanoyl |
|---|---|---|---|---|---|
| I | 0.01 | 0.25 | 89 | 94 | 98.3:1.7 |
| II | 0.01 | 3 | 100 | 97 | 100:N.D.[d] |
| III | 0.1 | 0.25 | 94 | 97 | 100:N.D. |
| IV | 0.1 | 0.5 | 100 | 96 | 100:N.D. |
| V | 0.1 | 1 | 98 | 96 | 100:N.D. |
| VI | 0.1 | 3 | 100 | 96 | 100:N.D. |

[a]A rate of removing a TBDMS group was obtained as a ratio of an octanoyl compound and a desoctanoyl compound exhibiting unremoval of TBDMS, in which those compounds were obtained by octanoylating a TBAF-treated peptide resin, followed by deprotection. The octanoylation was performed by a reaction for 24 hours using 4 equivalents of octanoicacid, 4.4 equivalents of EDC, and 1 equivalent of DMAP.
[b]Calculated based on a substitution rate of a prolyl-2-chlorotrityl resin.
[c]A purity of the desired product and a rate were calculated by analytical HPLC.
[d]N.D. Not detected.

TABLE 4

Reaction of octanoylating 3-positional serine[a]

| | Octanoic acid (equivalent) | EDC (equivalent) | DMAP (equivalent) | Reaction time (hour) | Yield[b] (%) | Purity of desired product[c] (%) | Ratio[c] Octanoyl:Desoctanoyl |
|---|---|---|---|---|---|---|---|
| VII | 4 | 4.4 | 0.1 | 24 | 83 | 94 | 97.2:2.8 |
| VIII | 2 | 2.2 | 1 | 24 | 93 | 96 | 99.5:0.5 |

TABLE 4-continued

Reaction of octanoylating 3-positional serine[a]

| | Octanoic acid (equivalent) | EDC (equivalent) | DMAP (equivalent) | Reaction time (hour) | Yield[b] (%) | Purity of desired product[c] (%) | Ratio[c] Octanoyl:Desoctanoyl |
|---|---|---|---|---|---|---|---|
| IX | 4 | 4.4 | 1 | 1 | 85 | 78 | 80.5:19.5 |
| X | 4 | 4.4 | 1 | 4 | 98 | 97 | 99.7:0.3 |
| XI | 4 | 4.4 | 1 | 8 | 98 | 96 | 100:N.D.[d] |
| XII | 4 | 4.4 | 1 | 16 | 97 | 98 | 100:N.D. |

[a]All samples were treated with 0.1 M TBAF for 1 hour, to remove a TBDMS group.
[b]Calculated based on a substitution rate of a prolyl-2-chlorotrityl resin.
[c]A purity of desired product and a rate were calculated by analytical HPLC.
[d]N.D. Not detected.

Example 18

Study of Fragment Condensation Condition

Reaction efficacies of various condensing reagents were studied using [N$^\alpha$-Boc, Ser(tBu)$^{2,6}$]hGhrelin(1–7) and [Lys$^{16,19,20,24}$(Boc)]hGhrelin(8–28), it was made clear that HBTU gave the best result, but reaction proceeds also in EDC/HOBt, EDC/HOSu and DPPA.

TABLE 5

[N$^\alpha$-Boc,Ser(tBu)$^{2,6}$]Ghrelin(1–7) + hGhrelin(8–28)

| Condensing reagent | Reaction time | Purity of desired product (calculated from HPLC) |
|---|---|---|
| HBTU | 5 hours | 83% |
| EDC/HOBt | 16 hours | 74% |
| EDC/HOSu | 16 hours | 40% |
| DPPA | 24 hours | 19% |

INDUSTRIAL APPLICABILITY

According to the method of the present invention, a modified peptide or protein having very high quality can be obtained in a high yield.

---

The invention claimed is:

1. A method for producing a protected peptide fragment, wherein at least one amino acid or non-amino acid is modified as represented by the formula -A(R)—, wherein A represents an amino acid or a non-amino acid, and R represents a substituent bound to a side chain of A which is introduced for modification, which comprises:
    (a) preparing, on a weak acid-cleavable resin, a peptide main chain sequence of a peptide fragment which has a desired sequence comprising amino acids or amino acids and non-amino acids, wherein one or more reactive functional groups in a side chain of an amino acid or a non-amino acid which may cause an undesirable side reaction during preparation of a peptide fragment are protected with a protecting group, the one or more reactive functional groups being selected from the group consisting of a hydroxyl group, an amino group, a guanidino group, an imidazolyl group, an indolyl group, a mercapto group and a carboxyl group, in a side chain of an amino acid or a non-amino acid,
    (b) deprotecting the protecting group of at least one reactive functional group in the side chain of an amino acid or a non-amino acid A which is to be modified with a substituent R without cleaving the peptide fragment from the weak acid-cleavable resin,
    (c) modifying the deprotected side chain with a substituent R, and
    (d) cleaving the peptide fragment from the weak acid-cleavable resin under weakly acidic conditions.

2. The method for producing a peptide fragment according to claim 1, wherein the protecting group for a reactive functional group in a side chain of an amino acid or a non-amino acid A which is to be modified with substituent R is a silyl protecting group, and a quaternary ammonium fluoride is used for eliminating the protecting group.

3. The method for producing a peptide fragment according to claim 2, wherein the silyl protecting group is t-butyldimethylsilyl (TBDMS), t-butyldiphenylsilyl (TBDPS), triisopropylsilyl (TIPS), triisobutylsilyl (TIBS), t-hexyldimethylsilyl (ThxDMS) or triphenylsilyl (TPS), and the quatemary ammonium fluoride is tetrabutylammonium fluoride (TBAF), tetraethylammonium fluoride (TEF) or ammonium fluoride.

4. The method for producing a peptide fragment according to any one of claims 1 to 3, wherein A is serine, threonine, cysteine, homocysteine, lysine, ornithine, glutamic acid, 2-aminoadipic acid, diaminoacetic acid, 2-aminomalonic acid, aspartic acid, tyrosine or asparagine, and R is bound to a reactive substituent in the side chain of A via an ester bond, an ether bond, a thioether bond, a disulfide bond, an amide bond, an O-glycoside bond or an N-glycoside bond.

5. The method for producing a peptide fragment according to claim 4, wherein A is seine or threonine, and R is bound to the hydroxy group in the side chain of A via an ester bond.

6. The method for producing a peptide fragment according to claim 5, wherein the peptide fragment is ghrelin or a derivative thereof, or a peptide fragment containing a modified amino acid in the ghrelin or a derivative thereof.

7. A method for producing a modified peptide or protein, which comprises
    (a) preparing a protected peptide fragment containing one or more modified amino acids or non-amino acids by the method described in claim 1,
    (b) preparing a peptide fragment containing no modified amino acid or non-amino acid, and in which one or more reactive functional groups which may cause an undesirable side reaction, selected from the group consisting of a hydroxy group, an amino group, a guanidino group, an imidazolyl group, an indolyl group, a mercapto group and a carboxyl group, in the side chain of an amino acid or a non-amino acid, are protected, besides the peptide fragment of the (a), and (c) condensing peptide fragments prepared in (a) and (b).

8. The method for producing a modified peptide or protein according to claim 7, wherein condensation of the peptide fragments is performed by using a condensing agent.

9. The method for producing a modified peptide or protein according to claim 8, wherein the condensing agent is 2-(1-hydrobenzotriazol-1-yl)-1,1,3,3-tetramethyluronium hexafluorophosphate (HBTU), 2-(1-hydrobenzotriazol-1-yl)-1,1,3,3-tetramethyluronium tetrafluoroborate (TBTU), diphenylphosphorylazide (DPPA), diphenyiphosphorocyanidate (DEPC), diisopropylcarbodiimide (DIPC), dicyclohexylcarbodiimide (DCC) or 1-ethyl-3-(3-dimethylaminopropyl)carbodiimide (EDC).

10. The method for producing a modified peptide or protein according to claim 8, wherein the condensing agent is diisopropylcarbodiimide (DIPC), dicyclohexylcarbodiimide (DCC) or 1-ethyl-3-(3-dimethylaminopropyl)carbodiimide (EDC), and condensation of the peptide fragments (a) and (b) using the condensing agent is performed in the presence of 1-hydroxybenzotriazole (HOBt), 1-hydroxysuccinimide (HOSu) or 3,4-dihydro-3-hydroxy-4-oxo-benzotriazine (HOOBt).

11. The method for producing a modified peptide or protein according to any one of claims 7 to 10, which comprises producing a protected peptide fragment containing no modified amino acid or non-amino acid, by an enzymatic method or/and a genetic recombination method.

12. The method for producing a modified peptide or protein according to claim 11, wherein the protected peptide fragment containing no modified amino acid or non-amino acid is produced by a method comprising:

(1) culturing a cell transformed with an expression vector having one of a nucleotide sequence encoding a peptide having an amino acid sequence of the peptide fragment (hereinafter referred to as desired peptide, in the present claim) or a nucleotide sequence encoding a fusion protein optionally with a protective peptide added to the desired peptide via a linker sequence, and collecting the desired peptide or the fusion protein from the culture;

(2) cleaving and separating the protected peptide and, optionally, the linker sequence and the desired peptide from the resulting fusion protein, and optionally further purifying the desired peptide when the fusion protein is collected in the step (1); and (3) protecting, with a protecting group, one or more reactive functional groups which may cause an undesirable side reaction, selected from the group consisting of a hydroxy group, an amino group, a guanidino group, an imidazolyl group, an indolyl group, a mercapto group and a carboxyl group, in the side chain of the desired peptide obtained in (1) or (2).

13. The method for producing a modified peptide or protein according to claim 12, wherein cleavage and separation of the protective peptide and, optionally, the linker sequence and the desired peptide in (2) are performed at two steps using an OmpT protease or a derivative thereof and Kex2 protease or a derivative thereof.

14. The method for producing a modified peptide or protein according to claim 12, wherein the linker sequence is a sequence set forth in SEQ ID NO: 27.

15. The method for producing a modified peptide or protein according to claim 11, wherein the peptide fragment is a peptide fragment containing no modified amino acid or non-amino acid in ghrelin or a derivative thereof.

16. The method for producing a modified peptide or protein according to claim 11, wherein the protected peptide fragment containing no modified amino acid or non-amino acid is purified and stored in a solution having a pH of 4 to 8.

17. The method for producing a modified peptide or protein according to claim 11, wherein the protecting group is a Boc group.

18. A method for producing a protected peptide fragment containing no modified amino acid or a non-amino acid, which comprises producing the peptide fragment by a method comprising:

(1) culturing a cell transformed with an expression vector having one of a nucleotide sequence encoding a peptide having the desired amino acid sequence (hereinafter, referred to as desired peptide, in the present claim) or a nucleotide sequence encoding a fusion protein optionally with a protective peptide added to the desired peptide via a linker sequence, and collecting the desired peptide or the fusion protein from the culture;

(2) cleaving and separating the protective peptide and, optionally, the linker sequence and the desired peptide from the resulting fusion protein and, optionally further purifying this, when the fusion protein is collected in (1);

(3) protecting, with a protecting group, one or more reactive substituents which may cause an undesirable side reaction, selected from the group consisting of a hydroxy group, an amino group, a guanidino group, an imidazolyl group, an indolyl group, a mercapto group and a carboxyl group, in the side chain of the desired peptide obtained in the step (1) or (2); and (4) purifying and storing the protected desired peptide obtained in (3) in a solution having a pH of 4 to 8.

19. The method for producing a protected peptide fragment containing no modified amino acid or non-amino acid according to claim 18, wherein the protecting group is a Boc group.

20. The method for producing a protected peptide fragment containing no modified amino acid or non-amino acid according to claims 18 or 19, wherein cleavage and separation of the protective peptide and, optionally, the linker sequence and the desired peptide in (2) are performed at two steps using an OmpT protease or a derivative thereof and Kex2 protease or a derivative thereof.

21. The method for producing a protected peptide fragment containing no modified amino acid or non-amino acid according to claims 18 or 19, wherein the linker sequence is a sequence set forth in SEQ ID NO: 27.

22. The method for producing a modified peptide or protein according to claims 18 or 19, wherein the peptide fragment is a peptide fragment containing no modified amino acid or non-amino acid in ghrelin or a derivative thereof.

23. The method for producing a peptide fragment according to claim 7, wherein a protecting group for a reactive functional group in a side chain of an amino acid or a non-amino acid A which is to be modified with a substituent R is a silyl protecting group, and a quaternary ammonium fluoride is used for eliminating the protecting group.

24. The method for producing a peptide fragment according to claim 23, wherein the silyl protecting group is t-butyldimethylsilyl (TBDMS), t-butyldiphenylsilyl (TBDPS), triisopropylsilyl (TIPS), triisobutylsilyl (TIBS), t-hexyldimethylsilyl (ThxDMS) or triphenylsilyl (TPS), and the quaternary ammonium fluoride is tetrabutylammonium fluoride (TBAF), tetraethylammonium fluoride (TEF) or ammonium fluoride.

25. The method for producing a peptide fragment according to any one of claims 7, 23, or 24, wherein A is seine, threonine, cysteine, homocysteine, lysine, omithine, glutamic acid, 2-aminoadipic acid, diaminoacetic acid, 2-aminomalonic acid, aspartic acid, tyrosine or asparagine, and R is bound to a reactive substituent in the side chain of A via an ester bond, an ether bond, a thioether bond, a disulfide bond, an amide bond, an O-glycoside bond or an N-glycoside bond.

26. The method for producing a peptide fragment according to claim 25, wherein A is seine or threonine, and R is bound to the hydroxy group in the side chain of A via an ester bond.

27. The method for producing a peptide fragment according to claim 26, wherein the peptide fragment is ghrelin or a derivative thereof, or a peptide fragment containing a modified amino acid in the ghrelin or a derivative thereof.

28. The method for producing a modified peptide or protein according to claim 13, wherein the linker sequence is a sequence set forth in SEQ ID NO: 27.

* * * * *

UNITED STATES PATENT AND TRADEMARK OFFICE
CERTIFICATE OF CORRECTION

PATENT NO. : 7,138,489 B2 Page 1 of 1
APPLICATION NO. : 10/500018
DATED : November 21, 2006
INVENTOR(S) : Yoshiharu Minamitake et al.

It is certified that error appears in the above-identified patent and that said Letters Patent is hereby corrected as shown below:

On Title Page Item (73), change "Daiichi Asubio Pharma Co., Ltd., Tokyo (JP)" to --Daiichi Asubio Pharma Co., Ltd., Tokyo (JP) and Kenji Kangawa, Osaka (JP)--;

Signed and Sealed this

Sixth Day of March, 2007

JON W. DUDAS
*Director of the United States Patent and Trademark Office*

SEQUENCE LISTING

<160> NUMBER OF SEQ ID NOS: 39

<210> SEQ ID NO 1
<211> LENGTH: 28
<212> TYPE: PRT
<213> ORGANISM: Homo sapiens
<220> FEATURE:
<223> OTHER INFORMATION: Amino acid sequence for human endogenous
      peptides of growth hormone secretagogue

<400> SEQUENCE: 1

Gly Ser Ser Phe Leu Ser Pro Glu His Gln Arg Val Gln Gln Arg Lys
 1               5                   10                  15

Glu Ser Lys Lys Pro Pro Ala Lys Leu Gln Pro Arg
            20                  25

<210> SEQ ID NO 2
<211> LENGTH: 27
<212> TYPE: PRT
<213> ORGANISM: Homo sapiens
<220> FEATURE:
<223> OTHER INFORMATION: Amino acid sequence for human endogenous
      peptides (27 amino acids)of growth hormone secretagogue

<400> SEQUENCE: 2

Gly Ser Ser Phe Leu Ser Pro Glu His Gln Arg Val Gln Arg Lys Glu

```
                   1               5                  10                  15
Ser Lys Lys Pro Pro Ala Lys Leu Gln Pro Arg
                  20                  25

<210> SEQ ID NO 3
<211> LENGTH: 28
<212> TYPE: PRT
<213> ORGANISM: Rattus norvegicus
<220> FEATURE:
<223> OTHER INFORMATION: Amino acid sequence for rat endogenous peptides
      of growth hormone secretagogue

<400> SEQUENCE: 3

Gly Ser Ser Phe Leu Ser Pro Glu His Gln Lys Ala Gln Gln Arg Lys
 1               5                  10                  15

Glu Ser Lys Lys Pro Pro Ala Lys Leu Gln Pro Arg
                  20                  25

<210> SEQ ID NO 4
<211> LENGTH: 27
<212> TYPE: PRT
<213> ORGANISM: Rattus norvegicus
<220> FEATURE:
<223> OTHER INFORMATION: Amino acid sequence for rat endogenous peptides
      (27 amino acids) of growth hormone secretagogue

<400> SEQUENCE: 4

Gly Ser Ser Phe Leu Ser Pro Glu His Gln Lys Ala Gln Arg Lys Glu
 1               5                  10                  15

Ser Lys Lys Pro Pro Ala Lys Leu Gln Pro Arg
                  20                  25

<210> SEQ ID NO 5
<211> LENGTH: 28
<212> TYPE: PRT
<213> ORGANISM: Mus musculus
<220> FEATURE:
<223> OTHER INFORMATION: Amino acid sequence for mouse endogenous
      peptides of growth hormone secretagogue

<400> SEQUENCE: 5

Gly Ser Ser Phe Leu Ser Pro Glu His Gln Lys Ala Gln Gln Arg Lys
 1               5                  10                  15

Glu Ser Lys Lys Pro Pro Ala Lys Leu Gln Pro Arg
                  20                  25

<210> SEQ ID NO 6
<211> LENGTH: 28
<212> TYPE: PRT
<213> ORGANISM: Sus scrofa (pig)
<220> FEATURE:
<223> OTHER INFORMATION: Amino acid sequence for porcine endogenous
      peptides of growth hormone secretagogue

<400> SEQUENCE: 6

Gly Ser Ser Phe Leu Ser Pro Glu His Gln Lys Val Gln Gln Arg Lys
 1               5                  10                  15

Glu Ser Lys Lys Pro Ala Ala Lys Leu Lys Pro Arg
                  20                  25

<210> SEQ ID NO 7
<211> LENGTH: 27
<212> TYPE: PRT
<213> ORGANISM: Bos taurus
<220> FEATURE:
```

```
<223> OTHER INFORMATION: Amino acid sequence for bovine endogenous
      peptides (27 amino acids) of growth hormone secretagogue

<400> SEQUENCE: 7

Gly Ser Ser Phe Leu Ser Pro Glu His Gln Lys Leu Gln Arg Lys Glu
 1               5                  10                  15

Ala Lys Lys Pro Ser Gly Arg Leu Lys Pro Arg
            20                  25

<210> SEQ ID NO 8
<211> LENGTH: 27
<212> TYPE: PRT
<213> ORGANISM: Ovis aries
<220> FEATURE:
<223> OTHER INFORMATION: Amino acid sequence for ovine endogenous
      peptides (27 amino acids) of growth hormone secretagogue

<400> SEQUENCE: 8

Gly Ser Ser Phe Leu Ser Pro Glu His Gln Lys Leu Gln Arg Lys Glu
 1               5                  10                  15

Pro Lys Lys Pro Ser Gly Arg Leu Lys Pro Arg
            20                  25

<210> SEQ ID NO 9
<211> LENGTH: 28
<212> TYPE: PRT
<213> ORGANISM: Canis familiaris
<220> FEATURE:
<223> OTHER INFORMATION: Amino acid sequence for dog endogenous peptides
      of growth hormone secretagogue

<400> SEQUENCE: 9

Gly Ser Ser Phe Leu Ser Pro Glu His Gln Lys Leu Gln Gln Arg Lys
 1               5                  10                  15

Glu Ser Lys Lys Pro Pro Ala Lys Leu Gln Pro Arg
            20                  25

<210> SEQ ID NO 10
<211> LENGTH: 21
<212> TYPE: PRT
<213> ORGANISM: Anguilla japonica
<220> FEATURE:
<221> NAME/KEY: AMIDATION
<222> LOCATION: 21
<223> OTHER INFORMATION: Amino acid sequence for eel endogenous peptides
      of growth hormone secretagogue

<400> SEQUENCE: 10

Gly Ser Ser Phe Leu Ser Pro Ser Gln Arg Pro Gln Gly Lys Asp Lys
 1               5                  10                  15

Lys Pro Pro Arg Val
            20

<210> SEQ ID NO 11
<211> LENGTH: 23
<212> TYPE: PRT
<213> ORGANISM: Oncorhynchus mykiss
<220> FEATURE:
<221> NAME/KEY: AMIDATION
<222> LOCATION: 23
<223> OTHER INFORMATION: Amino acid sequence for rainbow trout
      endogenous peptides (23 amino acids) of growth hormone
      secretagogue

<400> SEQUENCE: 11

Gly Ser Ser Phe Leu Ser Pro Ser Gln Lys Pro Gln Val Arg Gln Gly
```

```
                  1               5              10              15
Lys Gly Lys Pro Pro Arg Val
                              20

<210> SEQ ID NO 12
<211> LENGTH: 20
<212> TYPE: PRT
<213> ORGANISM: Oncorhynchus mykiss
<220> FEATURE:
<221> NAME/KEY: AMIDATION
<222> LOCATION: 20
<223> OTHER INFORMATION: Amino acid sequence for rainbow trout
      endogenous peptides (20 amino acids) of growth hormone
      secretagogue

<400> SEQUENCE: 12

Gly Ser Ser Phe Leu Ser Pro Ser Gln Lys Pro Gln Gly Lys Gly Lys
  1               5              10                      15

Pro Pro Arg Val
             20

<210> SEQ ID NO 13
<211> LENGTH: 24
<212> TYPE: PRT
<213> ORGANISM: Gallus domesticus
<220> FEATURE:
<223> OTHER INFORMATION: Amino acid sequence for chicken endogenous
      peptides of growth hormone secretagogue

<400> SEQUENCE: 13

Gly Ser Ser Phe Leu Ser Pro Thr Tyr Lys Asn Ile Gln Gln Gln Lys
  1               5              10                      15

Gly Thr Arg Lys Pro Thr Ala Arg
             20

<210> SEQ ID NO 14
<211> LENGTH: 24
<212> TYPE: PRT
<213> ORGANISM: Gallus domesticus
<220> FEATURE:
<223> OTHER INFORMATION: Amino acid sequence for chicken endogenous
      peptides of growth hormone secretagogue

<400> SEQUENCE: 14

Gly Ser Ser Phe Leu Ser Pro Thr Tyr Lys Asn Ile Gln Gln Gln Lys
  1               5              10                      15

Asp Thr Arg Lys Pro Thr Ala Arg
             20

<210> SEQ ID NO 15
<211> LENGTH: 26
<212> TYPE: PRT
<213> ORGANISM: Gallus domesticus
<220> FEATURE:
<223> OTHER INFORMATION: Amino acid sequence for chicken endogenous
      peptides of growth hormone secretagogue

<400> SEQUENCE: 15

Gly Ser Ser Phe Leu Ser Pro Thr Tyr Lys Asn Ile Gln Gln Gln Lys
  1               5              10                      15

Asp Thr Arg Lys Pro Thr Ala Arg Leu His
             20                  25

<210> SEQ ID NO 16
<211> LENGTH: 27
```

```
<212> TYPE: PRT
<213> ORGANISM: Rana cafesbeiana
<220> FEATURE:
<223> OTHER INFORMATION: Amino acid sequence for frog endogenous
      peptides of growth hormone secretagogue

<400> SEQUENCE: 16

Gly Leu Thr Phe Leu Ser Pro Ala Asp Met Gln Lys Ile Ala Glu Arg
 1               5                  10                  15

Gln Ser Gln Asn Lys Leu Arg His Gly Asn Met
                20                  25

<210> SEQ ID NO 17
<211> LENGTH: 28
<212> TYPE: PRT
<213> ORGANISM: Rana cafesbeiana
<220> FEATURE:
<223> OTHER INFORMATION: Amino acid sequence for frog endogenous
      peptides of growth hormone secretagogue

<400> SEQUENCE: 17

Gly Leu Thr Phe Leu Ser Pro Ala Asp Met Gln Lys Ile Ala Glu Arg
 1               5                  10                  15

Gln Ser Gln Asn Lys Leu Arg His Gly Asn Met Asn
                20                  25

<210> SEQ ID NO 18
<211> LENGTH: 20
<212> TYPE: PRT
<213> ORGANISM: Tilapia nilotica
<220> FEATURE:
<221> NAME/KEY: AMIDATION
<222> LOCATION: 20
<223> OTHER INFORMATION: Amino acid sequence for tilapia endogenous
      peptides of growth hormone secretagogue

<400> SEQUENCE: 18

Gly Ser Ser Phe Leu Ser Pro Ser Gln Lys Pro Gln Asn Lys Val Lys
 1               5                  10                  15

Ser Ser Arg Ile
                20

<210> SEQ ID NO 19
<211> LENGTH: 22
<212> TYPE: PRT
<213> ORGANISM: Silurus asotus
<220> FEATURE:
<221> NAME/KEY: AMIDATION
<222> LOCATION: 22
<223> OTHER INFORMATION: Amino acid sequence for catfish endogenous
      peptides of growth hormone secretagogue

<400> SEQUENCE: 19

Gly Ser Ser Phe Leu Ser Pro Thr Gln Lys Pro Gln Asn Arg Gly Asp
 1               5                  10                  15

Arg Lys Pro Pro Arg Val
                20

<210> SEQ ID NO 20
<211> LENGTH: 23
<212> TYPE: PRT
<213> ORGANISM: Silurus asotus
<220> FEATURE:
<223> OTHER INFORMATION: Amino acid sequence for catfish endogenous
      peptides of growth hormone secretagogue

<400> SEQUENCE: 20
```

```
Gly Ser Ser Phe Leu Ser Pro Thr Gln Lys Pro Gln Asn Arg Gly Asp
  1               5                  10                  15

Arg Lys Pro Pro Arg Val Gly
             20
```

<210> SEQ ID NO 21
<211> LENGTH: 28
<212> TYPE: PRT
<213> ORGANISM: Equus caballus
<220> FEATURE:
<223> OTHER INFORMATION: Amino acid sequence for equine endogenous
      peptides of growth hormone secretagogue

<400> SEQUENCE: 21

```
Gly Ser Ser Phe Leu Ser Pro Glu His His Lys Val Gln His Arg Lys
  1               5                  10                  15

Glu Ser Lys Lys Pro Pro Ala Lys Leu Lys Pro Arg
             20                  25
```

<210> SEQ ID NO 22
<211> LENGTH: 4
<212> TYPE: PRT
<213> ORGANISM: Artificial sequence
<220> FEATURE:
<223> OTHER INFORMATION: Amino acid sequence adjacent to a site cleaved
      by enterokinase

<400> SEQUENCE: 22

```
Asp Asp Asp Lys
  1
```

<210> SEQ ID NO 23
<211> LENGTH: 4
<212> TYPE: PRT
<213> ORGANISM: Artificial sequence
<220> FEATURE:
<223> OTHER INFORMATION: Amino acid sequence adjacent to a site cleaved
      by blood coagulation Factor Xa

<400> SEQUENCE: 23

```
Ile Glu Gly Arg
  1
```

<210> SEQ ID NO 24
<211> LENGTH: 7
<212> TYPE: PRT
<213> ORGANISM: Artificial sequence
<220> FEATURE:
<223> OTHER INFORMATION: Amino acid sequence containing a site cleaved
      by renin

<400> SEQUENCE: 24

```
Pro Phe His Leu Leu Val Tyr
  1               5
```

<210> SEQ ID NO 25
<211> LENGTH: 6
<212> TYPE: PRT
<213> ORGANISM: Artificial sequence
<220> FEATURE:
<223> OTHER INFORMATION: Synthetic construct

<400> SEQUENCE: 25

```
Val Asp Asp Asp Asp Lys
  1               5
```

<210> SEQ ID NO 26
<211> LENGTH: 36
<212> TYPE: PRT
<213> ORGANISM: Artificial sequence
<220> FEATURE:
<223> OTHER INFORMATION: linker sequence in the fusion protein p117
      8-28oPR

<400> SEQUENCE: 26

Glu Pro His His His His Pro Gly Gly Arg Gln Met His Gly Tyr Asp
1               5                   10                  15

Ala Asp Val Arg Leu Tyr Arg Arg His His Gly Ser Gly Ser Pro Ser
            20                  25                  30

Arg His Pro Arg
        35

<210> SEQ ID NO 27
<211> LENGTH: 36
<212> TYPE: PRT
<213> ORGANISM: Artificial sequence
<220> FEATURE:
<223> OTHER INFORMATION: linker sequence in the fusion protein p117
      8-28oRR

<400> SEQUENCE: 27

Glu Pro His His His His Pro Gly Gly Arg Gln Met His Gly Tyr Asp
1               5                   10                  15

Ala Asp Val Arg Leu Tyr Arg Arg His His Gly Ser Gly Ser Pro Ser
            20                  25                  30

Arg His Arg Arg
        35

<210> SEQ ID NO 28
<211> LENGTH: 36
<212> TYPE: DNA
<213> ORGANISM: Artificial sequence
<220> FEATURE:
<223> OTHER INFORMATION: primer ORI-RR

<400> SEQUENCE: 28
ggttccggat cccttctcg acatcgccgg gaacac                              36

<210> SEQ ID NO 29
<211> LENGTH: 25
<212> TYPE: DNA
<213> ORGANISM: Artificial sequence
<220> FEATURE:
<223> OTHER INFORMATION: primer SAL*R

<400> SEQUENCE: 29
ataagtcgac ttatcgtggc tgcag                                         25

<210> SEQ ID NO 30
<211> LENGTH: 13
<212> TYPE: PRT
<213> ORGANISM: Artificial sequence
<220> FEATURE:
<223> OTHER INFORMATION: Synthetic construct

<400> SEQUENCE: 30

Arg His His Gly Ser Gly Ser Pro Ser Arg His Arg Arg
1               5                   10

<210> SEQ ID NO 31

```
<211> LENGTH: 13
<212> TYPE: PRT
<213> ORGANISM: Artificial sequence
<220> FEATURE:
<223> OTHER INFORMATION: Synthetic construct

<400> SEQUENCE: 31

Arg His His Gly Ser Gly Ser Pro Ser Arg His Pro Arg
 1               5                  10

<210> SEQ ID NO 32
<211> LENGTH: 13
<212> TYPE: PRT
<213> ORGANISM: Artificial sequence
<220> FEATURE:
<223> OTHER INFORMATION: Synthetic construct

<400> SEQUENCE: 32

Arg His His Gly Ser Gly Ser Pro Ser Arg His Lys Arg
 1               5                  10

<210> SEQ ID NO 33
<211> LENGTH: 7
<212> TYPE: PRT
<213> ORGANISM: Artificial sequence
<220> FEATURE:
<223> OTHER INFORMATION: Synthetic construct

<400> SEQUENCE: 33

Gly Ser Ser Phe Leu Ser Pro
 1               5

<210> SEQ ID NO 34
<211> LENGTH: 4
<212> TYPE: PRT
<213> ORGANISM: Artificial sequence
<220> FEATURE:
<223> OTHER INFORMATION: Synthetic construct

<400> SEQUENCE: 34

Phe Leu Ser Pro
 1

<210> SEQ ID NO 35
<211> LENGTH: 14
<212> TYPE: PRT
<213> ORGANISM: Artificial sequence
<220> FEATURE:
<223> OTHER INFORMATION: linker sequence

<400> SEQUENCE: 35

Arg Arg His His Gly Ser Gly Ser Pro Ser Arg His Pro Arg
 1               5                  10

<210> SEQ ID NO 36
<211> LENGTH: 27
<212> TYPE: DNA
<213> ORGANISM: Artificial sequence
<220> FEATURE:
<223> OTHER INFORMATION: h8-28f1 - synthetic oligo-DNA nucleotide
      sequence

<400> SEQUENCE: 36
tccccgcggg aaccaccagcg cgtccag                                          27

<210> SEQ ID NO 37
<211> LENGTH: 33
```

```
<212> TYPE: DNA
<213> ORGANISM: Artificial sequence
<220> FEATURE:
<223> OTHER INFORMATION: h8-28r1

<400> SEQUENCE: 37
acgctgctgg acgcgctggt gttcccgcgg gga                                33

<210> SEQ ID NO 38
<211> LENGTH: 49
<212> TYPE: DNA
<213> ORGANISM: Artificial sequence
<220> FEATURE:
<223> OTHER INFORMATION: GR2f

<400> SEQUENCE: 38
cagcgtaagg aatccaagaa gccaccagct aaactgcagc cacgatgag                49

<210> SEQ ID NO 39
<211> LENGTH: 44
<212> TYPE: DNA
<213> ORGANISM: Artificial sequence
<220> FEATURE:
<223> OTHER INFORMATION: GR2r

<400> SEQUENCE: 39
tcgactcatc gtggctgcag tttagctggc ttcttggatt cctt                    44
```